(12) United States Patent
Elmore et al.

(10) Patent No.: US 7,842,681 B2
(45) Date of Patent: Nov. 30, 2010

(54) TREATMENT OF MYEOPROLIFERATIVE DISEASES

(75) Inventors: Steven W. Elmore, Northbrook, IL (US); Saul Rosenberg, Grayslake, IL (US); Gary Gordon, Highland Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/850,274

(22) Filed: Sep. 5, 2007

(65) Prior Publication Data

US 2008/0076779 A1 Mar. 27, 2008

Related U.S. Application Data

(60) Provisional application No. 60/842,254, filed on Sep. 5, 2006.

(51) Int. Cl.
  *A01N 51/00* (2006.01)
  *A61K 31/60* (2006.01)
(52) U.S. Cl. ...................... 514/183; 514/155
(58) Field of Classification Search .................. 514/183
  See application file for complete search history.

(56) References Cited

U.S. PATENT DOCUMENTS

| | | | |
|---|---|---|---|
| 5,306,709 | A | 4/1994 | Gewirtz |
| 6,703,382 | B2 * | 3/2004 | Wang et al. ............... 514/183 |
| 6,720,338 | B2 | 4/2004 | Augeri et al. |
| 7,030,115 | B2 | 4/2006 | Elmore et al. |
| 7,358,251 | B2 | 4/2008 | Elmore et al. |
| 7,390,799 | B2 | 6/2008 | Bruncko et al. |
| 7,449,485 | B2 | 11/2008 | Elmore et al. |
| 7,504,512 | B2 | 3/2009 | Augeri et al. |
| 7,585,858 | B2 | 9/2009 | Elmore et al. |
| 7,642,260 | B2 | 1/2010 | Bruncko et al. |
| 2002/0086887 | A1 | 7/2002 | Augeri et al. |
| 2003/0119894 | A1 | 6/2003 | Murthy et al. |
| 2004/0209907 | A1 | 10/2004 | Franklin |
| 2006/0128706 | A1 | 6/2006 | Bruncko et al. |
| 2006/0258657 | A1 | 11/2006 | Bruncko et al. |
| 2007/0015787 | A1 | 1/2007 | Bruncko et al. |
| 2007/0027135 | A1 | 2/2007 | Bruncko et al. |
| 2007/0072860 | A1 | 3/2007 | Bruncko et al. |
| 2008/0287419 | A1 | 11/2008 | Bruncko et al. |

FOREIGN PATENT DOCUMENTS

| | | |
|---|---|---|
| NZ | 230136 | 12/1991 |
| WO | WO 00/04901 | 2/2000 |
| WO | WO 02/13833 | 2/2002 |
| WO | WO 02/24636 A2 | 3/2002 |
| WO | WO 02/098848 | 12/2002 |
| WO | WO 2005/049594 A1 | 6/2005 |
| WO | WO 2007/040650 A2 | 4/2007 |
| WO | WO 2008/017121 A1 | 2/2008 |
| WO | WO 2008/017123 A1 | 2/2008 |

OTHER PUBLICATIONS

Hawkins et. al., Meyloproliferative Disorders, University of Maryland Medical Center, online publication, Oct. 19, 2006.*
Oltersdorf., An inhibitor of Bcl-2 family proteins induces regression of solid tumours, Nature, vol. 435, May 15, 2005.*
Zhang et. al. (Haematologica (2004) 89:1199-1206).*
Gangat et. al. (Expert Opinion on Pharmacotherapy (2008) 9:1679-1685.*
Lengfelder et. al. (Seminars in Thrombosis and Hemostasis (2006) 32:267-275).*
Yanhong Ma et. al., Biochimmica et Biophysica Acta (2009) 1073-1079.*
Finazzi, et al., "Essential Thrombocythemia", Seminars in Hematology, 42, 230-238 (2005).
Harrison, et al., "Hydroxyurea Compared with Anagrelide in high-Risk Essential Thrombocythemia", New Engl J Med, 353, 33-45 (2005).
IUPAC 1974 Recommendations for Sec E, Fundamental Stereochemistry, Pure Appl Chem,45,13-30 (1976).
Lengfelder, et al., "Diagnosis and Therapy of Polycythemia Vera", Seminars In Thrombosis and Hemostasis, 32 (3), 267-275 (2006).
Mitra, et al., "In Stent restenosis: bane of the stent era", J Clin Pathol, 59, 232-239 (2006).
Petros, et al., "Solution structure of the antiapoptotic protein bcl-2", PNAS, 98(6), 3012-3017 (2001).
Sattler, et al., "Structure of Bcl-xL-Bak Peptide Complex: Recognition Between Regulators of Apoptosis", Science 275, 983-986 (1997).

(Continued)

*Primary Examiner*—Brandon J Fetterolf
*Assistant Examiner*—Marcos Sznaidman
(74) *Attorney, Agent, or Firm*—Oona A. Manzari; Gregory B. Donner

(57) ABSTRACT

Methods of reducing the number of platelets in mammals and preventing or treating pro-thrombotic conditions and diseases that are characterized by an excess of, or undesired activation of, platelets using inhibitors of anti-apoptotic Bcl-2 family protein members is disclosed.

8 Claims, 5 Drawing Sheets

OTHER PUBLICATIONS

Weston, et al., "Antiplatelet Drugs in Cardiovascular Diseases", International Journal of Clinical Practice, 57(10), 898-905 (2003).

Zhang, et al., "Development of a high-throughput fluorescence polarization assay for Bcl-xL", Analytical Biochemistry, 307, 70-75 (2002).

Zhang, et al., "Bcl-2 family proteins are essential for platelet survival", Cell death and Differentiation, 14, 943-951 (2007).

Mason, et al., "The Bcl-2 Protein Family Is Essential for Platelet Survival in Vivo", Blood (48th ASH Annual Meeting Abstracts) vol. 108 No. 11, Part 1 pp. 209A (2006).

Merritt, et al., "The Efficacy and Safety of Perioperative Antiplatelet Therapy", Journal of Thrombosis and Thrombolysis, 17(1), 21-27 (2004).

Letai, A., 2005, "The BCL-2 network: Mechanistic insights and therapeutic potential," *Drug Discovery Today: Disease Mechanisms*, vol. 2(2):145-151.

Mitten, M.J. et al., 2005, "The Bcl-2 inhibitor ABT-737 shows significant anit-tumor efficacy in a model of non-Hodgkin's B cell lymphoma," *Proceedings of the Annual Meeting of the American Association for Cancer Research*, vol. 46:399-400.

PCT International Written Opinion dated Jul. 29, 2008, in International Application No. PCT/US2007/077579, filed Sep. 5, 2007.

PCT International Search Report Jul. 29, 2008, in International Application No. PCT/US2007/077579, filed Sep. 5, 2007.

U.S.P.T.O. Non-Final Office Action dated Sep. 12, 2008, in U.S. Appl. No. 11/202,827, filed Aug. 12, 2005.

U.S.P.T.O. Non-Final Office Action dated Aug. 21, 2008, in U.S. Appl. No. 11/127,940, filed May 12, 2005.

Shimazaki, et al., "Evaluation of apoptosis as a prognostic factor in myelodysplastic syndromes", British J Haematology, 110(3), 584-590 (2000).

Tse et al., "ABT-263: A Potent and Orally Bioavailable Bcl-2 Family Inhibitor," May 1, 2008, Cancer Research 68(9):3421-3428.

U.S.P.T.O., Non-final Office Action dated Aug. 21, 2009 in U.S. Appl. No. 11/127,940.

Wagner et al., "Conditional deletion of the *Bcl-x* gene from erythroid cells results in hemolytic anemia and profound splenomegaly," Development, 127, 4949-4958 (2000).

Birgegard, et al., "Adverse effects and benefits of two years of anagrelide treatment for thrombocythemia in chronic myeloproliferative disorders," Haematologica, 2004, 89, pp. 520-527.

Degterev, et al., "Identification of small-molecule inhibitors of interaction between the BH3 domain and Bcl-$x_L$," Nature Cell Biology, 2001. 3, pp. 173-182.

Enyedy, et al., "Discovery of Small-Molecule Inhibitors of Bcl-2 through Structure-Based Computer Screening," J. Med. Chem., 2001, 44, pp. 4313-4324.

James, et al., "A unique clonal JAK2 mutation leading to constituative signaling causes polycythaemia vera," Nature, 2005, 434, pp. 1144-1148.

James, et al., "A JAK2 mutation in myeloproliferative disorders: pathogenesis and therapeutic and scientific prospects," Trends in Molecular Medicine, 2005, 11, pp. 546-554.

Kutzki, et al., "Development of Potent Bcl-xl Antagonist Based on α-Helix Mimicry," J. Am. Chem. Soc., 2002, 124, pp. 11838-11839.

Ma, et al., "Real-time bioluminescence imaging of polycythemia vera development in mice," Biochemica et Biophysica Acta, 2009, 1792, pp. 1073-1079.

Pereira, et al., "Platelet aging in vivo is associated with activation of apoptotic pathways: studies in a model of suppressed thrombopoiesis in dogs," Thromb. Haemost., 2002, 87(5), pp. 905-909.

P/S/L Consulting Group Inc., Press Release: "FDA Clears Agrylin for a Broader Patient Population," Dec. 21, 1998, retrieved May 10, 2010, from Doctor's Guide: Global Edition website (http://www.pslgroup.com/dg/D57EE.htm).

Shire US Manufacturing Inc., Agrylin®—anagrelide hydrochloride capsule product label, 2005, pp. 1-8, downloaded May 16, 2010 from http://dailymed.nlm.nih.gov/dailymed/drugInfo.cfm?id=14398#nlm34067-9.

Silva, et al., "Expression of Bcl-x in Erythroid Precursors from Patients with Polycythemia Vera," The New England Journal of Medicine, 1998, 338, pp. 564-571.

The Leukemia & Lymphoma Society, "Polycythemia Vera," Fact Sheet No. 13, p. 3, downloaded on May 18, 2010 from http://www.leukemia-lymphoma.org/attachments/National/br_1178803767.pdf.

Zeuner, et al., "Activity of the BH3 mimetic ABT-737 on polycythemia vera erythroid precursor cells," Blood, 2009, 113, No. 7, pp. 1522-1525.

* cited by examiner ated cells is less defined. Cytochrome c, caspase-9, caspase-3, and APAF-1 have been reported to be expressed in platelets indicating that platelets contain the necessary apoptotic machinery to execute programmed cell death. Several studies have demonstrated that the Bcl-2 family proteins (i.e. Bax, Bak, Bcl-$X_L$, and Bcl-2) are also expressed in platelets. The Bcl-2 family of proteins are the key regulators of mitochondria-dependent apoptosis in nucleated cells and consists of both anti-apoptotic (Bcl-$X_L$, Bcl-2, Bcl-w, A1, Mcl-1) and pro-apoptotic (Bak, Bax, Bid, Bim, Bad, Bik, Bmf, Noxa, Puma) members. The decision for a cell to progress through the apoptotic pathway is dependent on the interplay between these pro-survival and pro-death proteins. The pro-apoptotic proteins propagate the death signal by ultimately inducing permeabilization of the mitochondrial membrane, release of cytochrome c and caspase activation. The anti-apoptotic family members exert their protective effects by directly binding to and sequestering their pro-apoptotic counterparts. Inhibition of anti-apoptotic Bcl-2 protein family members is known to induce apoptosis in cells that are dependent on these proteins for survival.

TREATMENT OF MYEOPROLIFERATIVE DISEASES

This application claims the benefit under 35 U.S.C. §119(e) of U.S. Provisional Application No. 60/842,254 filed Sep. 5, 2006.

FIELD OF THE INVENTION

The invention comprises methods of reducing the number of platelets in mammals and preventing or treating pro-thrombotic conditions and diseases that are characterized by an excess of, or undesired activation of, platelets using inhibitors of anti-apoptotic Bcl-2 family protein members.

BACKGROUND OF THE INVENTION

Platelets are anucleated blood cells derived from megakaryocytes that are essential for proper hemostasis and thrombosis. Apoptosis-like processes have also been linked to platelet biogenesis (i.e. thrombopoiesis) and aging (i.e. senescence). The processes of apoptosis have been extensively studied in nucleated cells; however, its role in anucleated cells is less defined.

Although circulating platelet production is a normal physiological process, a number of diseases are caused or exacerbated by excess of, or undesired activation of, platelets. There is therefore an existing need in the therapeutic arts for methods of reducing the number of platelets in mammals and preventing or treating pro-thrombotic conditions and diseases that are characterized by an excess of, or undesired activation of, platelets.

SUMMARY OF THE INVENTION

Figure 1:
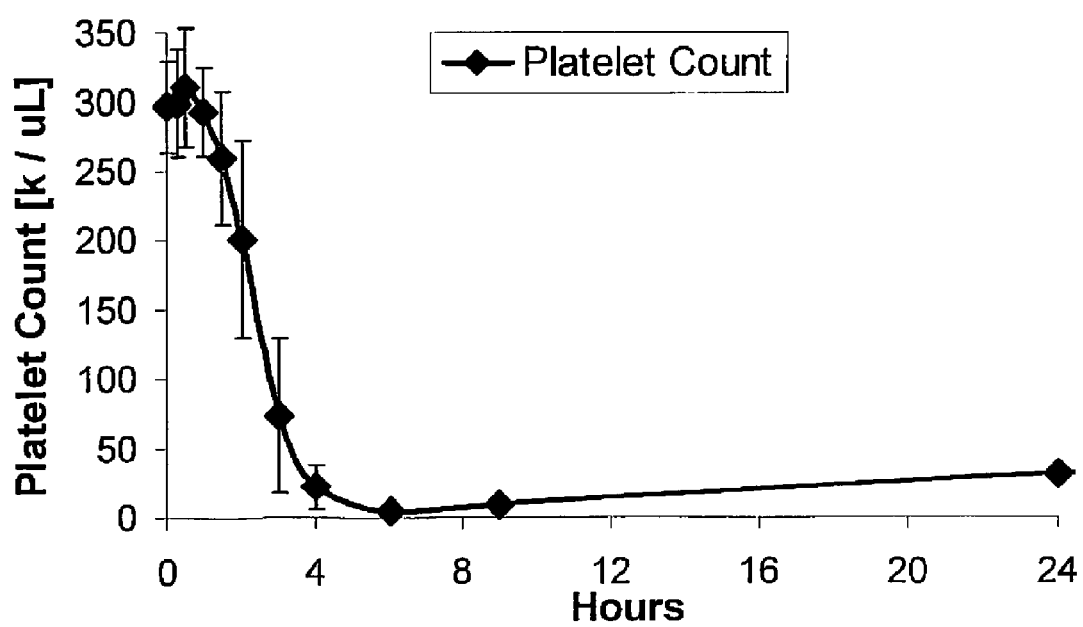
FIG. 1 shows the effect of oral administration of N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide on circulating platelets in dogs over 24 hours.

We have discovered that inhibitors of Bcl-2 protein family members can induce a rapid, dose-dependent decrease in circulating platelets in multiple species.

Therefore, one embodiment of this invention comprises compositions for preventing or treating diseases caused, exacerbated by or resulting from an excess of, or undesired activation of, platelets in a mammal, said compositions comprising a compound which non-selectively or selectively inhibits the activity of an anti-apoptotic Bcl-2 family protein member.

Another embodiment comprises methods of preventing or treating diseases caused, exacerbated by or resulting from an excess of, or undesired activation of, platelets in a mammal comprising administering thereto a compound which non-selectively or selectively inhibits the activity of an anti-apoptotic Bcl-2 family protein member, wherein the compound has an inhibitory potency ($IC_{50}$) of less than about 100 nanomolar, less than about 50 nanomolar, less than about 10 nanomolar or less than about 1 nanomolar.

DETAILED DESCRIPTION OF THE INVENTION

Series of antagonists of antiapoptotic Bcl-2 family protein members are disclosed in commonly-owned U.S. application Ser. No. 11/432,937 and U.S. application Ser. No. 11/491,851, the specifications of which are hereby incorporated by reference into this application. It has since been recognized that these agents display a unique thrombocytopenia characterized by rapid clearance of circulating platelets in mouse, rat and dog.

One embodiment of this invention comprises methods of preventing or treating diseases caused, exacerbated by or resulting from an excess of, or undesired activation of, platelets in a mammal comprising administering thereto a compound which non-selectively or selectively inhibits the activity of an anti-apoptotic Bcl-2 family protein member.

Another embodiment comprises methods of preventing or treating diseases caused, exacerbated by or resulting from an excess of or undesired activation of platelets in a mammal comprising administering thereto a compound which non-selectively or selectively inhibits the activity of an anti-apoptotic Bcl-2 family protein member, wherein the compound has an inhibitory potency ($IC_{50}$) of less than about 100 nanomolar, less than about 50 nanomolar, less than about 10 nanomolar or less than about 1 nanomolar.

Still another embodiment comprises methods of reducing the number of platelets in mammals and preventing or treating pro-thrombotic conditions and diseases that are characterized by an excess of, or undesired activation of, platelets.

Still another embodiment comprises methods of preventing or treating essential thrombocythemia in a mammal comprising administering thereto a compound which non-selectively or selectively inhibits the activity of an anti-apoptotic Bcl-2 family protein member.

Still another embodiment comprises methods of preventing or treating essential thrombocythemia in a mammal comprising administering thereto a compound which non-selectively or selectively inhibits the activity of an anti-apoptotic Bcl-2 family protein member, wherein the compound has an inhibitory potency ($IC_{50}$) of less than about 100 nanomolar, less than about 50 nanomolar, less than about 10 nanomolar or less than about 1 nanomolar.

Still another embodiment comprises methods of reducing the number of platelets in a mammal and preventing or treating essential thrombocythemia.

Still another embodiment comprises methods of preventing or treating essential thrombocythemia in a mammal comprising administering thereto N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide or N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment comprises methods of preventing or treating essential thrombocythemia in a mammal comprising administering thereto the compound N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide or the compound N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, wherein the compound has an inhibitory potency ($IC_{50}$) of less than about 100 nanomolar, less than about 50 nanomolar, less than about 10 nanomolar or less than about 1 nanomolar.

Still another embodiment comprises methods of reducing the number of platelets in a mammal and preventing or treating essential thrombocythemia.

Still another embodiment comprises methods of preventing or treating polycythemia vera in a mammal comprising administering thereto a compound which non-selectively or selectively inhibits the activity of an anti-apoptotic Bcl-2 family protein member.

Still another embodiment comprises methods of preventing or treating polycythemia vera in a mammal comprising administering thereto a compound which non-selectively or selectively inhibits the activity of an anti-apoptotic Bcl-2 family protein member, wherein the compound has an inhibitory potency ($IC_{50}$) of less than about 100 nanomolar, less than about 50 nanomolar, less than about 10 nanomolar or less than about 1 nanomolar.

Still another embodiment comprises methods of reducing the number of platelets in a mammal and preventing or treating polycythemia vera.

Still another embodiment comprises methods of preventing or treating polycythemia vera in a mammal comprising administering thereto N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide or N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment comprises methods of preventing or treating polycythemia vera in a mammal comprising administering thereto the compound N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide or the compound N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, wherein the compound has an inhibitory potency ($IC_{50}$) of less than about 100 nanomolar, less than about 50 nanomolar, less than about 10 nanomolar or less than about 1 nanomolar.

Still another embodiment comprises methods of reducing the number of platelets in a mammal and preventing or treating polycythemia vera.

As used herein, a "Bcl-2 protein family inhibitor" refers to a therapeutic compound of any type, including small molecule-, antibody-, antisense-, small interfering RNA-, or microRNA-based compounds, that binds to at least one of Bcl-2, Bcl-XL, and Bcl-w, or their corresponding mRNAs including untranslated regions, and antagonizes the activity of the Bcl-2 family related nucleic acid or protein. The inventive methods are useful with any known or hereafter developed Bcl-2 family inhibitor. Preferred Bcl-2 protein family inhibitors are N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide and N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, both of which are capable of binding to Bcl-2, Bcl-XL, and Bcl-w.

Diseases caused or exacerbated by an excess of, or undesired activation of, platelets include, but are not limited to, essential thrombocytopenia, polycythemia vera, M7 acute myelogenous leukemia, restenosis, cardiovascular disease, perioperative antiplatelet therapy, device-associated thrombi and complications associated therewith, and the like.

Involvement of platelets in essential thrombocythemia is reported in Seminars in Hematology (2005), 42(4), 230-238 and also in New Eng. J. Med., 2005, 353:1, 33-45.

Involvement of platelets in polycythemia vera is reported in Seminars in Thrombosis and Hemostatis (2006), 32(3), 267-275.

Involvement of platelets in restenosis is reported in Journal of Clinical Pathology (2006), 59(3), 232-239.

Involvement of platelets in cardiovascular disease is reported in International Journal of Clinical Practice (2003), 57(10), 898-905.

Involvement of platelets in perioperative antiplatelet therapy is reported in Journal of Thrombosis Thrombolysis.

Diseases or conditions that result from elevated platelet levels include bleeding, thrombosis or other thromboembolic complication, initiation or worsening of other diseases or disorders of the blood, such as "sticky platelet" syndrome.

Bcl-2 family protein members mean Bcl-2 protein and proteins having a structural homology thereto such as, for example, Bcl-$X_L$ and Bcl-w.

Compounds which inhibit the activity of Bcl-2 family protein members may do so non-selectively or selectively, wherein non-selective inhibitors bind to two or more than two Bcl-2 family protein members and selective inhibitors bind to one Bcl-2 family protein member preferentially over the other Bcl-2 family protein members.

Examples of non-selective and selective binders for the practice of this invention include, but are not limited to, compounds having formula (I)

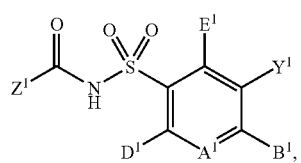

(I)

and therapeutically acceptable salts, prodrugs and salts of prodrugs thereof, wherein $A^1$ is N or $C(A^2)$;

one or two or three or each of $A^2$, $B^2$, $D^1$ and $E^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NR^1C(O)NHR^1$, $NR^1C(O)N(R^1)_2$, $SO_2NHR^1$, $SO_2N(R^1)_2$, $NHSO_2R^1$, $NHSO_2NHR^1$ or $N(CH_3)SO_2N(CH_3)R^1$, and the remainder are independently selected H, F, Cl, Br, I, CN, $CF_3$, C(O)OH, $C(O)NH_2$ or $C(O)OR^{1A}$; and $Y^1$ is H, CN, $NO_2$, C(O)OH, F, Cl, Br, I, $CF_3$, $OCF_3$, $CF_2CF_3$, $OCF_2CF_3$, $R^{17}$, $OR^{17}$, $C(O)R^{17}C(O)OR^{17}$, $SR^{17}$, $NH_2$, $NHR^{17}N(R^{17})_2$, $NHC(O)R^{17}C(O)NH_2$, $C(O)NHR^{17}C(O)N(R^{17})_2$, $NHS(O)R^{17}$ or $NHSO_2R^{17}$;

or
$B^1$ and $Y^1$, together with the atoms to which they are attached, are imidazole or triazole; and
one or two or each of $A^2$, $D^1$ and $E^1$ are independently selected H, $R^1OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NHC(O)NHR^1$, $N(CH_3)C(O)N(CH_3)R^1$, $SO_2NHR^1SO_2N(R^1)_2$, $NHSO_2R^1NHSO_2NHR^1$ or $N(CH_3)SO_2N(CH_3)R^1$ and the remainder are independently selected H, F, Cl, Br, I, $CF_3$, C(O)OH, $C(O)NH_2$ or $C(O)OR^{1A}$;

$R^1$ is $R^2R^3$, $R^4$ or $R^5$;

$R^{1A}$ is $C_1$-$C_6$-alkyl, $C_3$-$C_6$-alkenyl or $C_3$-$C_6$-alkynyl;

$R^2$ is phenyl which is unfused or fused with benzene, heteroarene or $R^{2A}$; $R^{2A}$ is cycloalkane or heterocycloalkane;

$R^3$ is heteroaryl which is unfused or fused with benzene, heteroarene or $R^{3A}$; $R^{3A}$ is cycloalkane or heterocycloalkane;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, $NC(R^{6A})(R^{6B})$, $R^7$, $OR^7$, $SR^7$, $S(O)R^7$, $SO_2R^7NHR^7$, $N(R^7)_2$, $C(O)R^7$, $C(O)NH_2$, $C(O)NHR^7$, $NHC(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), C(O)OH, $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl which is unfused or fused with benzene, heteroarene or $R^{8A}$;

$R^{8A}$ is phenyl which is unfused or fused with benzene, heteroarene or $R^{8A}$; $R^{8A}$ is cycloalkane, cycloalkene, heterocycloalkane or heterocycloalkene;

$R^9$ is heteroaryl which is unfused or fused with benzene, heteroarene or $R^{9A}$; $R^{9A}$ is cycloalkane, cycloalkene, heterocycloalkane or heterocycloalkene;

$R^{10}$ is $C_3$-$C_{10}$-cycloalkyl, $C_4$-$C_{10}$-cycloalkenyl, $C_3$-$C_{10}$-heterocycloalkyl or $C_4$-$C_{10}$-heterocycloalkenyl, each of which is unfused or fused with cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $NHR^{12}$, $N(R^{12})_2$, $C(O)NH_2$, $C(O)NHR^{12}C(O)N(R^{12})_2$, OH, (O), C(O)OH, $N_3$, CN, $NH_2$, $CF_3$, $CF_2CF_3$, F, Cl, Br or I substituents;

$R^{12}$ is $R^{13}$, $R^{14}$, $R^{15}$ or $R^{16}$;

$R^{13}$ is phenyl which is unfused or fused with benzene, heteroarene or $R^{13A}$; $R^{13A}$ is cycloalkane, cycloalkene, heterocycloalkane or heterocycloalkane;

$R^{14}$ is heteroaryl, each of which is unfused or fused with benzene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkynyl;

$R^{17}$ is $R^{18}$, or $R^{19}$, $R^{20}$ or $R^{21}$;

$R^{18}$ is phenyl which is unfused or fused with benzene, heteroarene or $R^{18A}$; $R^{18A}$ is cycloalkane, cycloalkene, heterocycloalkane or heterocycloalkene;

$R^{19}$ is heteroaryl which is unfused or fused with benzene, heteroarene or $R^{19A}$; $R^{19A}$ is cycloalkane, cycloalkene, heterocycloalkane or heterocycloalkene;

$R^{20}$ is $C_3$-$C_{10}$-cycloalkyl or $C_4$-$C_{10}$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{20A}$; $R^{20A}$ is cycloalkane, cycloalkene, heterocycloalkane or heterocycloalkene;

$R^{21}$ is alkyl, alkenyl or alkynyl, each of which is unsubstituted or substituted with one or two or three independently selected $R^{22}$, $OR^{22}$, $NHR^{22}$, $N(R^{22})_2$, $C(O)NH_2$, $C(O)NHR^{22}$, $C(O)N(R^{22})_2$, OH, (O), C(O)OH, $N_3$, CN, $NH_2$, $CF_3$, $CF_2CF_3$, F, Cl, Br or I substituents;

$R^{22}$ is $R^{23}$, $R^{24}$, $R^{25}$;

$R^{23}$ is phenyl which is unfused or fused with benzene, heteroarene or $R^{3A}$; $R^{23A}$ is cycloalkane, cycloalkene, heterocycloalkane or heterocycloalkene;

$R^{24}$ is heteroarene which is unfused or fused with benzene, heteroarene or $R^{24A}$; $R^{24A}$ is cycloalkane, cycloalkene, heterocycloalkane or heterocycloalkene;

$R^{25}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{25A}$; $R^{5A}$ is cycloalkane, cycloalkene, heterocycloalkane or heterocycloalkene;

$Z^1$ is $R^{26}$ or $R^{27}$, each of which is substituted with $R^{28}$, $R^{29}$ or $R^{30}$, each of which is substituted with F, Cl, Br, I, $CH_2R^{37}$, $CH(R^{31})(R^{37})$, $C(R^{31})(R^{31A})(R^{37})$, $C(O)R^{37}$, $OR^{37}SR^{37}$, $S(O)R^{37}$, $SO_2R^{37}$, $NHR^{37}$ or $N(R^{32})R^{37}$;

$R^{26}$ is phenyl which is unfused or fused with benzene or heteroarene;

$R^{27}$ is heteroarene which is unfused or fused with benzene or heteroarene;

$R^{28}$ is phenyl which is unfused or fused with benzene, heteroarene or $R^{28A}$; $R^{28A}$ is cycloalkane, cycloalkene, heterocycloalkane or heterocycloalkene $R^{29}$ is heteroaryl or $R^{29A}$; $R^{29A}$ is cycloalkane, cycloalkene, heterocycloalkane or heterocycloalkene;

$R^{30}$ is cycloalkyl or cycloalkenyl, heterocycloalkyl or heterocycloalkenyl, each of which is unfused or fused with a benzene, heteroarene or $R^{30A}$; $R^{30A}$ is cycloalkane, cycloalkene, heterocycloalkane or heterocycloalkene;

$R^{31}$ and $R^{31A}$ are independently F, Cl, Br or alkyl or are taken together and are $C_2$-$C_5$-spiroalkyl;

$R^{32}$ is $R^{33}$, $C(O)R^{33}$ or $C(O)OR^{33}$;

$R^{33}$ is $R^{34}$ or $R^{35}$, $R^{34}$ is phenyl which is unfused or fused with aryl, heteroaryl or $R^{34A}$; $R^{34A}$ is cycloalkane, cycloalkene, heterocycloalkane or heterocycloalkene;

$R^{35}$ is alkyl which is unsubstituted or substituted with $R^{36}$;

$R^{36}$ is phenyl which is unfused or fused with benzene, heteroarene or $R^{36A}$; $R^{36A}$ is cycloalkane, cycloalkene, heterocycloalkane or heterocycloalkene;

$R^{37}$ is $R^{38}$, $R^{39}$ or $R^{40}$, each of which is substituted with F, Cl, Br, I, $R^{41}$, $OR^{41}$, $NHR^{41}$, $N(R^{41})_2$, $NHC(O)OR^{41}$, $SR^{41}$, $S(O)R^{41}$ or $SO_2R^{41}$;

$R^{38}$ is phenyl which is unfused or fused with benzene, heteroarene or $R^{38A}$; $R^{38A}$ is cycloalkane, cycloalkene, heterocycloalkane or heterocycloalkene;

$R^{39}$ is heteroaryl which is unfused or fused with benzene, heteroarene or $R^{39A}$; $R^{39A}$ is cycloalkane, cycloalkene, heterocycloalkane or heterocycloalkene;

$R^{40}$ is $C_3$-$C_8$-cycloalkyl or $C_4$-$C_8$-cycloalkenyl, $C_3$-$C_8$-heterocycloalkyl or $C_3$-$C_8$-cycloalkenyl, each of which is unfused or fused with benzene, heteroarene or $R^{40A}$; $R^{40A}$ cycloalkane, cycloalkene, heterocycloalkane or heterocycloalkene;

$R^{41}$ is $R^{42}$, $R^{43}$, $R^{44}$ or $R^{45}$;

$R^{42}$ is phenyl which is unfused or fused with benzene, heteroarene or $R^{42A}$; $R^{42A}$ is cycloalkane, cycloalkene, heterocycloalkane or heterocycloalkene;

$R^{43}$ is heteroaryl which is unfused or fused with benzene, heteroarene or $R^{43A}$; $R^{43A}$ is cycloalkane, cycloalkene, heterocycloalkane or heterocycloalkene;

$R^{44}$ is $C_3$-$C_6$-cycloalkyl or $C_4$-$C_6$-cycloalkenyl, $C_3$-$C_6$-heterocycloalkyl or $C_4$-$C_6$-heterocycloalkenyl, each of which is unfused or fused with benzene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $NHR^{46}$, $N(R^{46})_2$, $C(O)NH_2$, $C(O)NHR^{46}$, $C(O)N(R^{46})_2$, OH, (O), C(O)OH, $N_3$, CN, $NH_2$, $CF_3$, $CF_2CF_3$, F, Cl, Br or I substituents;

$R^{46}$ is $R^{47}$, $R^{48}$ or $R^{49}$;

$R^{47}$ is phenyl which is unfused or fused with benzene, heteroarene or $R^{47A}$; $R^{47A}$ is cycloalkane, cycloalkene, heterocycloalkane or heterocycloalkene;

$R^{48}$ is heteroaryl or $R^{48A}$; $R^{48}$ is cycloalkane, cycloalkene, heterocycloalkane or heterocycloalkene;

$R^{49}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, heteroarene or $R^{49A}$; $R^{49A}$ is cycloalkane, cycloalkene, heterocycloalkane or heterocycloalkene;

wherein each foregoing cyclic moiety is independently unsubstituted, further unsubstituted, substituted or further substituted with one or two or three or four or five independently selected $R^{50}$, $OR^{50}SR^{50}S(O)R^{50}$, $SO_2R^{50}$, $C(O)R^{50}$, $CO(O)R^{50}$, $OC(O)R^{50}$, $OC(O)OR^{50}$, $NH_2$, $NHR^{50}$, $N(R^{50})_2$, $C(O)NH_2$, $C(O)NHR^{50}$, $C(O)N(R^{50})_2$, $C(O)NHOH$, $C(O)NHOR^{50}$, $C(O)NHSO_2R^{50}C(O)NR^{55}SO_2R^{50}$, $SO_2NH_2$, $SO_2NHR^{50}SO_2N(R^{50})_2$, $CF_3$, $CF_2CF_3$, C(O)H, C(O)OH, $C(N)NH_2$, $C(N)NHR^{50}$, $C(N)N(R^{50})_2$, OH, (O), $N_3$, $NO_2$, $CF_3$, $CF_2CF_3$, $OCF_3$, $OCF_2CF_3$, F, Cl, Br or I substituents;

$R^{50}$ is $R^{51}$, $R^{52}$, $R^{53}$ or $R^{54}$;

$R^{51}$ is phenyl which is unfused or fused with benzene, heteroarene or $R^{51A}$; $R^{51A}$ is cycloalkane, cycloalkene, heterocycloalkane or heterocycloalkene;

$R^{52}$ is heteroaryl or $R^{52A}$; $R^{52A}$ is cycloalkane, cycloalkene, heterocycloalkane or heterocycloalkene;

$R^{53}$ is $C_3$-$C_6$-cycloalkyl, $C_4$-$C_6$-cycloalkenyl, $C_3$-$C_6$-heterocycloalkyl, or $C_4$-$C_6$-cycloalkenyl, each of which is unfused or fused with benzene, heteroarene or $R^{53A}$; $R^{53A}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}SO_2R^{55}$, $NHR^{55}$, $N(R^{55})_2$, $C(O)R^{55}$, $C(O)NH_2$, $C(O)NHR^{55}$, $NHC(O)R^{55}NHSO_2R^{55}$ $R^{55}$ $NHC(O)OR^{55}S_2NH_2$, $SO_2NHR^{55}$, $SO_2N(R^{55})_2$, NHC (O)NH$_2$, NHC(O)NHR$^{55}$, OH, (O), C(O)OH, (O), N$_3$, CN, NH$_2$, CF$_3$, OCF$_3$, CF$_2$CF$_3$, OCF$_2$CF$_3$, F, Cl, Br or I substituents;

R$^{55}$ is alkyl, alkenyl, alkynyl, phenyl, heteroaryl, C$_3$-C$_6$-cycloalkyl, C$_4$-C$_6$-cycloalkenyl, C$_3$-C$_6$-heterocycloalkyl, or C$_4$-C$_6$-cycloalkenyl.

Preferred compounds of formula (I) are compounds having formula (I)-a (I)-a and therapeutically acceptable salts, prodrugs and salts of prodrugs thereof, wherein R$^{5a}$ is hydrogen, alkyl, alkenyl or alkynyl, each of which is unsubstituted or substituted with one or two or three independently selected R$^6$ NC(R$^{6A}$)(R$^{6B}$), R$^7$OR$^7$, SR$^7$, S(O)R$^7$, SO$_2$R$^7$, NHR$^7$, N(R$^7$)$_2$, C(O)R$^7$, C(O)NH$_2$, C(O)NHR$^7$, NHC(O)R$^7$, NHSO$_2$R$^7$, NHC(O)OR$^7$SO$_2$NH$_2$, SO$_2$NHR$^7$, SO$_2$N(R$^7$)$_2$, NHC(O)NH$_2$, NHC(O)NHR$^7$, OH, (O), C(O)OH, (O), N$_3$, CN, NH$_2$, CF$_3$, CF$_2$CF$_3$, F, Cl, Br or I substituents.

Representative compounds for the practice of this invention include, but are not limited to, N-(4-(4-((1,1'-biphenyl)-2-ylmethyl)piperazin-1-yl)benzoyl)-4-(((1R)-3-(dimethylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-((4'-methoxy(1,1'-biphenyl)-2-yl)methyl)piperazin-1-yl)benzoyl)-3-nitrobenzenesulfonamide, 4-(((1R)-3-(dimethylamino)-1-((phenylsulfanyl)methyl)propyl)amino)-N-(4-(4-((4'-fluoro(1,1'-biphenyl)-2-yl)methyl)piperazin-1-yl)benzoyl)-3-nitrobenzenesulfonamide, 4-(((1R)-3-(dimethylamino)-1-((phenylsulfanyl)methyl)propyl)amino)-N-(4-(4-((4'-(methylsulfanyl)(1,1'-biphenyl)-2-yl)methyl)piperazin-1-yl)benzoyl)-3-nitrobenzenesulfonamide, N-((4-(((1R)-3-(dimethylamino)-1-((phenylsulfanyl)methyl)propyl)amino)-3-nitrophenyl)sulfonyl)-4-(4-(4'-phenyl-1,1'-biphenyl-2-ylmethyl)piperazin-1-yl)benzamide, 4-(((1R)-3-(dimethylamino)-1-((phenylsulfanyl)methyl)propyl)amino)-3-nitro-N-(4-(4-((4'-phenoxy(1,1'-biphenyl)-2-yl)methyl)piperazin-1-yl)benzoyl)benzenesulfonamide, N-(4-(4-((1,1'-biphenyl)-2-ylmethyl)piperazin-1-yl)benzoyl)-4-((1,1-dimethyl-2-(phenylsulfanyl)ethyl)amino)-3-nitrobenzenesulfonamide, N-(4-(4-((1,1'-biphenyl)-2-ylmethyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((1,1'-biphenyl)-2-ylmethyl)piperazin-1-yl)benzoyl)-3-nitro-4-((2-(phenylsulfanyl)ethyl)amino)benzenesulfonamide, N-(4-(4-((4'-chloro(1,1'-biphenyl)-2-yl)methyl)piperazin-1-yl)benzoyl)-3-nitro-4-((2-(phenylsulfanyl)ethyl)amino)benzenesulfonamide, N-(4-(4-((4'-chloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-((1,1-dimethyl-2-(phenylsulfanyl)ethyl)amino)-3-nitrobenzenesulfonamide, N-(4-(4-((4'-chloro(1,1'-biphenyl)-2-yl)methyl)piperazin-1-yl)benzoyl)-4-(((1R)-4-(dimethylamino)-1-((phenylsulfanyl)methyl)butyl)amino)-3-nitrobenzenesulfonamide, N-(4-(4-((4'-chloro(1,1'-biphenyl)-2-yl)methyl)piperazin-1-yl)benzoyl)-4-(((1R)-5-(dimethylamino)-1-((phenylsulfanyl)methyl)pentyl)amino)-3-nitrobenzenesulfonamide, N-(4-(4-((4'-fluoro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro-4-fluoro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyrrolidin-1-yl)propyl)amino)benzenesulfonamide, N-(4-(4-((4'-chloro(1,1'-biphenyl)-2-yl)methyl)piperazin-1-yl)benzoyl)-4-((1,1-dimethyl-2-(1,3-thiazol-2-ylsulfanyl)ethyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((1,3-thiazol-2-ylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((thien-2-ylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-2-(2-(dimethylamino)ethoxy)-1-((phenylsulfanyl)methyl)ethyl)amino)-3-nitrobenzenesulfonamide, N-(4-(4-((4'-chloro(1,1'-biphenyl)-2-yl)methyl)piperazin-1-yl)benzoyl)-4-(((1S)-3-(dimethylamino)-1-methyl-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(methylamino)-1-((phenylsulfanyl)methyl)propyl)amino)-3-nitrobenzenesulfonamide, (3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butanoic acid, (3R)-3-(4-(((4-(4-((4'-chloro(1,1'-biphenyl)-2-yl)methyl)piperazin-1-yl)benzoyl)amino)sulfonyl)-2-nitroanilino)-N-isopropyl-4-(phenylsulfanyl)butanamide, N-(4-(4-((4'-chloro(1,1'-biphenyl)-2-yl)methyl)piperazin-1-yl)benzoyl)-4-(((1R)-3-(diisopropylamino)-1-((phenylsulfanyl)methyl)propyl)amino)-3-nitrobenzenesulfonamide, 4-(((1R)-3-(azetidin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-((4-(phenylsulfanyl)tetrahydro-3-furanyl)amino)benzenesulfonamide, N-(4-(4-((4'-chloro(1,1'-biphenyl)-2-yl)methyl)-4-methoxypiperidin-1-yl)benzoyl)-4-(((1R)-3-(dimethylamino)-1-((phenylsulfanyl)methyl)propyl)amino)-3-nitrobenzenesulfonamide, N-(4-(4-((4'-chloro(1,1'-biphenyl)-2-yl)methyl)-4-methoxypiperidin-1-yl)benzoyl)-4-(((1R)-3-(morpholin-4-yl)-1-((phenylsulfanyl)methyl)propyl)amino)-3-nitrobenzenesulfonamide N-(4-(4-((4'-chloro(1,1'-biphenyl)-2-yl)methyl)piperazin-1-yl)benzoyl)-4-(((1R)-3-hydroxy-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(isopropylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-(2-(2-naphthyl)benzyl)piperazin-1-yl)benzoyl)-3-nitrobenzenesulfonamide, 4-(((1R)-3-(dimethylamino)-1-((phenylsulfanyl)methyl)propyl)amino)-N-(4-(4-(2-(1-naphthyl)benzyl)piperazin-1-yl)benzoyl)-3-nitrobenzenesulfonamide, N-(4-(4-((3'-cyano(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-((3'-methoxy(1,1'-biphenyl)-2-yl)methyl)piperazin-1-yl)benzoyl)-3-nitrobenzenesulfonamide, N-(4-(4-((3'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide N-(4-(4-((2'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-(2-(1,3-benzodioxol-5-yl)benzyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-3-nitro-N-(4-(4-(2-(3-thienyl)benzyl)piperazin-1-yl)benzoyl)benzenesulfonamide, 4-(((1R)-3-(dimethylamino)-1-((phenylsulfanyl)methyl)propyl)amino)-3-nitro-N-(4-(4-(2-(pyridin-3-yl)benzyl)piperazin-1-yl)benzoyl)benzenesulfonamide, 4-(((1R)-3-(dimethylamino)-1-((phenylsulfanyl)methyl)propyl)amino)-3-nitro-N-(4-(4-(2-(quinolin-8-yl)benzyl)piperazin-1-yl)benzoyl)benzenesulfonamide, N-(4-(4-(2-(1-benzofuran-2-yl)benzyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-((2'-methyl(1,1'-biphenyl)-2-yl)methyl)piperazin-1-yl)benzoyl)-3-nitrobenzenesulfonamide, 4-(((1R)-3-(dimethylamino)-1-((phenylsulfanyl)methyl)propyl)amino)-3-nitro-N-(4-(4-(2-(quinolin-3-yl)benzyl)piperazin-1-yl)benzoyl)benzenesulfonamide, N-(4-(4-((1-(4-chlorophenyl)-2-naphthyl)methyl)piperazin-1-yl)benzoyl)-3-nitro-4-((2-(phenylsulfanyl)ethyl)amino)benzenesulfonamide, N-(4-(4-((1-(4-chlorophenyl)-2-naphthyl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((1-(4-chlorophenyl)-2-naphthyl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-nitro-4-((2-(phenylsulfanyl)cyclopentyl)amino)benzenesulfonamide, N-(4-(4-((1,1'-biphenyl)-2-ylmethyl)-4-methoxypiperidin-1-yl)benzoyl)-3-nitro-4-((2-(phenylsulfanyl)cyclopentyl)amino)benzenesulfonamide, N-(4-(4-((4'-fluoro(1,1'-biphenyl)-2-yl)methyl)piperazin-1-yl)benzoyl)-3-nitro-4-((2-(phenylsulfanyl)ethyl)amino)benzenesulfonamide, N-(4-(4-((3',4'-dichloro(1,1'-biphenyl)-2-yl)methyl)piperazin-1-yl)benzoyl)-3-nitro-4-((2-(phenylsulfanyl)ethyl)amino)benzenesulfonamide, N-(4-(4-((3',4'-dichloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((3',4'-dichloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, 3-nitro-4-((2-(phenylsulfanyl)ethyl)amino)-N-(4-(4-((4'-(trifluoromethyl)(1,1'-biphenyl)-2-yl)methyl)piperazin-1-yl)benzoyl)benzenesulfonamide, 4-(((1R)-3-(dimethylamino)-1-((phenylsulfanyl)methyl)propyl)amino)-3-nitro-N-(4-(4-((4'-(trifluoromethyl)(1,1'-biphenyl)-2-yl)methyl)piperazin-1-yl)benzoyl)benzenesulfonamide, 4-(((1R)-3-(morpholin-4-yl)-1-((phenylsulfanyl)methyl)propyl)amino)-3-nitro-N-(4-(4-((4'-(trifluoromethyl)(1,1'-biphenyl)-2-yl)methyl)piperazin-1-yl)benzoyl)benzenesulfonamide, 3-nitro-4-((2-(phenylsulfanyl)ethyl)amino)-N-(4-(4-((4'-(trifluoromethoxy)(1,1'-biphenyl)-2-yl)methyl)piperazin-1-yl)benzoyl)benzenesulfonamide, 3-nitro-4-((2-(phenylsulfanyl)ethyl)amino)-N-(4-(4-((4'-(trifluoromethoxy)(1,1'-biphenyl)-2-yl)methyl)piperazin-1-yl)benzoyl)benzenesulfonamide, 4-(((1R)-3-(morpholin-4-yl)-1-((phenylsulfanyl)methyl)propyl)amino)-3-nitro-N-(4-(4-((4'-(trifluoromethoxy)(1,1'-biphenyl)-2-yl)methyl)piperazin-1-yl)benzoyl)benzenesulfonamide, 3-nitro-N-(4-(4-((4'-phenoxy(1,1'-biphenyl)-2-yl)methyl)piperazin-1-yl)benzoyl)-4-((2-(phenylsulfanyl)ethyl)amino)benzenesulfonamide, 4-(((1R)-3-(morpholin-4-yl)-1-((phenylsulfanyl)methyl)propyl)amino)-3-nitro-N-(4-(4-((4'-phenoxy(1,1'-biphenyl)-2-yl)methyl)piperazin-1-yl)benzoyl)benzenesulfonamide, N-(4-(4-((4'-chloro(1,1'-biphenyl)-2-yl)methyl)piperazin-1-yl)benzoyl)-4-(((1S)-3-(dimethylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-((1,1-dimethyl-2-(phenylsulfonyl)ethyl)amino)-3-nitrobenzenesulfonamide, N-(4-(4-((2',4'-dichloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-3-nitro-N-(4-(4-(2-(2-thienyl)benzyl)piperazin-1-yl)benzoyl)benzenesulfonamide, N-(4-(4-((4'-chloro-2'-methyl(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((2',4'-difluoro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((1,1'-biphenyl)-2-ylmethyl)piperazin-1-yl)benzoyl)-3-nitro-4-((2-(phenylsulfonyl)ethyl)amino)benzenesulfonamide, N-(4-(4-((4'-chloro(1,1'-biphenyl)-2-yl)methyl)piperazin-1-yl)benzoyl)-3-nitro-4-((2-(phenylsulfonyl)ethyl)amino)benzenesulfonamide, N-(4-(4-((1,1'-biphenyl)-2-ylmethyl)piperazin-1-yl)benzoyl)-3-nitro-4-((4-(phenylsulfanyl)tetrahydro-3-furanyl)amino)benzenesulfonamide, 4-(((1R)-3-(dimethylamino)-1-((phenylsulfanyl)methyl)propyl)amino)-N-(4-(4-(2-(5-methyl-2-thienyl)benzyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-((4-(phenylsulfonyl)tetrahydro-3-furanyl)amino)benzenesulfonamide, N-(4-(4-((1,1'-biphenyl)-2-ylmethyl)piperazin-1-yl)benzoyl)-3-nitro-4-((4-(phenylsulfonyl)tetrahydro-3-furanyl)amino)benzenesulfonamide, N-(4-(4-((4'-chloro(1,1'-biphenyl)-2-yl)methyl)piperazin-1-yl)benzoyl)-4-((1-methyl-4-(phenylsulfanyl)pyrrolidin-3-yl)amino)-3-nitrobenzenesulfonamide, N-(4-(4-((2-(4-chlorophenyl)-1-cyclohexen-1-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((2-(4-chlorophenyl)-1-cyclohexen-1-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-bromo(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-(1-(4'-chloro(1,1'-biphenyl)-2-yl)cyclopropyl)piperazin-1-yl)benzoyl)-4-(((1R)-3-(dimethylamino)-1-((phenylsulfanyl)methyl)propyl)amino)-3-nitrobenzenesulfonamide, N-(4-(4-((2-(4-chlorophenyl)-1-cyclohexen-1-yl)methyl)piperazin-1-yl)benzoyl)-4-(((1R)-2-(dimethylamino)-1-((phenylsulfanyl)methyl)ethyl)amino)-3-nitrobenzenesulfonamide, N-(4-(4-((4'-chloro(1,1'-biphenyl)-2-yl)methyl)piperazin-1-yl)benzoyl)-4-(((1R)-2-(dimethylamino)-1-((phenylsulfanyl)methyl)ethyl)amino)-3-nitrobenzenesulfonamide, N-(4-(4-((4'-chloro(1,1'-biphenyl)-2-yl)methyl)piperazin-1-yl)benzoyl)-4-(((1R)-2-(diethylamino)-1-((phenylsulfanyl)methyl)ethyl)amino)-3-nitrobenzenesulfonamide, N-(4-(4-((4'-chloro(1,1'-biphenyl)-2-yl)methyl)piperazin-1-yl)benzoyl)-4-(((1R)-2-(morpholin-4-yl)-1-((phenylsulfanyl)methyl)ethyl)amino)-3-nitrobenzenesulfonamide, N-(4-(4-((2-(4-chlorophenyl)-1-cyclohexen-1-yl)methyl)piperazin-1-yl)benzoyl)-4-(((1R)-2-(diethylamino)-1-((phenylsulfanyl)methyl)ethyl)amino)-3-nitrobenzenesulfonamide, N-(4-(4-((2-(4-chlorophenyl)-1-cyclohexen-1-yl)methyl)piperazin-1-yl)benzoyl)-4-(((1R)-2-(morpholin-4-yl)-1-((phenylsulfanyl)methyl)ethyl)amino)-3-nitrobenzenesulfonamide, N-(4-(4-((4'-chloro(1,1'-biphenyl)-2-yl)methyl)piperazin-1-yl)benzoyl)-4-(((1R)-3-(cyclopropyl(methyl)amino)-1-((phenylsulfanyl)methyl)propyl)amino)-3-nitrobenzenesulfonamide, N-(4-(4-((1,1'-biphenyl)-2-ylmethyl)-4-methoxypiperidin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-methoxy-4-(2-(pyridin-3-yl)benzyl)piperidin-1-yl)benzoyl)-3-nitrobenzenesulfonamide, 4-(((1R)-3-(dimethylamino)-1-((phenylsulfanyl)methyl)propyl)amino)-N-(4-(4-methoxy-4-(2-(pyridin-4-yl)benzyl)piperidin-1-yl)benzoyl)-3-nitrobenzenesulfonamide, 4-(((1R)-3-(dimethylamino)-1-((phenylsulfanyl)methyl)propyl)amino)-N-(4-(4-methoxy-4-(2-(2-thienyl)benzyl)piperidin-1-yl)benzoyl)-3-nitrobenzenesulfonamide, 4-(((1R)-3-(dimethylamino)-1-((phenylsulfanyl)methyl)propyl)amino)-N-(4-(4-methoxy-4-(2-(3-thienyl)benzyl)piperidin-1-yl)benzoyl)-3-nitrobenzenesulfonamide, 4-(((1R)-3-(azetidin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-((2,2,2-trifluoroethyl)amino)propyl)amino)benzenesulfonamide, N-(4-(4-((4'-chloro(1,1'-biphenyl)-2-yl)methyl)piperazin-1-yl)benzoyl)-4-(((1R)-3-(methyl(2,2,2-trifluoroethyl)amino)-1-((phenylsulfanyl)methyl)propyl)amino)-3-nitrobenzenesulfonamide, N-(4-(4-((4'-chloro(1,1'-biphenyl)-2-yl)methyl)-4-methoxypiperidin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)-4-methoxypiperidin-1-yl)benzoyl)-3-nitro-4-((2-(phenylsulfanyl)ethyl)amino)benzenesulfonamide, N-(4-(4-((4'-chloro(1,1'-biphenyl)-2-yl)methyl)piperazin-1-yl)benzoyl)-4-(((1R)-3-(ethyl(2,2,2-trifluoroethyl)amino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-((2-fluoroethyl)amino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-((2,2-difluoroethyl)amino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-1-((1R)-3-(dimethylamino)-1-((phenylsulfanyl)methyl)propyl)-1H-benzimidazole-5-sulfonamide, N-(4-(4-((4'-chloro(1,1'-biphenyl)-2-yl)methyl)piperazin-1-yl)benzoyl)-1-((1R)-3-(dimethylamino)-1-((phenylsulfanyl)methyl)propyl)-1H-1,2,3-benzotriazole-5-sulfonamide, 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)benzamide, N-(4-(4-((4'-(dimethylamino)(1,1'-biphenyl)-2-yl)carbonyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-((4'-(methylsulfanyl)(1,1'-biphenyl)-2-yl)carbonyl)piperazin-1-yl)benzoyl)-3-nitrobenzenesulfonamide, 4-(((1R)-3-(dimethylamino)-1-((phenylsulfanyl)methyl)propyl)amino)-N-(4-(4-((4'-(methylsulfonyl)(1,1'-biphenyl)-2-yl)carbonyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-cyano-4-(((1R)-3-(dimethylamino)-1-((phenylsulfanyl)methyl)propyl)amino)benzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)oxy)-3-nitrobenzenesulfonamide, N-(4-(4-((4'-chloro(1,1'-biphenyl)-2-yl)methyl)piperazin-1-yl)benzoyl)-4-(((1R)-3-(4,4-dimethyl-4,5-dihydro-1H-imidazol-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(5,6-dihydro-1(4H)-pyrimidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(2-methyl-4,5-dihydro-1H-imidazol-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(5,6-dihydro-1(4H)-pyrimidin-1-yl)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-3-(2,4-dimethyl-4,5-dihydro-1H-imidazol-1-yl)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-3-(2-methyl-4,5-dihydro-1H-imidazol-1-yl)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-3-(4,4-dimethyl-4,5-dihydro-1H-imidazol-1-yl)-1-((phenylsulfanyl)methyl)propyl)amino)-3-(trifluoromethyl)benzenesulfonamide, N-(4-(4-((2-(4-chlorophenyl)-1-cyclohexen-1-yl)methyl)piperazin-1-yl)benzoyl)-4-(((1R)-3-(dimethylamino)-1-((phenylsulfanyl)methyl)propyl)oxy)-3-(trifluoromethyl)benzenesulfonamide, N-(4-(4-((2-(4-chlorophenyl)cyclohept-1-en-1-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide, 4-(((1R)-3-(bis(2-methoxyethyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, 4-(((1R)-3-(bis(2-methoxyethyl)amino)-1-((phenylsulfanyl)methyl)propyl)amino)-N-(4-(4-((4'-chloro(1,1'-biphenyl)-2-yl)methyl)piperazin-1-yl)benzoyl)-3-(trifluoromethyl)benzenesulfonamide, 4-(((1R)-5-amino-1-((phenylsulfanyl)methyl)pentyl)amino)-N-(4-(4-((4'-chloro(1,1'-biphenyl)-4-yl)methyl)-1-piperazinyl)benzoyl)-3-nitrobenzenesulfonamide, N-(4-(4-((1,1'-biphenyl)-2-ylmethyl)piperazin-1-yl)benzoyl)-4-(((1R)-4-methyl-1-((phenylsulfanyl)methyl)pentyl)amino)-3-nitrobenzenesulfonamide, tert-butyl(5R)-5-(4-(((4-(4-((4'-chloro(1,1'-biphenyl)-2-yl)methyl)piperazin-1-yl)benzoyl)amino)sulfonyl)-2-nitroanilino)-6-(phenylsulfanyl)hexylcarbamate, 4-(((1R)-5-amino-1-((phenylsulfanyl)methyl)pentyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-4-(((1R)-5-((methylsulfonyl)amino)-1-((phenylsulfanyl)methyl)pentyl)amino)-3-nitrobenzenesulfonamide, 4-(((1R)-5-((aminocarbonyl)amino)-1-((phenylsulfanyl)methyl)pentyl)amino)-N-(4-(4-((4'-chloro(1,1'-biphenyl)-2-yl)methyl)piperazin-1-yl)benzoyl)-3-nitrobenzenesulfonamide, 4-(((1R)-3-(dimethylamino)-1-((phenylsulfanyl)methyl)propyl)amino)-N-(4-(4-(2-(methylsulfanyl)benzyl)piperazin-1-yl)benzoyl)-3-nitrobenzenesulfonamide, 4-(((1R)-3-(dimethylamino)-1-((phenylsulfanyl)methyl)propyl)amino)-N-(4-(4-(2-(methylsulfonyl)benzyl)piperazin-1-yl)benzoyl)-3-nitrobenzenesulfonamide, 4-(((1R)-3-(dimethylamino)-1-((phenylsulfanyl)methyl)propyl)amino)-N-(4-(4-(2-(5,5-dimethyl-2-oxo-1,3-oxazolidin-3-yl)benzyl)piperazin-1-yl)benzoyl)-3-nitrobenzenesulfonamide, N-(4-(4-(2-cyclohexylbenzyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-(2-(morpholin-4-yl)benzyl)piperazin-1-yl)benzoyl)-3-nitrobenzenesulfonamide, 4-(((1R)-3-(dimethylamino)-1-((phenylsulfanyl)methyl)propyl)amino)-N-(4-(4-(2-(isopropylsulfanyl)benzyl)piperazin-1-yl)benzoyl)-3-nitrobenzenesulfonamide, N-(4-(4-((2-(4-chlorophenyl)-1-cyclohexen-1-yl)methyl)piperazin-1-yl)benzoyl)-4-(((1R)-3-(isopropyl(methyl)amino)-1-((phenylsulfanyl)methyl)propyl)amino)-3-nitrobenzenesulfonamide, N-(4-(4-((2-(4-chlorophenyl)-1-cyclohexen-1-yl)methyl)piperazin-1-yl)benzoyl)-4-(((1R)-3-(dipropylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dipropylamino)-1-((phenylsulfanyl)methyl)propyl)amino)-3-nitrobenzenesulfonamide, N-(4-(4-((2-(4-chlorophenyl)-1-cyclohexen-1-yl)methyl)piperazin-1-yl)benzoyl)-4-(((1R)-3-(diethylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(diethylamino)-1-((phenylsulfanyl)methyl)propyl)amino)-3-nitrobenzenesulfonamide, N-(4-(4-((1,1'-biphenyl)-3-ylmethyl)piperazin-1-yl)benzoyl)-3-nitro-4-((2-(phenylsulfanyl)ethyl)amino)benzenesulfonamide, N-(4-(4-((1,1'-biphenyl)-3-ylmethyl)piperazin-1-yl)benzoyl)-4-(((1R)-3-(dimethylamino)-1-((phenylsulfanyl)methyl)propyl)amino)-3-nitrobenzenesulfonamide, N-(4-(4-((1,1'-biphenyl)-3-ylmethyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((1,1'-biphenyl)-2-ylmethyl)piperazin-1-yl)-3-fluorobenzoyl)-4-(((1R)-3-(dimethylamino)-1-((phenylsulfanyl)methyl)propyl)amino)-3-nitrobenzenesulfonamide, N-(4-(4-((1,1'-biphenyl)-2-ylmethyl)piperazin-1-yl)-3-fluorobenzoyl)-3-nitro-4-((2-(phenylsulfanyl)ethyl)amino)benzenesulfonamide, N-(4-(4-((1,1'-biphenyl)-2-ylmethyl)piperazin-1-yl)-3-fluorobenzoyl)-4-(((1R)-3-(morpholin-4-yl)-1-((phenylsulfanyl)methyl)propyl)amino)-3-nitrobenzenesulfonamide, N-(4-(4-((1,1'-biphenyl)-2-ylmethyl)piperazin-1-yl)-3,5-difluorobenzoyl)-4-(((1R)-3-(dimethylamino)-1-((phenylsulfanyl)methyl)propyl)amino)-3-nitrobenzenesulfonamide N-(4-(4-((1,1'-biphenyl)-2-ylmethyl)piperazin-1-yl)-3,5-difluorobenzoyl)-3-nitro-4-((2-(phenylsulfanyl)ethyl)amino)benzenesulfonamide, N-(4-(4-((1,1'-biphenyl)-2-ylmethyl)piperazin-1-yl)-3,5-difluorobenzoyl)-4-(((1R)-3-(morpholin-4-yl)-1-((phenylsulfanyl)methyl)propyl)amino)-3-nitrobenzenesulfonamide, 3-nitro-N-(4-(4-((1-phenyl-1H-imidazol-2-yl)methyl)piperazin-1-yl)benzoyl)-4-((2-(phenylsulfanyl)ethyl)amino)benzenesulfonamide, 4-(((1R)-3-(morpholin-4-yl)-1-((phenylsulfanyl)methyl)propyl)amino)-3-nitro-N-(4-(4-((1-phenyl-1H-imidazol-2-yl)methyl)piperazin-1-yl)benzoyl)benzenesulfonamide, 3-nitro-N-(4-(4-((1-phenyl-1H-pyrazol-5-yl)methyl)piperazin-1-yl)benzoyl)-4-((2-(phenylsulfanyl)ethyl)amino)benzenesulfonamide, 4-(((1R)-3-(morpholin-4-yl)-1-((phenylsulfanyl)methyl)propyl)amino)-3-nitro-N-(4-(4-((1-phenyl-1H-pyrazol-5-yl)methyl)piperazin-1-yl)benzoyl)benzenesulfonamide, 4-(((1R)-3-(morpholin-4-yl)-1-((phenylsulfanyl)methyl)propyl)amino)-3-nitro-N-(4-(4-((1-phenyl-1H-pyrazol-5-yl)methyl)piperazin-1-yl)benzoyl)benzenesulfonamide 4-(((1R)-3-(morpholin-4-yl)-1-((phenylsulfanyl)methyl)propyl)amino)-3-nitro-N-(4-(4-((1-phenyl-1H-imidazol-5-yl)methyl)piperazin-1-yl)benzoyl)benzenesulfonamide, 1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-3-azetidinecarboxylic acid, N-(4-(4-((4'-chloro(1,1'-biphenyl)-2-yl)methyl)piperazin-1-yl)benzoyl)-4-(((1R)-3-((2-hydroxy-2-methylpropyl)amino)-1-((phenylsulfanyl)methyl)propyl)amino)-3-nitrobenzenesulfonamide, (((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)(methyl)amino)acetic acid, (2R)-1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-2-pyrrolidinecarboxylic acid 1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-4-piperidinecarboxylic acid N-(4-(4-((4'-chloro(1,1'-biphenyl)-2-yl)methyl)piperazin-1-yl)benzoyl)-4-(((1R)-3-((2-hydroxyethyl)(methyl)amino)-1-((phenylsulfanyl)methyl)propyl)amino)-3-nitrobenzenesulfonamide, (2S)-1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-2-pyrrolidinecarboxylic acid, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(3-(2H-tetrazol-5-yl)azetidin-1-yl)propyl)amino)benzenesulfonamide, (2S)-2-amino-N-((1S)-2-(((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)amino)-1-methyl-2-oxoethyl)propanamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(2-(2H-tetrazol-5-yl)pyrrolidin-1-yl)propyl)amino)benzenesulfonamide, N-(4-(4-((4'-chloro(1,1'-biphenyl)-2-yl)methyl)piperazin-1-yl)benzoyl)-4-(((1R)-3-(4-(((methylsulfonyl)amino)carbonyl)piperidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)benzenesulfonamide, 1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-N-hydroxy-4-piperidinecarboxamide, 2-chloro-N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)benzenesulfonamide, 2,6-dichloro-N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)benzenesulfonamide, 4-(((1R)-3-((1R,5S)-8-azabicyclo[3.2.1]oct-8-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, 4-(((1R)-3-(7-azabicyclo[2.2.1]hept-7-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-(2-(phenylsulfanyl)ethoxy)benzenesulfonamide, N-(4-(4-((4'-chloro(1,1'-biphenyl)-2-yl)methyl)piperazin-1-yl)benzoyl)-4-(2-(phenylsulfanyl)ethoxy)-3-(trifluoromethyl)benzenesulfonamide, N-(4-(4-((4'-chloro(1,1'-biphenyl)-2-yl)methyl)piperazin-1-yl)benzoyl)-3-nitro-4-(((1R)-3-((1S,4S)-2-oxa-5-azabicyclo[2.2.1]hept-5-yl)-1-((phenylsulfanyl)methyl)propyl)amino)benzenesulfonamide, N-(4-(4-((4'-chloro(1,1'-biphenyl)-2-yl)methyl)piperazin-1-yl)benzoyl)-3-nitro-4-(((1R)-3-((1R,4R)-2-oxa-5-azabicyclo[2.2.1]hept-5-yl)-1-((phenylsulfanyl)methyl)propyl)amino)benzenesulfonamide, N-(4-(4-((2-(4-chlorophenyl)-1-cyclohexen-1-yl)methyl)piperazin-1-yl)benzoyl)-3-nitro-4-(((1R)-3-((1S,4S)-2-oxa-5-azabicyclo[2.2.1]hept-5-yl)-1-((phenylsulfanyl)methyl)propyl)amino)benzenesulfonamide, N-(4-(4-((2-(4-chlorophenyl)-1-cyclohexen-1-yl)methyl)piperazin-1-yl)benzoyl)-3-nitro-4-(((1R)-3-((1R,4R)-2-oxa-5-azabicyclo[2.2.1]hept-5-yl)-1-((phenylsulfanyl)methyl)propyl)amino)benzenesulfonamide, 4-(((1R)-3-(7-azabicyclo[2.2.1]hept-7-yl)-1-((phenylsulfanyl)methyl)propyl)amino)-N-(4-(4-((2-(4-chlorophenyl)-1-cyclohexen-1-yl)methyl)piperazin-1-yl)benzoyl)-3-nitrobenzenesulfonamide, N-(4-(4-((2-(4-chlorophenyl)-1-cyclohexen-1-yl)methyl)piperazin-1-yl)benzoyl)-4-(((1R)-3-((2R,5S)-2,5-dimethylpyrrolidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-nitro-4-(((1R)-3-((1R,4R)-2-oxa-5-azabicyclo[2.2.1]hept-5-yl)-1-((phenylsulfanyl)methyl)propyl)amino)benzenesulfonamide, N-(4-(4-((1,1'-biphenyl)-2-ylmethyl)piperazin-1-yl)benzoyl)-4-(cyclohexyloxy)-3-nitrobenzenesulfonamide, N-(4-(4-((1,1'-biphenyl)-2-ylmethyl)piperazin-1-yl)benzoyl)-4-(cyclohexylmethoxy)-3-nitrobenzenesulfonamide, N-(4-(4-((1,1'-biphenyl)-2-ylmethyl)piperazin-1-yl)benzoyl)-4-(2-cyclohexylethoxy)-3-nitrobenzenesulfonamide, N-(4-(4-((1,1'-biphenyl)-2-ylmethyl)piperazin-1-yl)benzoyl)-3-nitro-4-(tetrahydro-2H-pyran-4-ylamino)benzenesulfonamide, N-(4-(4-((1,1'-biphenyl)-2-ylmethyl)piperazin-1-yl)benzoyl)-4-((2-cyclohexylethyl)amino)-3-nitrobenzenesulfonamide, N-(4-(4-((1,1'-biphenyl)-2-ylmethyl)piperazin-1-yl)benzoyl)-4-(cyclohexyl(methyl)amino)-3-nitrobenzenesulfonamide, N-(4-(4-((1,1'-biphenyl)-2-ylmethyl)piperazin-1-yl)benzoyl)-4-(4,4-dimethylpiperidin-1-yl)-3-nitrobenzenesulfonamide, tert-butyl 4-(4-(((4-(4-((1,1'-biphenyl)-2-ylmethyl)piperazin-1-yl)benzoyl)amino)sulfonyl)-2-nitrophenoxy)-1-piperidinecarboxylate, N-(4-(4-((1,1'-biphenyl)-2-ylmethyl)piperazin-1-yl)benzoyl)-3-nitro-4-(piperidin-4-yloxy)benzenesulfonamide, N-(4-(4-((1,1'-biphenyl)-2-ylmethyl)piperazin-1-yl)benzoyl)-4-((1-methylpiperidin-4-yl)oxy)-3-nitrobenzenesulfonamide, N-(4-(4-((4'-chloro(1,1'-biphenyl)-2-yl)methyl)piperazin-1-yl)benzoyl)-4-((cyclohexylmethyl)amino)-3-nitrobenzenesulfonamide, N-(4-(4-((4'-chloro(1,1'-biphenyl)-2-yl)methyl)piperazin-1-yl)benzoyl)-4-((cyclohexylmethyl)(propyl)amino)-3-nitrobenzenesulfonamide, 4-(((1-benzylpiperidin-4-yl)methyl)amino)-N-(4-(4-((1,1'-biphenyl)-2-ylmethyl)piperazin-1-yl)benzoyl)-3-nitrobenzenesulfonamide, N-(4-(4-((1,1'-biphenyl)-2-ylmethyl)piperazin-1-yl)benzoyl)-4-((cyclohexylmethyl)(methyl)amino)-3-nitrobenzenesulfonamide, 4-((1-benzylpiperidin-4-yl)amino)-N-(4-(4-((1,1'-biphenyl)-2-ylmethyl)piperazin-1-yl)benzoyl)-3-nitrobenzenesulfonamide, N-(4-(4-((1,1'-biphenyl)-2-ylmethyl)piperazin-1-yl)benzoyl)-3-nitro-4-(tetrahydro-2H-sulfanylpyran-4-ylamino)benzenesulfonamide, ethyl 4-(4-(((4-(4-((1,1'-biphenyl)-2-ylmethyl)piperazin-1-yl)benzoyl)amino)sulfonyl)-2-nitroanilino)-1-piperidinecarboxylate, N-(4-(4-((1,1'-biphenyl)-2-ylmethyl)piperazin-1-yl)benzoyl)-3-nitro-4-(((1-propylpiperidine-4-yl)methyl)amino)benzenesulfonamide, N-(4-(4-((1,1'-biphenyl)-2-ylmethyl)piperazin-1-yl)benzoyl)-4-(isopropylamino)-3-nitrobenzenesulfonamide, N-(4-(4-((1,1'-biphenyl)-2-ylmethyl)piperazin-1-yl)benzoyl)-3-nitro-4-((2-(1,3-thiazol-2-ylsulfanyl)ethyl)amino)benzenesulfonamide, N-(4-(4-((1,1'-biphenyl)-2-ylmethyl)piperazin-1-yl)benzoyl)-3-nitro-4-((2-((4-phenyl-1,3-thiazol-2-yl)sulfanyl)ethyl)amino)benzenesulfonamide, 4-((2-(1,3-benzothiazol-2-ylsulfanyl)ethyl)amino)-N-(4-(4-((1,1'-biphenyl)-2-ylmethyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-((2-(1,3-thiazol-2-ylsulfanyl)ethyl)amino)benzenesulfonamide, 4-((2-(1,3-benzoxazol-2-ylsulfanyl)ethyl)amino)-N-(4-(4-((4'-chloro(1,1'-biphenyl)-2-yl)methyl)piperazin-1-yl)benzoyl)-3-nitrobenzenesulfonamide, 4-((2-(1,3-benzothiazol-2-ylsulfanyl)ethyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-((2-(pyrimidin-2-ylsulfanyl)ethyl)amino)benzenesulfonamide, 4-(((1R)-3-(morpholin-4-yl)-1-((phenylsulfanyl)methyl)propyl)amino)-3-nitro-N-(4-(4-((1-phenyl-1H-pyrazol-5-yl)methyl)piperazin-1-yl)benzoyl)benzenesulfonamide, 4-(((1-benzylpiperidin-4-yl)methyl)amino)-N-(4-(4-((4'-chloro(1,1'-biphenyl)-2-yl)methyl)piperazin-1-yl)benzoyl)-3-nitrobenzenesulfonamide, N-(4-(4-((1,1'-biphenyl)-2-ylmethyl)piperazin-1-yl)benzoyl)-4-((2-bromoethyl)amino)-3-nitrobenzenesulfonamide, N-(4-(4-((4'-chloro(1,1'-biphenyl)-2-yl)methyl)piperazin-1-yl)benzoyl)-4-((2-((4-methyl-1,3-thiazol-2-yl)sulfanyl)ethyl)amino)-3-nitrobenzenesulfonamide, N-(4-(4-((4'-chloro(1,1'-biphenyl)-2-yl)methyl)piperazin-1-yl)benzoyl)-4-(((4-methoxycyclohexyl)methyl)amino)-3-nitrobenzenesulfonamide, N-(4-(4-((1,1'-biphenyl)-2-ylmethyl)piperazin-1-yl)benzoyl)-3-nitro-4-((2-(2-thienylsulfanyl)ethyl)amino)benzenesulfonamide, N-(4-(4-((4'-chloro(1,1'-biphenyl)-2-yl)methyl)piperazin-1-yl)benzoyl)-4-((1,1-dimethyl-2-(2-thienylsulfanyl)ethyl)amino)-3-nitrobenzenesulfonamide, N-(4-(4-((4'-chloro(1,1'-biphenyl)-2-yl)methyl)piperazin-1-yl)benzoyl)-4-(((1R)-3-(morpholin-4-yl)-1-((1,3-thiazol-2-ylsulfanyl)methyl)propyl)amino)-3-nitrobenzenesulfonamide, (3R)-3-(4-(((4-(4-((4'-chloro(1,1'-biphenyl)-2-yl)methyl)piperazin-1-yl)benzoyl)amino)sulfonyl)-2-nitroanilino)-N,N-dimethyl-4-(pyrimidin-2-ylsulfanyl)butanamide, N-(4-(4-((4'-chloro(1,1'-biphenyl)-2-yl)methyl)piperazin-1-yl)benzoyl)-4-(((1R)-3-(morpholin-4-yl)-3-oxo-1-((2-thienylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-((1,1-dimethyl-2-(pyrimidin-2-ylsulfanyl)ethyl)amino)-3-nitrobenzenesulfonamide, (3R)-3-(4-(((4-(4-((4'-chloro(1,1'-biphenyl)-2-yl)methyl)piperazin-1-yl)benzoyl)amino)sulfonyl)-2-nitroanilino)-N,N-dimethyl-4-(1,3-thiazol-2-ylsulfanyl)butanamide, N-(4-(4-((4'-chloro(1,1'-biphenyl)-2-yl)methyl)piperazin-1-yl)benzoyl)-4-(((1R)-3-(morpholin-4-yl)-1-((2-thienylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-(((4-(trifluoromethoxy)phenyl)sulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-nitro-4-((2-phenoxyethyl)amino)benzenesulfonamide, N-(4-(4-((4'-chloro(1,1'-biphenyl)-2-yl)methyl)piperazin-1-yl)benzoyl)-4-(((1R)-3-(morpholin-4-yl)-1-(((4-(trifluoromethoxy)phenyl)sulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-1-(((4-methoxyphenyl)sulfanyl)methyl)-3-(morpholin-4-yl)propyl)amino)-3-nitrobenzenesulfonamide, N-(4-(4-((4'-chloro(1,1'-biphenyl)-2-yl)methyl)piperazin-1-yl)benzoyl)-4-(((1R)-1-(((4-methylphenyl)sulfanyl)methyl)-3-(morpholin-4-yl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((2-thienylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-1-(((4-chlorophenyl)sulfanyl)methyl)-3-(morpholin-4-yl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-(((4-fluorophenyl)sulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-1-(((4-fluorophenyl)sulfanyl)methyl)-3-(morpholin-4-yl)propyl)amino)-3-nitrobenzenesulfonamide, N-(4-(4-((4'-chloro(1,1'-biphenyl)-2-yl)methyl)piperazin-1-yl)-2-fluorobenzoyl)-4-(((1R)-3-(dimethylamino)-1-((phenylsulfanyl)methyl)propyl)amino)-3-nitrobenzenesulfonamide, N-(4-(1-((4'-chloro(1,1'-biphenyl)-2-yl)methyl)-1,2,3,6-tetrahydropyridin-4-yl)benzoyl)-4-(((1R)-3-(dimethylamino)-1-((phenylsulfanyl)methyl)propyl)amino)-3-nitrobenzenesulfonamide, N-(4-(1-((4'-chloro(1,1'-biphenyl)-2-yl)methyl)-1,2,3,6-tetrahydropyridin-4-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)-2-fluorobenzoyl)-4-(((1R)-3-(dimethylamino)-1-((phenylsulfanyl)methyl)propyl)amino)-3-(trifluoromethyl)benzenesulfonamide, N-((6-(4-((4'-chloro(1,1'-biphenyl)-2-yl)methyl)piperazin-1-yl)pyridin-3-yl)carbonyl)-4-(((1R)-3-(dimethylamino)-1-((phenylsulfanyl)methyl)propyl)amino)-3-nitrobenzenesulfonamide, N-(4-(1-((4'-chloro(1,1'-biphenyl)-2-yl)methyl)piperidin-4-yl)benzoyl)-4-(((1R)-3-(dimethylamino)-1-((phenylsulfanyl)methyl)propyl)amino)-3-nitrobenzenesulfonamide, N-(4-(1-((4'-chloro(1,1'-biphenyl)-2-yl)methyl)piperidin-4-yl)benzoyl)-4-(((1R)-3-(morpholin-4-yl)-1-((phenylsulfanyl)methyl)propyl)amino)-3-nitrobenzenesulfonamide, N-(4-(1-((4'-chloro(1,1'-biphenyl)-2-yl)methyl)-1,2,3,6-tetrahydropyridin-4-yl)benzoyl)-4-(((1R)-3-(dimethylamino)-1-((phenylsulfanyl)methyl)propyl)amino)-3-(trifluoromethyl)benzenesulfonamide, N-((6-(4-((4'-chloro(1,1'-biphenyl)-2-yl)methyl)piperazin-1-yl)pyridin-3-yl)carbonyl)-4-(((1R)-3-(morpholin-4-yl)-1-((phenylsulfanyl)methyl)propyl)amino)-3-nitrobenzenesulfonamide, N-((6-(4-((4'-chloro(1,1'-biphenyl)-2-yl)methyl)piperazin-1-yl)pyridin-3-yl)carbonyl)-4-(((1R)-3-(dimethylamino)-1-((phenylsulfanyl)methyl)propyl)amino)-3-(trifluoromethyl)benzenesulfonamide, N-(4-(4-((4'-chloro(1,1'-biphenyl)-2-yl)methyl)piperidin-1-yl)benzoyl)-4-(((1R)-3-(dimethylamino)-1-((phenylsulfanyl)methyl)propyl)amino)-3-nitrobenzenesulfonamide, N-(4-(4-((4'-chloro(1,1'-biphenyl)-2-yl)methyl)piperidin-1-yl)benzoyl)-4-(((1R)-3-(morpholin-4-yl)-1-((phenylsulfanyl)methyl)propyl)amino)-3-nitrobenzenesulfonamide, N-((5-(4-((4'-chloro(1,1'-biphenyl)-2-yl)methyl)piperazin-1-yl)pyridin-2-yl)carbonyl)-4-(((1R)-3-(dimethylamino)-1-((phenylsulfanyl)methyl)propyl)amino)-3-nitrobenzenesulfonamide, N-((5-(4-((4'-chloro(1,1'-biphenyl)-2-yl)methyl)piperazin-1-yl)pyridin-2-yl)carbonyl)-4-(((1R)-3-(morpholin-4-yl)-1-((phenylsulfanyl)methyl)propyl)amino)-3-nitrobenzenesulfonamide, N-(4-(1-((2-(4-chlorophenyl)-5,5-dimethyl-1-cyclohexen-1-yl)methyl)-1,2,3,6-tetrahydropyridin-4-yl)benzoyl)-4-(((1R)-3-(dimethylamino)-1-((phenylsulfanyl)methyl)propyl)amino)-3-nitrobenzenesulfonamide, N-(4-(1-((2-(4-chlorophenyl)-1-cyclohexen-1-yl)methyl)-1,2,3,6-tetrahydropyridin-4-yl)benzoyl)-4-(((1R)-3-(dimethylamino)-1-((phenylsulfanyl)methyl)propyl)amino)-3-nitrobenzenesulfonamide, N-(4-(1-((2-(4-chlorophenyl)-1-cyclohexen-1-yl)methyl)-1,2,3,6-tetrahydropyridin-4-yl)benzoyl)-4-(((1R)-3-(morpholin-4-yl)-1-((phenylsulfanyl)methyl)propyl)amino)-3-nitrobenzenesulfonamide, N-(4-(1-((2-(4-chlorophenyl)-5,5-dimethyl-1-cyclohexen-1-yl)methyl)-1,2,3,6-tetrahydropyridin-4-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)-1-cyclohexen-1-yl)benzoyl)-4-(((1R)-3-(dimethylamino)-1-((phenylsulfanyl)methyl)propyl)amino)-3-nitrobenzenesulfonamide, N-(4-(4-((4'-chloro(1,1'-biphenyl)-2-yl)methyl)-1-cyclohexen-1-yl)benzoyl)-4-(((1R)-3-(morpholin-4-yl)-1-((phenylsulfanyl)methyl)propyl)amino)-3-nitrobenzenesulfonamide, N-(4-((3aR,6aS)-5-((4'-chloro(1,1'-biphenyl)-2-yl)methyl)hexahydropyrrolo[3,4-c]pyrrol-2(1H)-yl)benzoyl)-4-(((1R)-3-(dimethylamino)-1-((phenylsulfanyl)methyl)propyl)amino)-3-nitrobenzenesulfonamide, N-(4-(4-((1,1'-biphenyl)-2-ylmethyl)piperazin-1-yl)benzoyl)-4-(methyl((methyl-4-(trifluoromethoxy)anilino)carbonyl)amino)-3-nitrobenzenesulfonamide, N-(4-(4-((11'-biphenyl)-2-ylmethyl)piperazin-1-yl)benzoyl)-4-(((2-dimethylanilino)carbonyl)(methyl)amino)-3-nitrobenzenesulfonamide, N-(4-(4-((1,1'-biphenyl)-2-ylmethyl)piperazin-1-yl)benzoyl)-4-(((4-methoxy(methyl)anilino)carbonyl)(methyl)amino)-3-nitrobenzenesulfonamide, N-(4-(4-((11'-biphenyl)-2-ylmethyl)piperazin-1-yl)benzoyl)-4-(((4-dimethylanilino)carbonyl)(methyl)amino)-3-nitrobenzenesulfonamide, 4-(((benzhydryl(methyl)amino)carbonyl)(methyl)amino)-N-(4-(4-((1,1'-biphenyl)-2-ylmethyl)piperazin-1-yl)benzoyl)-3-nitrobenzenesulfonamide, N-(4-(4-((1,1'-biphenyl)-2-ylmethyl)piperazin-1-yl)benzoyl)-4-(methyl((methyl((1S)-1-phenylethyl)amino)carbonyl)amino)-3-nitrobenzenesulfonamide, N-(4-(4-((1,1'-biphenyl)-2-ylmethyl)piperazin-1-yl)benzoyl)-4-(methyl((methyl(2-(4-methylpiperazin-1-yl)-1-phenylethyl)amino)carbonyl)amino)-3-nitrobenzenesulfonamide, N-(4-(4-((1,1'-biphenyl)-2-ylmethyl)piperazin-1-yl)benzoyl)-4-(methyl((methyl(2-(morpholin-4-yl)-1-phenylethyl)amino)carbonyl)amino)-3-nitrobenzenesulfonamide, N-(4-(4-(((1,1'-biphenyl)-2-ylmethyl)piperazin-1-yl)benzoyl)-4-(((((1,2-diphenylethyl)(methyl)amino)carbonyl)(methyl)amino)-3-nitrobenzenesulfonamide, N-(4-(4-(((1,1'-biphenyl)-2-ylmethyl)piperazin-1-yl)benzoyl)-4-(((((2-(dimethylamino)-1-phenylethyl)(methyl)amino)carbonyl)(methyl)amino)-3-nitrobenzenesulfonamide, 3-amino-N-(4-(4-((4'-chloro(1,1'-biphenyl)-2-yl)methyl)piperazin-1-yl)benzoyl)-4-((2-(phenylsulfanyl)ethyl)amino)benzenesulfonamide, N-(4-(4-((4'-chloro(1,1'-biphenyl)-2-yl)methyl)piperazin-1-yl)benzoyl)-1-(2-(phenylsulfanyl)ethyl)-1H-1,2,3-benzotriazole-5-sulfonamide, N-(4-(4-((4'-chloro(1,1'-biphenyl)-2-yl)methyl)piperazin-1-yl)benzoyl)-1-(2-(phenylsulfanyl)ethyl)-1H-benzimidazole-5-sulfonamide, N-(4-(4-(((1,1'-biphenyl)-2-ylmethyl)-4-methoxypiperidin-1-yl)benzoyl)-4-((cyclohexylmethyl)amino)-3-nitrobenzenesulfonamide, N-(4-(4-(((1,1'-biphenyl)-2-ylmethyl)-4-methoxypiperidin-1-yl)benzoyl)-4-(cyclohexylamino)-3-nitrobenzenesulfonamide, N-(4-(4-(((1,1'-biphenyl)-2-ylmethyl)-4-methoxypiperidin-1-yl)benzoyl)-4-((1,1-dimethyl-2-(phenylsulfanyl)ethyl)amino)-3-nitrobenzenesulfonamide, N-(4-(4-(((1,1'-biphenyl)-2-ylmethyl)piperazin-1-yl)benzoyl)-3-nitro-4-((1-((phenylsulfanyl)methyl)cyclopentyl)amino)benzene-sulfonamide, N-(4-(4-(((1,1'-biphenyl)-2-ylmethyl)-4-methoxypiperidin-1-yl)benzoyl)-3-nitro-4-((1-((phenylsulfanyl)methyl)cyclopentyl)amino)benzene-sulfonamide, N-(4-(4-((4'-chloro(1,1'-biphenyl)-2-yl)methyl)piperazin-1-yl)benzoyl)-3-nitro-4-((1-((phenylsulfanyl)methyl)cyclopentyl)amino)benzene-sulfonamide, N-(4-(4-((4'-chloro(1,1'-biphenyl)-2-yl)methyl)piperazin-1-yl)benzoyl)-3-nitro-4-(((1S)-1-((phenylsulfanyl)methyl)propyl)amino)benzenesulfonamide, N-(4-(4-(((1,1'-biphenyl)-2-ylmethyl)-4-methoxypiperidin-1-yl)benzoyl)-3-nitro-4-(((1S)-1-((phenylsulfanyl)methyl)propyl)amino)benzenesulfonamide, N-(4-(4-((4'-chloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1S)-3-methyl-1-((phenylsulfanyl)methyl)butyl)amino)-3-nitrobenzenesulfonamide, N-(4-(4-(((1,1'-biphenyl)-2-ylmethyl)-4-methoxypiperidin-1-yl)benzoyl)-4-(((1S)-3-methyl-1-((phenylsulfanyl)methyl)butyl)amino)-3-nitrobenzenesulfonamide, N-(4-(4-((4'-chloro(1,1'-biphenyl)-2-yl)methyl)piperazin-1-yl)benzoyl)-3-nitro-4-((1-((phenylsulfanyl)methyl)cyclopropyl)amino)benzene-sulfonamide, N-(4-(4-((4'-chloro(1,1'-biphenyl)-2-yl)methyl)piperazin-1-yl)benzoyl)-3-nitro-4-((1-((phenylsulfanyl)methyl)cyclohexyl)amino)benzene-sulfonamide, N-(4-(4-((4'-chloro(1,1'-biphenyl)-2-yl)methyl)piperazin-1-yl)benzoyl)-4-(((1R)-1-methyl-2-(phenylsulfanyl)ethyl)amino)-3-nitrobenzenesulfonamide, N-(4-(4-(((1,1'-biphenyl)-2-ylmethyl)piperazin-1-yl)benzoyl)-4-(((1S)-1-methyl-2-(phenylsulfanyl)ethyl)amino)-3-nitrobenzenesulfonamide, N-(4-(4-(((1,1'-biphenyl)-2-ylmethyl)piperazin-1-yl)benzoyl)-3-nitro-4-(((1R,2S)-2-(phenylsulfanyl)cyclohexyl)amino)benzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide, 4-(((1R)-5-amino-1-((phenylsulfanyl)methyl)pentyl)amino)-N-(4-(4-((4'-chloro(1,1'-biphenyl)-2-yl)methyl)piperazin-1-yl)benzoyl)-3-nitrobenzenesulfonamide, N-(4-(4-(((1,1'-biphenyl)-2-ylmethyl)piperazin-1-yl)benzoyl)-3-nitro-4-(((1S)-2-(phenylsulfanyl)-1-(pyridin-3-ylmethyl)ethyl)amino)benzenesulfonamide, N-(4-(4-(((1,1'-biphenyl)-2-ylmethyl)-4-methoxypiperidin-1-yl)benzoyl)-3-nitro-4-(((1S)-2-(phenylsulfanyl)-1-(pyridin-3-ylmethyl)ethyl)amino)benzenesulfonamide, N-(4-(4-(((1,1'-biphenyl)-2-ylmethyl)piperazin-1-yl)benzoyl)-3-nitro-4-(((1S,2R)-2-(phenylsulfanyl)cyclohexyl)amino)benzenesulfonamide, N-(4-(4-(((1,1'-biphenyl)-2-ylmethyl)piperazin-1-yl)benzoyl)-4-((1-(((2-methyl-3-furyl)sulfanyl)methyl)cyclopentyl)amino)-3-nitrobenzenesulfonamide, N-(4-(4-((4'-chloro(1,1'-biphenyl)-2-yl)methyl)piperazin-1-yl)benzoyl)-4-((1-(((2-methyl-3-furyl)sulfanyl)methyl)cyclopentyl)amino)-3-nitrobenzenesulfonamide, N-(4-(4-((4'-chloro(1,1'-biphenyl)-2-yl)methyl)piperazin-1-yl)benzoyl)-3-nitro-4-(((1S)-2-(phenylsulfanyl)-1-(pyridin-3-ylmethyl)ethyl)amino)benzenesulfonamide, N-(4-(4-((2-(4-chlorophenyl)-3-pyridin-3-yl)methyl)piperazin-1-yl)benzoyl)-4-(((1R)-(dimethylamino)-1-((phenylsulfanyl)methyl)propyl)amino)-3-nitrobenzenesulfonamide, N-(4-(4-((2-(4-chlorophenyl)pyridin-3-yl)methyl)piperazin-1-yl)benzoyl)-3-nitro-4-((2-(phenylsulfanyl)ethyl)amino)benzenesulfonamide, N-(4-(4-((2-(4-chlorophenyl)pyridin-3-yl)methyl)piperazin-1-yl)benzoyl)-4-(((1R)-3-(morpholin-4-yl)-1-((phenylsulfanyl)methyl)propyl)amino)-3-nitrobenzenesulfonamide, 3-nitro-N-(4-(4-((2-phenylpyridin-3-yl)methyl)piperazin-1-yl)benzoyl)-4-((2-(phenylsulfanyl)ethyl)amino)benzenesulfonamide, 4-(((1R)-3-(morpholin-4-yl)-1-((phenylsulfanyl)methyl)propyl)amino)-3-nitro-N-(4-(4-((2-phenylpyridin-3-yl)methyl)piperazin-1-yl)benzoyl)benzenesulfonamide, 4-(((1R)-3-(dimethylamino)-1-((phenylsulfanyl)methyl)propyl)amino)-3-nitro-N-(4-(4-((2-phenylpyridin-3-yl)methyl)piperazin-1-yl)benzoyl)benzenesulfonamide, 4-(((1R)-3-(dimethylamino)-1-((phenylsulfanyl)methyl)propyl)amino)-N-(4-(4-((2-(4-(methylsulfanyl)phenyl)pyridin-3-yl)methyl)piperazin-1-yl)benzoyl)-3-nitrobenzenesulfonamide, 4-(((1R)-3-(dimethylamino)-1-((phenylsulfanyl)methyl)propyl)amino)-N-(4-(4-((2-(4-methoxyphenyl)pyridin-3-yl)methyl)piperazin-1-yl)benzoyl)-3-nitrobenzenesulfonamide, N-(4-(4-((2-(4-(dimethylamino)phenyl)pyridin-3-yl)methyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-((2-(4-fluorophenyl)pyridin-3-yl)methyl)piperazin-1-yl)benzoyl)-3-nitrobenzenesulfonamide, 4-(((1R)-3-(dimethylamino)-1-((phenylsulfanyl)methyl)propyl)amino)-N-(4-(4-((2-(4-(methylsulfonyl)phenyl)pyridin-3-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-((2-(pyridin-4-ylsulfanyl)ethyl)amino)benzenesulfonamide, 4-(((1R)-3-(dimethylamino)-1-((phenylsulfanyl)methyl)propyl)amino)-N-(4-(4-((4'-(methylsulfonyl)(1,1'-biphenyl)-2-yl)methyl)piperazin-1-yl)benzoyl)-3-nitrobenzenesulfonamide, N-(4-(4-((4'-(methylsulfonyl)(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(morpholin-4-yl)-1-((phenylsulfonyl)methyl)propyl)amino)-3-nitrobenzenesulfonamide, N-(4-(4-((4'-(dimethylamino)(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, (3R)-3-(4-(((4-(4-((4'-chloro(1,1'-biphenyl)-2-yl)methyl)piperazin-1-yl)benzoyl)amino)sulfonyl)-2-nitroanilino)-N,N-dimethyl-4-(phenylsulfonyl)butanamide, N-(4-(4-((4'-chloro(1,1'-biphenyl)-2-yl)methyl)piperazin-1-yl)benzoyl)-3-nitro-4-(((3S,4R)-(phenylsulfanyl)pyrrolidin-4-yl)amino)benzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyridin-4-ylsulfanyl)propyl)amino)benzenesulfonamide, N-(4-(4-((3-(4-chlorophenyl)pyridin-4-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((3-(4-chlorophenyl)pyridin-4-yl)methyl)piperazin-1-yl)benzoyl)-3-nitro-4-((2-(phenylsulfanyl)ethyl)amino)benzenesulfonamide, N-(4-(4-((2-(4-chlorophenyl)-1-cyclopenten-1-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((2-(4-chlorophenyl)-1-cyclohexen-1-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((2-bromo-1-cyclopenten-1-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((2-(4-chlorophenyl)-1-cyclohexen-1-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((2-(4-chlorophenyl)-1-cyclohexen-1-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide, N-(4-(4-((2-bromo-1-cyclohexen-1-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((4-(4-chlorophenyl)-5,6-dihydro-2H-pyran-3-yl)methyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-((2-(4-methoxyphenyl)-1-cyclohexen-1-yl)methyl)piperazin-1-yl)benzoyl)-3-nitrobenzenesulfonamide, 4-(((1R)-3-(dimethylamino)-1-((phenylsulfanyl)methyl)propyl)amino)-N-(4-(4-((2-(4-fluorophenyl)-1-cyclohexen-1-yl)methyl)piperazin-1-yl)benzoyl)-3-nitrobenzenesulfonamide, 4-(((1R)-3-(dimethylamino)-1-((phenylsulfanyl)methyl)propyl)amino)-3-nitro-N-(4-(4-((2-phenyl-1-cyclohexen-1-yl)methyl)piperazin-1-yl)benzoyl)benzenesulfonamide, N-(4-(4-((2-(4-chlorophenyl)-1-cycloocten-1-yl)methyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-((2-(4-(methylsulfanyl)phenyl)-1-cyclohexen-1-yl)methyl)piperazin-1-yl)benzoyl)-3-nitrobenzenesulfonamide, N-(4-(4-((2-(4-chlorophenyl)-1-cyclohepten-1-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((2-(4-chlorophenyl)-1-cyclohepten-1-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((2-(4-chlorophenyl)-5,5-dimethyl-1-cyclohexen-1-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((2-(4-chlorophenyl)-5,5-dimethyl-1-cyclohexen-1-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((1,1'-biphenyl)-2-ylmethyl)-4-(2-(morpholin-4-yl)ethoxy)piperidin-1-yl)benzoyl)-4-((1,1-dimethyl-2-(phenylsulfanyl)ethyl)amino)-3-nitrobenzenesulfonamide, N-(4-(4-((1,1'-biphenyl)-2-ylmethyl)-4-(2-(morpholin-4-yl)ethoxy)piperidin-1-yl)benzoyl)-3-nitro-4-((2-(phenylsulfanyl)ethyl)amino)benzenesulfonamide, N-(4-(4-((1,1'-biphenyl)-2-ylmethyl)-4-(2-(pyrrolidin-1-yl)ethoxy)piperidin-1-yl)benzoyl)-4-((1,1-dimethyl-2-(phenylsulfanyl)ethyl)amino)-3-nitrobenzenesulfonamide, N-(4-(4-((1,1'-biphenyl)-2-ylmethyl)-4-(2-(pyrrolidin-1-yl)ethoxy)piperidin-1-yl)benzoyl)-3-nitro-4-((2-(phenylsulfanyl)ethyl)amino)benzenesulfonamide, N-(4-(4-((1,1'-biphenyl)-2-ylmethyl)-4-(2-(pyrrolidin-1-yl)ethoxy)piperidin-1-yl)benzoyl)-3-nitro-4-((1-((phenylsulfanyl)methyl)cyclopentyl)amino)benzene-sulfonamide, N-(4-(4-((1,1'-biphenyl)-2-ylmethyl)-4-(2-(dimethylamino)ethoxy)piperidin-1-yl)benzoyl)-4-((1,1-dimethyl-2-(phenylsulfanyl)ethyl)amino)-3-nitrobenzenesulfonamide, N-(4-(4-((1,1'-biphenyl)-2-ylmethyl)-4-(2-(dimethylamino)ethoxy)piperidin-1-yl)benzoyl)-3-nitro-4-((2-(phenylsulfanyl)ethyl)amino)benzenesulfonamide, N-(4-(4-((1,1'-biphenyl)-2-ylmethyl)-4-(2-(dimethylamino)ethoxy)piperidin-1-yl)benzoyl)-3-nitro-4-((1-((phenylsulfanyl)methyl)cyclopentyl)amino)benzene-sulfonamide, N-(4-(4-((1,1'-biphenyl)-2-ylmethyl)-4-(2-(piperidin-1-yl)ethoxy)piperidin-1-yl)benzoyl)-4-((1,1-dimethyl-2-(phenylsulfanyl)ethyl)amino)-3-nitrobenzenesulfonamide, N-(4-(4-((1,1'-biphenyl)-2-ylmethyl)-4-(2-(piperidin-1-yl)ethoxy)piperidin-1-yl)benzoyl)-3-nitro-4-((2-(phenylsulfanyl)ethyl)amino)benzenesulfonamide, N-(4-(4-((1,1'-biphenyl)-2-ylmethyl)-4-(2-(piperidin-1-yl)ethoxy)piperidin-1-yl)benzoyl)-3-nitro-4-((1-((phenylsulfanyl)methyl)cyclopentyl)amino)benzene-sulfonamide, N-(4-(4-((1,1'-biphenyl)-2-ylmethyl)piperazin-1-yl)benzoyl)-4-(((1S)-3-(morpholin-4-yl)-1-((phenylsulfanyl)methyl)propyl)amino)-3-nitrobenzenesulfonamide, N-(4-(4-((4'-(2-(dimethylamino)ethoxy)(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((4'-(2-(dimethylamino)ethoxy)(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-(2-(dimethylamino)ethoxy)(1,1'-biphenyl)-2-yl)methyl)piperazin-1-yl)benzoyl)-4-((1,1-dimethyl-2-(phenylsulfanyl)ethyl)amino)-3-nitrobenzenesulfonamide, N-(4-(4-((4'-(2-(dimethylamino)ethoxy)(1,1'-biphenyl)-2-yl)methyl)piperazin-1-yl)benzoyl)-3-nitro-4-((2-(phenylsulfanyl)ethyl)amino)benzenesulfonamide, 4-(((1R)-3-(dimethylamino)-1-((phenylsulfanyl)methyl)propyl)amino)-N-(4-(4-((4'-(2-(morpholin-4-yl)ethoxy)(1,1'-biphenyl)-2-yl)methyl)piperazin-1-yl)benzoyl)-3-nitrobenzenesulfonamide, N-(4-(4-((4'-(2-(morpholin-4-yl)ethoxy)(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, 4-((1,1-dimethyl-2-(phenylsulfanyl)ethyl)amino)-N-(4-(4-((4'-(2-(morpholin-4-yl)ethoxy)(1,1'-biphenyl)-2-yl)methyl)piperazin-1-yl)benzoyl)-3-nitrobenzenesulfonamide, N-(4-(4-((4'-(2-(morpholin-4-yl)ethoxy)(1,1'-biphenyl)-2-yl)methyl)piperazin-1-yl)benzoyl)-3-nitro-4-((2-(phenylsulfanyl)ethyl)amino)benzenesulfonamide, N-(4-(4-((4'-chloro(1,1'-biphenyl)-2-yl)methyl)piperazin-1-yl)benzoyl)-4-(((1R)-3-(1H-imidazol-1-yl)-1-((phenylsulfanyl)methyl)propyl)amino)-3-nitrobenzenesulfonamide, N-(4-(4-((1,1'-biphenyl)-2-ylmethyl)piperazin-1-yl)benzoyl)-4-(((1R)-3-(1H-imidazol-1-yl)-1-((phenylsulfanyl)methyl)propyl)amino)-3-nitrobenzenesulfonamide, N-(4-(4-((1,1'-biphenyl)-2-ylmethyl)-4-methoxy-piperidin-1-yl)benzoyl)-4-(((1R)-3-(1H-imidazol-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-4-(4-methylpiperazin-1-yl)-1-((phenylsulfanyl)methyl)butyl)amino)-3-nitrobenzenesulfonamide, N-(4-(4-((4'-chloro(1,1'-biphenyl)-2-yl)methyl)piperazin-1-yl)benzoyl)-4-(((1R)-2-((2-(dimethylamino)ethyl)(methyl)amino)-1-((phenylsulfanyl)methyl)ethyl)amino)-3-nitrobenzenesulfonamide, (4R)-4-(4-(((4-(4-((4'-chloro(1,1'-biphenyl)-2-yl)methyl)piperazin-1-yl)benzoyl)amino)sulfonyl)-2-nitroanilino)-N,N-dimethyl-5-(phenylsulfanyl)pentanamide, N-(4-(4-((4'-chloro(1,1'-biphenyl)-2-yl)methyl)piperazin-1-yl)benzoyl)-4-(((1R)-4-(dimethylamino)-1-((phenylsulfonyl)methyl)butyl)amino)-3-nitrobenzenesulfonamide, 2-(((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)(methyl)amino)-N,N-dimethylacetamide, (3R)-N-(tert-butyl)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butanamide, (3R)-3-(4-(((4-(4-((4'-chloro(1,1'-biphenyl)-2-yl)methyl)piperazin-1-yl)benzoyl)amino)sulfonyl)-2-nitroanilino)-N,N-diisopropyl-4-(phenylsulfanyl)butanamide, (3R)-N-(tert-butyl)-3-(4-(((4-(4-((4'-chloro(1,1'-biphenyl)-2-yl)methyl)piperazin-1-yl)benzoyl)amino)sulfonyl)-2-nitroanilino)-N-methyl-4-(phenylsulfanyl)butanamide, (3R)-3-(4-(((4-(4-((4'-chloro(1,1'-biphenyl)-2-yl)methyl)piperazin-1-yl)benzoyl)amino)sulfonyl)-2-nitroanilino)-N-isopropyl-N-methyl-4-(phenylsulfanyl)butanamide, N-(4-(4-((4'-chloro(1,1'-biphenyl)-2-yl)methyl)piperazin-1-yl)benzoyl)-3-nitro-4-(((1R)-3-oxo-1-((phenylsulfanyl)methyl)-3-(piperidin-1-yl)propyl)amino)benzenesulfonamide, N-((5R)-5-(4-(((4-(4-((4'-chloro(1,1'-biphenyl)-2-yl)methyl)piperazin-1-yl)benzoyl)amino)sulfonyl)-2-nitroanilino)-6-(phenylsulfanyl)hexyl)-2-(dimethylamino)acetamide, (3R)-3-(4-(((4-(4-((4'-chloro(1,1'-biphenyl)-2-yl)methyl)piperazin-1-yl)benzoyl)amino)sulfonyl)-2-nitroanilino)-N,N-dimethyl-4-(phenylsulfanyl)butanamide, N-(4-(4-((4'-chloro(1,1'-biphenyl)-2-yl)methyl)piperazin-1-yl)benzoyl)-4-(((1R)-3-(1,1-dioxidothiomorpholin-4-yl)-3-oxo-1-((phenylsulfanyl)methyl)propyl)amino)-3-nitrobenzenesulfonamide, (3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butanamide, (3R)-3-(4-(((4-(4-((4'-chloro(1,1'-biphenyl)-2-yl)methyl)piperazin-1-yl)benzoyl)amino)sulfonyl)-2-nitroanilino)-N-cyclopropyl-4-(phenylsulfanyl)butanamide, (3R)-3-(4-(((4-(4-((4'-chloro(1,1'-biphenyl)-2-yl)methyl)piperazin-1-yl)benzoyl)amino)sulfonyl)-2-nitroanilino)-N-cyclobutyl-4-(phenylsulfanyl)butanamide, N-(4-(4-((4'-chloro(1,1'-biphenyl)-2-yl)methyl)piperazin-1-yl)benzoyl)-4-(((1R)-3-(4-methylpiperazin-1-yl)-3-oxo-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(morpholin-4-yl)-3-oxo-1-((phenylsulfanyl)methyl)propyl)amino)-3-nitrobenzenesulfonamide, 4-(((1R)-3-(azetidin-1-yl)-3-oxo-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, (3R)-3-(4-(((4-(4-((4'-chloro(1,1'-biphenyl)-2-yl)methyl)piperazin-1-yl)benzoyl)amino)sulfonyl)-2-nitroanilino)-N-(2-(morpholin-4-yl)ethyl)-4-(phenylsulfanyl)butanamide, (3R)-3-(4-(((4-(4-((4'-chloro(1,1'-biphenyl)-2-yl)methyl)piperazin-1-yl)benzoyl)amino)sulfonyl)-2-nitroanilino)-N-methyl-4-(phenylsulfanyl)butanamide, 4-(((1R)-3-amino-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-4-(((1R)-3-cyano-1-((phenylsulfanyl)methyl)propyl)amino)-3-nitrobenzenesulfonamide, 4-(((1R)-3-(tert-butylamino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-4-(((1R)-3-(cyclopropylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(cyclobutylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(diethylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(isopropyl(methyl)amino)-1-((phenylsulfanyl)methyl)propyl)amino)-3-nitrobenzenesulfonamide, 4-(((1R)-3-(tert-butyl(methyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(piperidin-1-yl)propyl)amino)benzenesulfonamide, N-(4-(4-((4'-chloro(1,1'-biphenyl)-2-yl)methyl)piperazin-1-yl)benzoyl)-4-(((1R)-3-(4-hydroxypiperidin-1-yl)-1-((phenylsulfanyl)methyl)propyl)amino)-3-nitrobenzenesulfonamide, 4-(((1R)-3-(4-acetylpiperazin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(thiomorpholin-4-yl)propyl)amino)benzenesulfonamide, N-(4-(4-((4'-chloro(1,1'-biphenyl)-2-yl)methyl)piperazin-1-yl)benzoyl)-4-(((1R)-3-((2-(morpholin-4-yl)ethyl)amino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(piperazin-1-yl)propyl)amino)benzenesulfonamide, N-(4-(4-((4'-chloro(1,1'-biphenyl)-2-yl)methyl)piperazin-1-yl)benzoyl)-4-(((1R)-3-((3R)-3-hydroxypyrrolidin-1-yl)-1-((phenylsulfanyl)methyl)propyl)amino)-3-nitrobenzenesulfonamide, 4-(((1R)-3-((3R)-3-aminopyrrolidin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-4-(((1R)-3-(3-hydroxyazetidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(4-methylpiperazin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(1,1-dioxidothiomorpholin-4-yl)-1-((phenylsulfanyl)methyl)propyl)amino)-3-nitrobenzenesulfonamide, 4-(((1R)-3-(1,3-benzodioxol-5-ylamino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, 4-(((1R)-3-((1,3-benzodioxol-4-ylmethyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-((pyridin-2-ylmethyl)amino)propyl)amino)benzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-((2-(pyridin-2-yl)ethyl)amino)propyl)amino)benzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-((pyridin-4-ylmethyl)amino)propyl)amino)benzenesulfonamide, N-(4-(4-((4'-chloro(1,1'-biphenyl)-2-yl)methyl)piperazin-1-yl)benzoyl)-4-(((1R)-3-(morpholin-4-ylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(methyl(pyridin-4-yl)amino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyridin-3-ylamino)propyl)amino)benzenesulfonamide, N-(4-(4-((4'-chloro(1,1'-biphenyl)-2-yl)methyl)piperazin-1-yl)benzoyl)-4-(((1R)-3-(2,6-dimethylpiperidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-((2R,6S)-2,6-dimethylpiperidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyrrolidin-1-ylamino)propyl)amino)benzenesulfonamide, N-(4-(4-((4'-chloro(1,1'-biphenyl)-2-yl)methyl)piperazin-1-yl)benzoyl)-4-(((1R)-3-(4-(methoxyimino)piperidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(2H-tetrazol-5-yl)propyl)amino)benzenesulfonamide, N-(4-(4-((4'-chloro(1,1'-biphenyl)-2-yl)methyl)piperazin-1-yl)benzoyl)-4-(((1R)-3-(diisopropylamino)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-3-(isopropylamino)-1-((phenylsulfanyl)methyl)propyl)amino)-3-(trifluoromethyl)benzenesulfonamide, 4-(((1R)-3-(bis(2-hydroxyethyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-(((1R)-3-(dimethylamino)-1-((phenylsulfanyl)methyl)propyl)amino)-4-(trifluoromethoxy)benzenesulfonamide, N-(4-(4-((4'-chloro(1,1'-biphenyl)-2-yl)methyl)piperazin-1-yl)benzoyl)-4-(((1R)-3-(isopropyl(methyl)amino)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-3-(diethylamino)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-3-(2,5-dimethylpyrrolidin-1-yl)-1-((phenylsulfanyl)methyl)propyl)amino)-3-nitrobenzenesulfonamide, 4-(((1R)-3-amino-1-((phenylsulfanyl)methyl)propyl)
amino)-N-(4-(4-((4'-chloro(1,1'-biphenyl)-2-yl)methyl)
piperazin-1-yl)benzoyl)-3-(trifluoromethyl)benzene-
sulfonamide, N-(4-(4-((4'-chloro(1,1'-biphenyl)-2-yl)methyl)piperazin-1-
yl)benzoyl)-4-(((1R)-3-(dimethylamino)-1-((phenylsulfa-
nyl)methyl)propyl)amino)-2-(trifluoromethyl)benzene-
sulfonamide, N-(4-(4-((4'-chloro(1,1'-biphenyl)-2-yl)methyl)piperazin-1-
yl)benzoyl)-4-(((1R)-3-(dimethylamino)-1-((phenylsulfa-
nyl)methyl)propyl)amino)-3-fluorobenzenesulfonamide, N-(4-(4-((4'-chloro(1,1'-biphenyl)-2-yl)methyl)piperazin-1-
yl)benzoyl)-4-(((1R)-3-(dimethylamino)-1-((phenylsulfa-
nyl)methyl)propyl)amino)-2-(trifluoromethoxy)benzene-
sulfonamide, N-(4-(4-((4'-chloro(1,1'-biphenyl)-2-yl)methyl)piperazin-1-
yl)benzoyl)-4-(((1R)-3-(dimethylamino)-1-((phenylsulfa-
nyl)methyl)propyl)amino)-2,5-difluorobenzenesulfona-
mide, N-(4-(4-((4'-chloro(1,1'-biphenyl)-2-yl)methyl)piperazin-1-
yl)benzoyl)-4-(((1R)-3-(dimethylamino)-1-((phenylsulfa-
nyl)methyl)propyl)amino)-3-methylbenzenesulfonamide, N-(4-(4-((2-(4-chlorophenyl)-1-cyclohexen-1-yl)methyl)
piperazin-1-yl)benzoyl)-4-(((1R)-3-(diisopropylamino)-
1-((phenylsulfanyl)methyl)propyl)amino)-3-nitrobenze-
nesulfonamide, N-(4-(4-((4'-chloro(1,1'-biphenyl)-2-yl)methyl)piperazin-1-
yl)benzoyl)-4-(((1R)-3-((2R,5R)-2,5-dimethylpyrrolidin-
1-yl)-1-((phenylsulfanyl)methyl)propyl)amino)-3-ni-
trobenzenesulfonamide, N-(4-(4-((4'-chloro(1,1'-biphenyl)-2-yl)methyl)piperazin-1-
yl)benzoyl)-4-(((1R)-3-((2S,5S)-2,5-dimethylpyrrolidin-
1-yl)-1-((phenylsulfanyl)methyl)propyl)amino)-3-ni-
trobenzenesulfonamide, N-(4-(4-((4'-chloro(1,1'-biphenyl)-2-yl)methyl)piperazin-1-
yl)benzoyl)-4-(((1R)-3-((2R,5S)-2,5-dimethylpyrrolidin-
1-yl)-1-((phenylsulfanyl)methyl)propyl)amino)-3-ni-
trobenzenesulfonamide, N-(4-(4-((4'-chloro(1,1'-biphenyl)-2-yl)methyl)piperazin-1-
yl)benzoyl)-4-(((1R)-3-(dimethylamino)-1-((phenylsulfa-
nyl)methyl)propyl)amino)-3-nitro-5-(trifluoromethyl)
benzenesulfonamide, N-(4-(4-((2-(4-chlorophenyl)-1-cyclohexen-1-yl)methyl)
piperazin-1-yl)benzoyl)-4-(((1R)-3-(dimethylamino)-1-
((phenylsulfanyl)methyl)propyl)amino)-3-nitro-5-(trif-
luoromethyl)benzenesulfonamide, N-(4-(4-((2-(4-chlorophenyl)-1-cyclohepten-1-yl)methyl)
piperazin-1-yl)benzoyl)-4-(((1R)-3-(dimethylamino)-1-
((phenylsulfanyl)methyl)propyl)amino)-3-nitro-5-(trif-
luoromethyl)benzenesulfonamide, N-(4-(4-((4'-chloro(1,1'-biphenyl)-2-yl)methyl)piperazin-1-
yl)benzoyl)-3-(((1R)-3-(dimethylamino)-1-((phenylsulfa-
nyl)methyl)propyl)amino)-4-nitrobenzenesulfonamide, N-(4-(4-((4'-chloro(1,1'-biphenyl)-2-yl)methyl)piperazin-1-
yl)benzoyl)-4-(((1R)-3-(dimethylamino)-1-((phenylsulfa-
nyl)methyl)propyl)amino)-3,5-difluorobenzenesulfona-
mide, methyl 5-(((4-(4-((4'-chloro(1,1'-biphenyl)-2-yl)methyl)pip-
erazin-1-yl)benzoyl)amino)sulfonyl)-2-(((1R)-3-(dim-
ethylamino)-1-((phenylsulfanyl)methyl)propyl)amino)-3-
nitrobenzoate, 5-(((4-(4-((4'-chloro(1,1'-biphenyl)-2-yl)methyl)piperazin-
1-yl)benzoyl)amino)sulfonyl)-2-(((1R)-3-(dimethy-
lamino)-1-((phenylsulfanyl)methyl)propyl)amino)-3-ni-
trobenzoic acid, 5-(((4-(4-((4'-chloro(1,1'-biphenyl)-2-yl)methyl)piperazin-
1-yl)benzoyl)amino)sulfonyl)-2-(((1R)-3-(dimethy-
lamino)-1-((phenylsulfanyl)methyl)propyl)amino)-3-ni-
trobenzoic acid, 5-(((4-(4-((2-(4-chlorophenyl)-1-cyclohexen-1-yl)methyl)
piperazin-1-yl)benzoyl)amino)sulfonyl)-2-(((1R)-3-(dim-
ethylamino)-1-((phenylsulfanyl)methyl)propyl)amino)-3-
nitrobenzoic acid, 5-(((4-(4-((2-(4-chlorophenyl)-1-cyclohexen-1-yl)methyl)
piperazin-1-yl)benzoyl)amino)sulfonyl)-2-(((1R)-3-(dim-
ethylamino)-1-((phenylsulfanyl)methyl)propyl)amino)-3-
nitrobenzamide, 5-(((4-(4-((4'-chloro(1,1'-biphenyl)-2-yl)methyl)piperazin-
1-yl)benzoyl)amino)sulfonyl)-2-(((1R)-3-(dimethy-
lamino)-1-((phenylsulfanyl)methyl)propyl)amino)-3-ni-
trobenzamide, methyl 5-(((4-(4-((2-(4-chlorophenyl)-1-cyclohexen-1-yl)
methyl)piperazin-1-yl)benzoyl)amino)sulfonyl)-2-
(((1R)-3-(dimethylamino)-1-((phenylsulfanyl)methyl)
propyl)amino)-3-(trifluoromethyl)benzoate, methyl 5-(((4-(4-((4-(4-chlorophenyl)-5,6-dihydro-2H-py-
ran-3-yl)methyl)piperazin-1-yl)benzoyl)amino)sulfonyl)-
2-(((1R)-3-(dimethylamino)-1-((phenylsulfanyl)methyl)
propyl)amino)-3-(trifluoromethyl)benzoate, methyl 5-(((4-(4-((4'-chloro(1,1'-biphenyl)-2-yl)methyl)pip-
erazin-1-yl)benzoyl)amino)sulfonyl)-2-(((1R)-3-(dim-
ethylamino)-1-((phenylsulfanyl)methyl)propyl)amino)-3-
(trifluoromethyl)benzoate, N-(4-(4-((2-(4-chlorophenyl)-1-cyclohexen-1-yl)methyl)
piperazin-1-yl)benzoyl)-4-(((1R)-4-((2R,5S)-2,5-dimeth-
ylpyrrolidin-1-yl)-1-((phenylsulfanyl)methyl)butyl)
amino)-3-nitrobenzenesulfonamide, N-(4-(4-((4-(4-chlorophenyl)-5,6-dihydro-2H-pyran-3-yl)
methyl)piperazin-1-yl)benzoyl)-4-(((1R)-4-((2R,5S)-2,5-
dimethylpyrrolidin-1-yl)-1-((phenylsulfanyl)methyl)bu-
tyl)amino)-3-nitrobenzenesulfonamide, tert-butyl 3-((4-(4-(((4-(((1R)-3-(dimethylamino)-1-((phe-
nylsulfanyl)methyl)propyl)amino)-3-nitrophenyl)sulfo-
nyl)amino)carbonyl)phenyl)piperazin-1-yl)carbonyl)phe-
nylcarbamate, N-(4-(4-(3-(dimethylamino)benzoyl)piperazin-1-yl)ben-
zoyl)-4-(((1R)-3-(dimethylamino)-1-((phenylsulfanyl)
methyl)propyl)amino)-3-nitrobenzenesulfonamide, N-(4-(4-((1,1'-biphenyl)-2-ylmethyl)piperazin-1-yl)ben-
zoyl)-4-(((1R)-3-(dimethylamino)-1-methyl-1-((phenyl-
sulfanyl)methyl)propyl)amino)-3-nitrobenzenesulfona-
mide, N-(4-(4-((1,1'-biphenyl)-2-ylmethyl)piperazin-1-yl)ben-
zoyl)-4-(((1S)-3-(dimethylamino)-1-methyl-1-((phenyl-
sulfanyl)methyl)propyl)amino)-3-nitrobenzenesulfona-
mide, N-(4-(4-(2-(1,3-dihydro-2H-isoindol-2-yl)benzyl)piper-
azin-1-yl)benzoyl)-4-(((1R)-3-(dimethylamino)-1-((phe-
nylsulfanyl)methyl)propyl)amino)-3-nitrobenzene-
sulfonamide, N-(4-(4-(2-(cyclohexylamino)benzyl)piperazin-1-yl)ben-
zoyl)-4-(((1R)-3-(dimethylamino)-1-((phenylsulfanyl)
methyl)propyl)amino)-3-nitrobenzenesulfonamide, 4-(((1R)-3-(dimethylamino)-1-((phenylsulfanyl)methyl)
propyl)amino)-N-(4-(4-(2-(isopropylamino)benzyl)piper-
azin-1-yl)benzoyl)-3-nitrobenzenesulfonamide, N-(4-(4-(2-(benzylamino)benzyl)piperazin-1-yl)benzoyl)-
4-(((1R)-3-(dimethylamino)-1-((phenylsulfanyl)methyl)
propyl)amino)-3-nitrobenzenesulfonamide, 4-(((1R)-3-(dimethylamino)-1-((phenylsulfanyl)methyl)
propyl)amino)-3-nitro-N-(4-(4-(2-(piperidin-1-yl)benzyl)
piperazin-1-yl)benzoyl)benzenesulfonamide, N-(4-(4-((1,1'-biphenyl)-2-ylmethyl)piperazin-1-yl)benzoyl)-3-nitro-4-((2-(phenylsulfanyl)ethyl)amino)benzenesulfonamide, N-(4-(4-((1,1'-biphenyl)-2-ylmethyl)piperazin-1-yl)benzoyl)-4-((cyclohexylmethyl)amino)-3-nitrobenzenesulfonamide, N-(4-(4-((1,1'-biphenyl)-2-ylmethyl)-4-methoxypiperidin-1-yl)benzoyl)-4-(((1R)-3-(morpholin-4-yl)-1-((phenylsulfanyl)methyl)propyl)amino)-3-nitrobenzenesulfonamide, N-(4-(4-((1,1'-biphenyl)-2-ylmethyl)-4-methoxypiperidin-1-yl)benzoyl)-3-nitro-4-((2-(phenylsulfanyl)ethyl)amino)benzenesulfonamide, N-(4-(4-((4'-chloro(1,1'-biphenyl)-2-yl)methyl)piperazin-1-yl)benzoyl)-4-(((1S)-3-(dimethylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-1-((phenylsulfanyl)methyl)-3-(pyrrolidin-1-yl)propyl)amino)-3-(trifluoromethyl)benzenesulfonamide, N-(4-(4-((4-(4-chlorophenyl)pyridin-3-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((4-(4-chlorophenyl)pyridin-3-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-2-fluoro-3-(trifluoromethyl)benzenesulfonamide, N-(6-(4-((4'-chloro(1,1'-biphenyl)-2-yl)methyl)piperazin-1-yl)-1,2-benzisoxazol-3-yl)-3-nitro-4-((2-(phenylsulfanyl)ethyl)amino)benzenesulfonamide, N-(6-(4-((4'-chloro(1,1'-biphenyl)-2-yl)methyl)piperazin-1-yl)-1,2-benzisoxazol-3-yl)-4-(((1R)-3-(morpholin-4-yl)-1-((phenylsulfanyl)methyl)propyl)amino)-3-nitrobenzenesulfonamide, N-(6-(4,4-dimethylpiperidin-1-yl)-1,2-benzisoxazol-3-yl)-3-nitro-4-((2-(phenylsulfanyl)ethyl)amino)benzenesulfonamide, N-(6-(4,4-dimethylpiperidin-1-yl)-1,2-benzisoxazol-3-yl)-4-(((1R)-3-(morpholin-4-yl)-1-((phenylsulfanyl)methyl)propyl)amino)-3-nitrobenzenesulfonamide, N-(6-(4-(3,3-diphenylpropen-2-yl)piperazin-1-yl)-1,2-benzisoxazol-3-yl)-4-(((1R)-3-(morpholin-4-yl)-1-((phenylsulfanyl)methyl)propyl)amino)-3-nitrobenzenesulfonamide, N-(6-(4-(3,3-diphenylpropen-2-yl)piperazin-1-yl)-1,2-benzisoxazol-3-yl)-3-nitro-4-((2-(phenylsulfanyl)ethyl)amino)benzenesulfonamide, N-(6-(4-((4'-chloro(1,1'-biphenyl)-2-yl)methyl)piperazin-1-yl)-1,2-benzisoxazol-3-yl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(6-(4,4-dimethylpiperidin-1-yl)-1,2-benzisoxazol-3-yl)-3-nitrobenzenesulfonamide, N-(6-(4-((4'-chloro(1,1'-biphenyl)-2-yl)methyl)piperazin-1-yl)-1-methyl-1H-indazol-3-yl)-3-nitro-4-((2-(phenylsulfanyl)ethyl)amino)benzenesulfonamide, N-(6-(4-((4'-chloro(1,1'-biphenyl)-2-yl)methyl)piperazin-1-yl)-1-methyl-1H-indazol-3-yl)-4-(((1,1-dimethyl-2-(phenylsulfanyl)ethyl)amino)-3-nitrobenzenesulfonamide, N-(6-(4-((4'-chloro(1,1'-biphenyl)-2-yl)methyl)piperazin-1-yl)-1-methyl-1H-indazol-3-yl)-4-(((1R)-3-(dimethylamino)-1-((phenylsulfanyl)methyl)propyl)amino)-3-nitrobenzenesulfonamide, N-(6-(4-((4'-chloro(1,1'-biphenyl)-2-yl)methyl)piperazin-1-yl)-1-methyl-1H-indazol-3-yl)-4-(((1R)-3-(morpholin-4-yl)-1-((phenylsulfanyl)methyl)propyl)amino)-3-nitrobenzenesulfonamide, N-(6-(4-((4'-chloro(1,1'-biphenyl)-2-yl)methyl)piperazin-1-yl)-1H-indazol-3-yl)-3-nitro-4-((2-(phenylsulfanyl)ethyl)amino)benzenesulfonamide, N-(6-(4-((4'-chloro(1,1'-biphenyl)-2-yl)methyl)piperazin-1-yl)-1H-indazol-3-yl)-4-(((1R)-3-(dimethylamino)-1-((phenylsulfanyl)methyl)propyl)amino)-3-nitrobenzenesulfonamide, and N-(6-(4-((4'-chloro(1,1'-biphenyl)-2-yl)methyl)piperazin-1-yl)-1H-indazol-3-yl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-(methylsulfonyl)-4-((2-(phenylsulfanyl)ethyl)amino)benzenesulfonamide, N-(4-(4-((4'-chloro(1,1'-biphenyl)-2-yl)methyl)piperazin-1-yl)benzoyl)-4-((1,1-dimethyl-2-(phenylsulfanyl)ethyl)amino)-3-(methylsulfonyl)benzenesulfonamide N-(4-(4-((4'-chloro(1,1'-biphenyl)-2-yl)methyl)piperazin-1-yl)benzoyl)-3-(methylsulfonyl)-4-(((1R)-3-(morpholin-4-yl)-1-((phenylsulfanyl)methyl)propyl)amino)benzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-(ethylsulfonyl)benzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-(methylsulfonyl)benzenesulfonamide, N-(4-(4-((4'-chloro(1,1'-biphenyl)-2-yl)methyl)piperazin-1-yl)benzoyl)-4-(((1R)-3-(diisopropylamino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(diisopropylamino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-((2R,5S)-2,5-dimethylpyrrolidin-1-yl)-1-((phenylsulfanyl)methyl)propyl)amino)-3-((trifluoromethyl)sulfonyl)benzenesulfonamide, 4-(((1R)-4-(7-azabicyclo[2.2.1]hept-7-yl)-1-((phenylsulfanyl)methyl)butyl)amino)-N-(4-(4-((2-(4-chlorophenyl)cyclohex-1-en-1-yl)methyl)piperazin-1-yl)benzoyl)-3-((trifluoromethyl)sulfonyl)benzenesulfonamide, 4-(((1R)-4-(7-azabicyclo[2.2.1]hept-7-yl)-1-((phenylsulfanyl)methyl)butyl)amino)-N-(4-(4-((4-(4-chlorophenyl)-5,6-dihydro-2H-pyran-3-yl)methyl)piperazin-1-yl)benzoyl)-3-((trifluoromethyl)sulfonyl)benzenesulfonamide, N-(4-(4-((4-(4-chlorophenyl)-5,6-dihydro-2H-pyran-3-yl)methyl)piperazin-1-yl)benzoyl)-4-(((1R)-4-((2R,5S)-2,5-dimethylpyrrolidin-1-yl)-1-((phenylsulfanyl)methyl)butyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-4-(diisopropylamino)-1-((phenylsulfanyl)methyl)butyl)amino)-3-((trifluoromethyl)sulfonyl)benzenesulfonamide, N-(4-(4-((4-(4-chlorophenyl)-5,6-dihydro-2H-pyran-3-yl)
methyl)piperazin-1-yl)benzoyl)-4-(((1R)-4-(diisopropy-
lamino)-1-((phenylsulfanyl)methyl)butyl)amino)-3-((trif-
luoromethyl)sulfonyl)benzenesulfonamide, N-(4-(4-((2-(4-chlorophenyl)cyclohex-1-en-1-yl)methyl)
piperazin-1-yl)benzoyl)-4-(((1R)-4-(dimethylamino)-1-
((phenylsulfanyl)methyl)butyl)amino)-3-((trifluorom-
ethyl)sulfonyl)benzenesulfonamide, N-(4-(4-((4-(4-chlorophenyl)-5,6-dihydro-2H-pyran-3-yl)
methyl)piperazin-1-yl)benzoyl)-4-(((1R)-4-(dimethy-
lamino)-1-((phenylsulfanyl)methyl)butyl)amino)-3-((trif-
luoromethyl)sulfonyl)benzenesulfonamide, N-(4-(4-((2-(4-chlorophenyl)cyclohex-1-en-1-yl)methyl)
piperazin-1-yl)benzoyl)-4-(((1R)-4-((2R,5S)-2,5-dimeth-
ylpyrrolidin-1-yl)-1-((phenylsulfanyl)methyl)butyl)
amino)-3-((trifluoromethyl)sulfonyl)
benzenesulfonamide, 4-(((1R)-3-(1-azetidinyl)-1-((phenylsulfanyl)methyl)pro-
pyl)amino)-N-(4-(4-((2-(4-chlorophenyl)cyclohex-1-en-
1-yl)methyl)piperazin-1-yl)benzoyl)-3-((trifluoromethyl)
sulfonyl)benzenesulfonamide, 4-(((1R)-3-(1-azetidinyl)-1-((phenylsulfanyl)methyl)pro-
pyl)amino)-N-(4-(4-((4-(4-chlorophenyl)-5,6-dihydro-
2H-pyran-3-yl)methyl)piperazin-1-yl)benzoyl)-3-((trif-
luoromethyl)sulfonyl)benzenesulfonamide, 4-(((1R)-3-((3aR,6aS)-tetrahydro-1H-furo[3,4-c]pyrrol-5
(3H)-yl)-1-((phenylsulfanyl)methyl)propyl)amino)-N-(4-
(4-((2-(4-chlorophenyl)cyclohex-1-en-1-yl)methyl)piper-
azin-1-yl)benzoyl)-3-((trifluoromethyl)sulfonyl)
benzenesulfonamide, 4-(((1R)-3-((3aR,6aS)-tetrahydro-1H-furo[3,4-c]pyrrol-5
(3H)-yl)-1-((phenylsulfanyl)methyl)propyl)amino)-N-(4-
(4-((4-(4-chlorophenyl)-5,6-dihydro-2H-pyran-3-yl)me-
thyl)piperazin-1-yl)benzoyl)-3-((trifluoromethyl)
sulfonyl)benzenesulfonamide, N-(4-(4-((2-(4-chlorophenyl)cyclohex-1-en-1-yl)methyl)
piperazin-1-yl)benzoyl)-4-(((1R)-3-(8-oxa-3-azabicyclo
[3.2.1]    oct-3-yl)-1-((phenylsulfanyl)methyl)propyl)
amino)-3-((trifluoromethyl)sulfonyl)
benzenesulfonamide, N-(4-(4-((4-(4-chlorophenyl)-5,6-dihydro-2H-pyran-3-yl)
methyl)piperazin-1-yl)benzoyl)-4-(((1R)-3-(8-oxa-3-
azabicyclo[3.2.1]    oct-3-yl)-1-((phenylsulfanyl)methyl)
propyl)amino)-3-((trifluoromethyl)sulfonyl)
benzenesulfonamide, N-(4-(4-((2-(4-chlorophenyl)cyclohex-1-en-1-yl)methyl)
piperazin-1-yl)benzoyl)-4-(((1R)-4-(morpholin-4-yl)-1-
((phenylsulfanyl)methyl)butyl)amino)-3-((trifluorom-
ethyl)sulfonyl)benzenesulfonamide, N-(4-(4-((2-(4-chlorophenyl)-5,5-dimethylcyclohex-1-en-1-
yl)methyl)piperazin-1-yl)benzoyl)-4-(((1R)-4-(morpho-
lin-4-yl)-1-((phenylsulfanyl)methyl)butyl)amino)-3-((tri-
fluoromethyl)sulfonyl)benzenesulfonamide, N-(4-((3R,5S)-4-((4'-chloro(1,1'-biphenyl)-2-yl)methyl)-3,
5-dimethylpiperazinyl)benzoyl)-4-(((1R)-3-(isopropyl
(methyl)amino)-1-((phenylsulfanyl)methyl)propyl)
amino)-3-((trifluoromethyl)sulfonyl)
benzenesulfonamide, N-(4-((3R,5S)-4-((4'-chloro(1,1'-biphenyl)-2-yl)methyl)-3,
5-dimethylpiperazinyl)benzoyl)-3-((chloro(difluoro)me-
thyl)sulfonyl)-4-(((1R)-3-((1S,4S)-2-oxa-5-azabicyclo
[2.2.1]hept-5-yl)-1-((phenylsulfanyl)methyl)propyl)
amino)benzenesulfonamide, 4-(((1R)-3-(7-azabicyclo[2.2.1]hept-7-yl)-1-((phenylsulfa-
nyl)methyl)propyl)amino)-N-(4-(4-((2-(4-chlorophenyl)-
1-cyclohepten-1-yl)methyl)piperazin-1-yl)benzoyl)-3-
((trifluoromethyl)sulfonyl)benzenesulfonamide, N-(4-(4-((4-(4-chlorophenyl)-5,6-dihydro-2H-pyran-3-yl)
methyl)piperazin-1-yl)benzoyl)-4-(((1R)-3-(2-oxa-5-
azabicyclo[2.2.1]hept-5-yl)-1-((phenylsulfanyl)methyl)
propyl)amino)-3-((trifluoromethyl)sulfonyl)
benzenesulfonamide, 4-(((1R)-3-(7-azabicyclo[2.2.1]hept-7-yl)-1-((phenylsulfa-
nyl)methyl)propyl)amino)-N-(4-(4-((4-(4-chlorophenyl)-
5,6-dihydro-2H-pyran-3-yl)methyl)piperazin-1-yl)ben-
zoyl)-3-((trifluoromethyl)sulfonyl)benzenesulfonamide, N-(4-(4-((2-(4-chlorophenyl)cyclohex-1-en-1-yl)methyl)
piperazin-1-yl)benzoyl)-4-(((1R)-1-((phenylsulfanyl)me-
thyl)-3-(pyrrolidin-1-yl)propyl)amino)-3-((trifluorom-
ethyl)sulfonyl)benzenesulfonamide, 4-(((1R)-3-((1S,4R)-2-azabicyclo[2.2.1]hept-2-yl)-1-((phe-
nylsulfanyl)methyl)propyl)amino)-N-(4-(4-((2-(4-chlo-
rophenyl)cyclohex-1-en-1-yl)methyl)piperazin-1-yl)ben-
zoyl)-3-((trifluoromethyl)sulfonyl)benzenesulfonamide, N-(4-(4-((4'-chloro(1,1'-biphenyl)-2-yl)methyl)piperazin-1-
yl)benzoyl)-4-(((1R)-3-hydroxy-1-((phenylsulfanyl)me-
thyl)propyl)amino)-3-(methylsulfonyl)benzenesulfona-
mide, N-(4-(4-((4'-chloro(1,1'-biphenyl)-2-yl)methyl)piperazin-1-
yl)benzoyl)-4-(((1R)-3-(diisopropylamino)-1-((phenyl-
sulfanyl)methyl)propyl)amino)-3-(methylsulfonyl)benze-
nesulfonamide, N-(4-(4-((4'-chloro(1,1'-biphenyl)-2-yl)methyl)piperazin-1-
yl)benzoyl)-3-(methylsulfonyl)-4-(((1R)-1-((phenylsulfa-
nyl)methyl)-3-(pyrrolidin-1-yl)propyl)amino)benzene-
sulfonamide, (3R)-3-(4-(((4-(4-((4'-chloro(1,1'-biphenyl)-2-yl)methyl)
piperazin-1-yl)benzoyl)amino)sulfonyl)-2-(methylsulfo-
nyl)anilino)-N,N-diisopropyl-4-(phenylsulfanyl)butana-
mide (3R)-3-(4-(((4-(4-((4'-chloro(1,1'-biphenyl)-2-yl)methyl)
piperazin-1-yl)benzoyl)amino)sulfonyl)-2-(methylsulfo-
nyl)anilino)-N-isopropyl-N-methyl-4-(phenylsulfanyl)
butanamide 4-(((1R)-3-(azetidin-1-yl)-3-oxo-1-((phenylsulfanyl)me-
thyl)propyl)amino)-N-(4-(4-((4'-chloro(1,1'-biphenyl)-2-
yl)methyl)piperazin-1-yl)benzoyl)-3-(methylsulfonyl)
benzenesulfonamide, N-(4-(4-((4'-chloro(1,1'-biphenyl)-2-yl)methyl)piperazin-1-
yl)benzoyl)-4-(((1R)-3-(diethylamino)-1-((phenylsulfa-
nyl)methyl)propyl)amino)-3-(methylsulfonyl)benzene-
sulfonamide, N-(4-(4-((4'-chloro(1,1'-biphenyl)-2-yl)methyl)piperazin-1-
yl)benzoyl)-4-(((1R)-3-(isopropyl(methyl)amino)-1-
((phenylsulfanyl)methyl)propyl)amino)-3-(methylsulfo-
nyl)benzenesulfonamide, 4-(((1R)-3-(azetidin-1-yl)-1-((phenylsulfanyl)methyl)pro-
pyl)amino)-N-(4-(4-((4'-chloro(1,1'-biphenyl)-2-yl)me-
thyl)piperazin-1-yl)benzoyl)-3-(methylsulfonyl)benzene-
sulfonamide, N-(4-(4-((4'-chloro(1,1'-biphenyl)-2-yl)methyl)piperazin-1-
yl)benzoyl)-3-(methylsulfonyl)-4-(((1R)-3-oxo-1-((phe-
nylsulfanyl)methyl)-3-(pyrrolidin-1-yl)propyl)amino)
benzenesulfonamide, N-(4-(4-((4'-chloro(1,1'-biphenyl)-2-yl)methyl)piperazin-1-
yl)benzoyl)-4-(((1R)-3-(dimethylamino)-1-((phenylsulfa-
nyl)methyl)propyl)amino)-3-((1,1,2,2,2-pentafluoroet-
hyl)sulfonyl)benzenesulfonamide, N-(4-(4-((4'-chloro(1,1'-biphenyl)-2-yl)methyl)piperazin-1-
yl)benzoyl)-4-(((1R)-3-(dimethylamino)-1-((phenylsulfa-
nyl)methyl)propyl)amino)-3-((1,1,2,2,3,3,3-heptafluoro-
propyl)sulfonyl)benzenesulfonamide, N-(4-(4-((4'-chloro(1,1'-biphenyl)-2-yl)methyl)piperazin-1-
yl)benzoyl)-4-(((1R)-3-(dimethylamino)-1-((phenylsulfanyl)methyl)propyl)amino)-3-((1,2,2,2-tetrafluoro-1-(trifluoromethyl)ethyl)sulfonyl)benzenesulfonamide, N-(4-(4-((4'-chloro(1,1'-biphenyl)-2-yl)methyl)piperazin-1-yl)benzoyl)-4-(((1R)-3-(4,4-dimethyl-4,5-dihydro-1H-imidazol-1-yl)-1-((phenylsulfanyl)methyl)propyl)amino)-3-((trifluoromethyl)sulfonyl)benzenesulfonamide, N-(4-(4-((4'-chloro(1,1'-biphenyl)-2-yl)methyl)piperazin-1-yl)benzoyl)-4-(((1R)-3-(5,6-dihydro-1(4H)-pyrimidin-1-yl)-1-((phenylsulfanyl)methyl)propyl)amino)-3-((trifluoromethyl)sulfonyl)benzenesulfonamide, N-(4-(4-((4'-chloro(1,1'-biphenyl)-2-yl)methyl)piperazin-1-yl)benzoyl)-4-(((1R)-3-(2,4-dimethyl-4,5-dihydro-1H-imidazol-1-yl)-1-((phenylsulfanyl)methyl)propyl)amino)-3-((trifluoromethyl)sulfonyl)benzenesulfonamide, N-(4-(4-((4'-chloro(1,1'-biphenyl)-2-yl)methyl)piperazin-1-yl)benzoyl)-4-(((1R)-3-(2-methyl-4,5-dihydro-1H-imidazol-1-yl)-1-((phenylsulfanyl)methyl)propyl)amino)-3-((trifluoromethyl)sulfonyl)benzenesulfonamide, N-(4-(4-((4'-chloro(1,1'-biphenyl)-2-yl)methyl)piperazin-1-yl)benzoyl)-4-(((1R)-3-(2,5-dimethylpyrrolidin-1-yl)-1-((phenylsulfanyl)methyl)propyl)amino)-3-((trifluoromethyl)sulfonyl)benzenesulfonamide, N-(4-(4-((4'-chloro(1,1'-biphenyl)-2-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, N-(4-(4-((2-(4-chlorophenyl)cyclohept-1-en-1-yl)methyl)piperazin-1-yl)benzoyl)-4-(((1R)-3-(diisopropylamino)-1-((phenylsulfanyl)methyl)propyl)amino)-3-((trifluoromethyl)sulfonyl)benzenesulfonamide, 4-(((1R)-3-(bis(2-methoxyethyl)amino)-1-((phenylsulfanyl)methyl)propyl)amino)-N-(4-(4-((2-(4-chlorophenyl)cyclohex-1-en-1-yl)methyl)piperazin-1-yl)benzoyl)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(1,4,7-dioxazonan-7-yl)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(2-methylpyrrolidin-1-yl)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(4,4-difluoropiperidin-1-yl)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-((3R,5S)-3,5-dimethoxypiperidin-1-yl)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-((2S)-2-(methoxymethyl)pyrrolidin-1-yl)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-1-((phenylsulfanyl)methyl)-3-(1,3-thiazolidin-3-yl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-((3S)-3-methylmorpholin-4-yl)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(1-hydroxy-3,7-dioxa-9-azabicyclo[3.3.1]non-9-yl)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1S)-3-(3,7-dioxa-9-azabicyclo[3.3.1]non-9-yl)-1-(2-phenylethyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-3-((difluoromethyl)sulfonyl)-4-(((1R)-3-(morpholin-4-yl)-1-((phenylsulfanyl)methyl)propyl)amino)benzenesulfonamide, N-(4-(4-((2-(4-chlorophenyl)cyclohex-1-en-1-yl)methyl)piperazin-1-yl)benzoyl)-3-((difluoromethyl)sulfonyl)-4-(((1R)-3-(dimethylamino)-1-((phenylsulfanyl)methyl)propyl)amino)benzenesulfonamide, N-(4-(4-((2-(4-chlorophenyl)cyclohex-1-en-1-yl)methyl)piperazin-1-yl)benzoyl)-4-(((1R)-3-(dimethylamino)-1-((phenylsulfanyl)methyl)propyl)oxy)-3-(ethylsulfonyl)benzenesulfonamide, 3-((chloro(difluoro)methyl)sulfonyl)-N-(4-(4-((4-(4-chlorophenyl)-5,6-dihydro-2H-pyran-3-yl)methyl)piperazin-1-yl)benzoyl)-4-(((1R)-3-(dimethylamino)-1-((phenylsulfanyl)methyl)propyl)amino)benzenesulfonamide, N-(4-(4-((4-(4-chlorophenyl)-5,6-dihydro-2H-pyran-3-yl)methyl)piperazin-1-yl)benzoyl)-3-((difluoromethyl)sulfonyl)-4-(((1R)-3-(dimethylamino)-1-((phenylsulfanyl)methyl)propyl)amino)benzenesulfonamide, 3-((chloro(difluoro)methyl)sulfonyl)-N-(4-(4-((4-(4-chlorophenyl)-5,6-dihydro-2H-pyran-3-yl)methyl)piperazin-1-yl)benzoyl)-4-(((1R)-3-(morpholin-4-yl)-1-((phenylsulfanyl)methyl)propyl)amino)benzenesulfonamide, N-(4-(4-((4-(4-chlorophenyl)-5,6-dihydro-2H-pyran-3-yl)methyl)piperazin-1-yl)benzoyl)-4-(((1R)-3-(dimethylamino)-1-((phenylsulfanyl)methyl)propyl)oxy)-3-(ethylsulfonyl)benzenesulfonamide, N-(4-(4-((4-(4-chlorophenyl)-5,6-dihydro-2H-pyran-3-yl)methyl)piperazin-1-yl)benzoyl)-3-((difluoromethyl)sulfonyl)-4-(((1R)-3-(morpholin-4-yl)-1-((phenylsulfanyl)methyl)propyl)amino)benzenesulfonamide, N-(4-(4-((2-(4-chlorophenyl)-5,5-dimethylcyclohex-1-en-1-yl)methyl)piperazin-1-yl)benzoyl)-4-(((1R)-3-(1,4-oxazepan-4-yl)-1-((phenylsulfanyl)methyl)propyl)amino)-3-((trifluoromethyl)sulfonyl)benzenesulfonamide, N-(4-(4-((2-(4-chlorophenyl)cyclohept-1-en-1-yl)methyl)piperazin-1-yl)benzoyl)-4-(((1R)-3-(1,4-oxazepan-4-yl)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(dimethylamino)-1-((phenylsulfanyl)methyl)propyl)amino)benzenesulfonamide, 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(morpholin-4-yl)-1-((phenylsulfanyl)methyl)propyl)amino)benzenesulfonamide, 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(dimethylamino)-1-((phenylsulfanyl)methyl)propyl)amino)benzenesulfonamide, 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-(1,4-oxazepan-4-yl)-1-((phenylsulfanyl)methyl)propyl)amino)benzenesulfonamide, 3-((chloro(difluoro)methyl)sulfonyl)-N-(4-(4-((2-(4-chlorophenyl)cyclohept-1-en-1-yl)methyl)piperazin-1-yl)

benzoyl)-4-(((1R)-3-(1,4-oxazepan-4-yl)-1-((phenylsulfanyl)methyl)propyl)amino)benzenesulfonamide, 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(1,4-oxazepan-4-yl)-1-((phenylsulfanyl)methyl)propyl)amino)benzenesulfonamide, 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(1,4-oxazepan-4-yl)-1-((phenylsulfanyl)methyl)propyl)amino)benzenesulfonamide, 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-(isopropyl(methyl)amino)-1-((phenylsulfanyl)methyl)propyl)amino)benzenesulfonamide, 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(isopropyl(methyl)amino)-1-((phenylsulfanyl)methyl)propyl)amino)benzenesulfonamide, N-(4-(4-((2-(4-chlorophenyl)-4,4-dimethylcyclohex-1-en-1-yl)methyl)piperazin-1-yl)benzoyl)-4-(((1R)-3-(1,4-oxazepan-4-yl)-1-((phenylsulfanyl)methyl)propyl)amino)-3-((trifluoromethyl)sulfonyl)benzenesulfonamide, N-(4-(4-((4-(4-chlorophenyl)-5,6-dihydro-2H-pyran-3-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, 4-(((1R)-3-(7-azabicyclo[2.2.1]hept-7-yl)-1-((phenylsulfanyl)methyl)propyl)amino)-N-(4-(4-((2-(4-chlorophenyl)-5,5-dimethylcyclohex-1-en-1-yl)methyl)piperazin-1-yl)benzoyl)-3-((trifluoromethyl)sulfonyl)benzenesulfonamide, N-(4-(4-((4-(4-chlorophenyl)-5,6-dihydro-2H-pyran-3-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, tert-butyl 4-(4-chlorophenyl)-5-((4-(4-(((((4-(((1R)-3-(morpholin-4-yl)-1-((phenylsulfanyl)methyl)propyl)amino)-3-((trifluoromethyl)sulfonyl)phenyl)sulfonyl)amino)carbonyl)phenyl)piperazin-1-yl)methyl)-3,6-dihydro-1(2H)-pyridinecarboxylate tert-butyl 4-(4-chlorophenyl)-5-((4-(4-(((((4-(((1R)-3-(dimethylamino)-1-((phenylsulfanyl)methyl)propyl)amino)-3-((trifluoromethyl)sulfonyl)phenyl)sulfonyl)amino)carbonyl)phenyl)piperazin-1-yl)methyl)-3,6-dihydro-1(2H)-pyridinecarboxylate N-(4-(4-((4-(4-chlorophenyl)-1,2,5,6-tetrahydro-3-pyridinyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((4-(4-chlorophenyl)-1,2,5,6-tetrahydro-3-pyridinyl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, N-(4-(4-((1-acetyl-4-(4-chlorophenyl)-1,2,5,6-tetrahydro-3-pyridinyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((4-(4-chlorophenyl)-1-methyl-1,2,5,6-tetrahydro-3-pyridinyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((4-(4-chlorophenyl)-1-(cyclohexylmethyl)-1,2,5,6-tetrahydro-3-pyridinyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((1-acetyl-4-(4-chlorophenyl)-1,2,5,6-tetrahydro-3-pyridinyl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, N-(4-(4-((4-(4-chlorophenyl)-1-methyl-1,2,5,6-tetrahydro-3-pyridinyl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, N-(4-(4-((2-(4-chlorophenyl)-4,4-dimethylcyclohex-1-en-1-yl)methyl)piperazin-1-yl)benzoyl)-4-(((1R)-3-(diethylamino)-1-((phenylsulfanyl)methyl)propyl)amino)-3-((trifluoromethyl)sulfonyl)benzenesulfonamide, N-(4-(4-(((1R,2R)-2-(4-chlorophenyl)cyclohexyl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, 3-((chloro(difluoro)methyl)sulfonyl)-4-(((1R)-3-(morpholin-4-yl)-1-((phenylsulfanyl)methyl)propyl)amino)-N-(4-(4-((4-(4-(trifluoromethyl)phenyl)-5,6-dihydro-2H-pyran-3-yl)methyl)piperazin-1-yl)benzoyl)benzenesulfonamide, 4-(((1R)-3-(morpholin-4-yl)-1-((phenylsulfanyl)methyl)propyl)amino)-N-(4-(4-((4-(4-(trifluoromethyl)phenyl)-5,6-dihydro-2H-pyran-3-yl)methyl)piperazin-1-yl)benzoyl)-3-((trifluoromethyl)sulfonyl)benzenesulfonamide, 3-((chloro(difluoro)methyl)sulfonyl)-N-(4-(4-((2-(4-chlorophenyl)-4,4-diethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide, N-(4-(1-((4'-chloro(1,1'-biphenyl)-2-yl)methyl)-1,2,3,6-tetrahydropyridin-4-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(1-((4'-chloro(1,1'-biphenyl)-2-yl)methyl)-1,2,3,6-tetrahydropyridin-4-yl)benzoyl)-4-(((1R)-3-(morpholin-4-yl)-1-((phenylsulfanyl)methyl)propyl)amino)-3-((trifluoromethyl)sulfonyl)benzenesulfonamide, N-(4-(1-((4'-chloro(1,1'-biphenyl)-2-yl)methyl)-1,2,3,6-tetrahydropyridin-4-yl)benzoyl)-4-(((1R)-3-(diisopropylamino)-1-((phenylsulfanyl)methyl)propyl)amino)-3-((trifluoromethyl)sulfonyl)benzenesulfonamide, N-(4-(1-((4'-chloro(1,1'-biphenyl)-2-yl)methyl)-1,2,3,6-tetrahydropyridin-4-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, N-(4-(1-((2-(4-chlorophenyl)-1-cyclohex-1-en-1-yl)methyl)-1,2,3,6-tetrahydropyridin-4-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(1-((2-(4-chlorophenyl)-1-cyclohex-1-en-1-yl)methyl)-1,2,3,6-tetrahydropyridin-4-yl)benzoyl)-4-(((1R)-3-(morpholin-4-yl)-1-((phenylsulfanyl)methyl)propyl)amino)-3-((trifluoromethyl)sulfonyl)benzenesulfonamide, N-(4-(1-((2-(4-chlorophenyl)-1-cyclohex-1-en-1-yl)methyl)-1,2,3,6-tetrahydropyridin-4-yl)benzoyl)-4-(((1R)-3-(diisopropylamino)-1-((phenylsulfanyl)methyl)propyl)amino)-3-((trifluoromethyl)sulfonyl)benzenesulfonamide, N-(4-(1-((2-(4-chlorophenyl)-1-cyclohex-1-en-1-yl)methyl)-1,2,3,6-tetrahydropyridin-4-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, N-(4-(1-((2-(4-chlorophenyl)-1-cyclohept-1-en-1-yl)methyl)-1,2,3,6-tetrahydropyridin-4-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(1-((2-(4-chlorophenyl)-1-cyclohept-1-en-1-yl)methyl)-1,2,3,6-tetrahydropyridin-4-yl)benzoyl)-4-(((1R)-3-(morpholin-4-yl)-1-((phenylsulfanyl)methyl)propyl)amino)-3-((trifluoromethyl)sulfonyl)benzenesulfonamide, N-(4-(1-((4'-chloro(1,1'-biphenyl)-2-yl)methyl)piperidin-4-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((4'-chloro(1,1'-biphenyl)-2-yl)methyl)piperidin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((4'-chloro(1,1'-biphenyl)-2-yl)methyl)-1-cyclohex-1-en-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((2-(4-chlorophenyl)cyclohept-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-2-(dimethylamino)-1-((phenylsulfanyl)methyl)ethyl)amino)-3-((trifluoromethyl)sulfonyl)benzenesulfonamide, N-(4-(4-((4'-chloro(1,1'-biphenyl)-2-yl)methyl)piperazin-1-yl)benzoyl)-4-(((1R)-2-(dimethylamino)-1-((phenylsulfanyl)methyl)ethyl)amino)-3-((trifluoromethyl)sulfonyl)benzenesulfonamide, N-(4-(4-((4'-chloro(1,1'-biphenyl)-2-yl)methyl)piperazin-1-yl)benzoyl)-4-(((1R)-2-(diethylamino)-1-((phenylsulfanyl)methyl)ethyl)amino)-3-((trifluoromethyl)sulfonyl)benzenesulfonamide, N-(4-(4-((4'-chloro(1,1'-biphenyl)-2-yl)methyl)piperazin-1-yl)benzoyl)-4-(((1R)-2-(morpholin-4-yl)-1-((phenylsulfanyl)methyl)ethyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-2-(diethylamino)-1-((phenylsulfanyl)methyl)ethyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-2-(morpholin-4-yl)-1-((phenylsulfanyl)methyl)ethyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-((2R,6S)-2,6-dimethylmorpholin-1-yl)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(2,6-dimethylmorpholin-4-yl)-1-((phenylsulfanyl)methyl)propyl)amino)-3-((trifluoromethyl)sulfonyl)benzenesulfonamide, N-(4-(4-((2-(4-chlorophenyl)cyclohept-1-en-1-yl)methyl)piperazin-1-yl)benzoyl)-4-(((1R)-3-((2R,6S)-2,6-dimethylmorpholin-4-yl)-1-((phenylsulfanyl)methyl)propyl)amino)-3-((trifluoromethyl)sulfonyl)benzenesulfonamide, N-(4-(4-((2-(4-chlorophenyl)cyclohept-1-en-1-yl)methyl)piperazin-1-yl)benzoyl)-4-(((1R)-3-(2,6-dimethylmorpholin-4-yl)-1-((phenylsulfanyl)methyl)propyl)amino)-3-((trifluoromethyl)sulfonyl)benzenesulfonamide, N-(4-(4-((1-(4-chlorophenyl)piperidin-2-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(cyclopropylamino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(cyclopropyl(cyclopropylmethyl)amino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(cyclopropyl(methyl)amino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-((cyclopentylmethyl)(cyclopropyl)amino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-((cyclohexylmethyl)(cyclopropyl)amino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(cyclopropyl(tetrahydrofuran-3-ylmethyl)amino)-1-((phenylsulfanyl)methyl)propyl)amino)-3-((trifluoromethyl)sulfonyl)benzenesulfonamide, 4-(((1R)-3-(benzyl(cyclopropyl)amino)-1-((phenylsulfanyl)methyl)propyl)amino)-N-(4-(4-((2-(4-chlorophenyl)cyclohex-1-en-1-yl)methyl)piperazin-1-yl)benzoyl)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(cyclopropyl(isobutyl)amino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(cyclopropyl(tetrahydro-2H-pyran-4-yl)amino)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)-4,4-diethylcyclohex-1-en-1-yl)methyl)piperazin-1-yl)benzoyl)-4-(((1R)-3-(dimethylamino)-1-((phenylsulfanyl)methyl)propyl)amino)benzenesulfonamide, N-(4-(4-((2-(4-chlorophenyl)-4,4-diethylcyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, (4-(cyclohexylmethoxy)-N-((4'-fluoro(1,1'-biphenyl)-4-yl)carbonyl)-3-(methylsulfonyl)benzenesulfonamide, N-(4-(4-(((1R,2R)-2-(4-chlorophenyl)cyclohexyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-(((1S,2S)-2-(4-chlorophenyl)cyclohexyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-(((1R,2S)-2-(4-chlorophenyl)cyclohexyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-(((1S,2S)-2-(4-chlorophenyl)cyclohexyl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, N-(4-(4-(((1R,2S)-2-(4-chlorophenyl)cyclohexyl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, N-(4-(4-((4'-chloro(1,1'-biphenyl)-2-yl)methyl)piperazin-1-yl)benzoyl)-4-(((1R)-3-(dipropylamino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(dipropylamino)-1-((phenylsulfanyl)methyl)propyl)amino)-3-((trifluoromethyl)sulfonyl)benzenesulfonamide, N-(4-(4-((4'-chloro(1,1'-biphenyl)-2-yl)methyl)piperazin-1-yl)benzoyl)-4-(((1R)-3-(diethylamino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(diethylamino)-1-((phenylsulfanyl)methyl)propyl)amino)-3-((trifluoromethyl)sulfonyl)benzenesulfonamide, N-(4-(4-((2-(4-chlorophenyl)-5,5-dimethylcyclohex-1-en-1-yl)methyl)piperazin-1-yl)benzoyl)-4-(((1R)-3-(diethylamino)-1-((phenylsulfanyl)methyl)propyl)amino)-3-((trifluoromethyl)sulfonyl)benzenesulfonamide, N-(4-(4-((2-(4-chlorophenyl)cyclohept-1-en-1-yl)methyl)piperazin-1-yl)benzoyl)-4-(((1R)-3-(diethylamino)-1-((phenylsulfanyl)methyl)propyl)amino)-3-((trifluoromethyl)sulfonyl)benzenesulfonamide, N-(4-(4-((4'-chloro(1,1'-biphenyl)-2-yl)methyl)piperazin-1-yl)benzoyl)-3-((chloro(difluoro)methyl)sulfonyl)-4-(((1R)-3-(diethylamino)-1-((phenylsulfanyl)methyl)propyl)amino)benzenesulfonamide, 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-(diethylamino)-1-((phenylsulfanyl)methyl)propyl)amino)benzenesulfonamide, 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(diethylamino)-1-((phenylsulfanyl)methyl)propyl)amino)benzenesulfonamide, ((((4-chlorobutyl)((3R)-3-(4-(((4-(4-((2-(4-chlorophenyl)-1-cyclohexen-1-yl)methyl)-1-piperazinyl)benzoyl)amino)sulfonyl)-2-((trifluoromethyl)sulfonyl)anilino)-4-(phenylsulfanyl)butyl)amino)carbonyl)oxy)methyl pivalate, (phosphonooxy)methyl 4-chlorobutyl((3R)-3-(4-(((4-(4-((2-(4-chlorophenyl)-1-cyclohexen-1-yl)methyl)-1-piperazinyl)benzoyl)amino)sulfonyl)-2-((trifluoromethyl)sulfonyl)anilino)-4-(phenylsulfanyl)butyl)carbamate, N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide, 3-((chloro(difluoro)methyl)sulfonyl)-N-(4-(4-((2-(4-chlorophenyl)-1-cyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide, N-(4-(4-((2-(4-chlorophenyl)-5,5-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, N-(4-(4-((2-(4-chlorophenyl)-1-cyclohepten-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)benzenesulfonamide, N-(4-(4-((2-(4-chlorophenyl)cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, 4-(((1R)-3-(7-azabicyclo[2.2.1]hept-7-yl)-1-((phenylsulfanyl)methyl)propyl)amino)-N-(4-(4-((2-(4-chlorophenyl)cyclohex-1-en-1-yl)methyl)piperazin-1-yl)benzoyl)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide, N-(4-(4-((2-(4-chlorophenyl)-5,5-dimethylcyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)benzenesulfonamide, N-(4-(4-((2-(4-chlorophenyl)cyclohept-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)benzenesulfonamide, N-(4-(4-((2-(4-chlorophenyl)-4,4-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(1,4-oxazepan-4-yl)-1-((phenylsulfanyl)methyl)propyl)amino)-3-((trifluoromethyl)sulfonyl)benzenesulfonamide, 4-(((1R)-3-(azepan-1-yl)-1-((phenylsulfanyl)methyl)propyl)amino)-N-(4-(4-((2-(4-chlorophenyl)-1-cyclohex-1-en-1-yl)methyl)piperazin-1-yl)benzoyl)-3-((trifluoromethyl)sulfonyl)benzenesulfonamide, N-(4-(4-((2-(4-chlorophenyl)cyclohept-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-(dimethylamino)-1-((phenylsulfanyl)methyl)propyl)amino)benzenesulfonamide, 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide, N-(4-(4-((2-(4-chlorophenyl)-5,5-dimethyl-1-cyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((4-(4-chlorophenyl)-5,6-dihydro-2H-pyran-3-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)benzenesulfonamide, 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)benzenesulfonamide, N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)benzenesulfonamide, N-(4-(4-((2-(4-chlorophenyl)cyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide, 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)benzenesulfonamide, N-(4-(4-((2-(4-chlorophenyl)cyclohept-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide, 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, N-(4-(4-((2-(4-chlorophenyl)cyclohex-1-en-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, N-(4-(4-((2-(4-chlorophenyl)-4,4-dimethylcyclohex-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide, 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((2-(4-chlorophenyl)-4,4-dimethylcyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)-3-((trifluoromethyl)sulfonyl)benzenesulfonamide N-(4-(4-((4'-chloro(1,1'-biphenyl)-2-yl)methyl)-1-piperazinyl)benzoyl)-4-(((1R)-3-(dimethylamino)-1-((phenylsulfanyl)methyl)propyl)amino)-3-((trifluoromethyl)sulfonyl)benzenesulfonamide and N-(4-(4-((4'-chloro(1,1'-biphenyl)-2-yl)methyl)-1-piperazinyl)benzoyl)-4-(((1R)-3-(4-morpholinyl)-1-((phenylsulfanyl)methyl)propyl)amino)-3-((trifluoromethyl)sulfonyl)benzenesulfonamide, and therapeutically acceptable salts, prodrugs or salts of prodrugs thereof.

Variable moieties herein are represented by identifiers (capital letters with numerical and/or alphabetical superscripts) and may be specifically embodied.

It is meant to be understood that proper valences are maintained for all moieties and combinations thereof, that monovalent moieties having more than one atom are drawn from left to right and are attached through their left ends, and that divalent moieties are also drawn from left to right.

It is also meant to be understood that a specific embodiment of a variable moiety herein may be the same or different as another specific embodiment having the same identifier.

The term "cyclic moiety," as used herein, means benzene, aryl, cycloalkane, cycloalkyl, cycloalkene, cycloalkenyl, heteroarene, heteroaryl, heterocycloalkane, heterocycloalkyl, heterocycloalkene, heterocycloalkenyl, spiroalkyl, spiroalkenyl, spiroheteroalkyl and spiroheteroalkenyl.

The term "arene," as used herein, means benzene.

The term "aryl," as used herein, means phenyl.

The term "cycloalkane," as used herein, means $C_3$-cycloalkane, $C_4$-cycloalkane, $C_5$-cycloalkane, $C_6$-cycloalkane, $C_7$-cycloalkane, $C_8$-cycloalkane, $C_9$-cycloalkane, $C_{10}$-cycloalkane, $C_{11}$-cycloalkane, $C_{12}$-cycloalkane, $C_{13}$-cycloalkane and $C_{14}$-cycloalkane.

The term "cycloalkyl," as used herein, means $C_3$-cycloalkyl, $C_4$-cycloalkyl, $C_5$-cycloalkyl $C_6$-cycloalkyl, $C_7$-cycloalkyl, cloalkyl, $C_9$-cycloalkyl, $C_{10}$-cycloalkyl, $C_{11}$-cycloalkyl, $C_{12}$-cycloalkyl, $C_{13}$-cycloalkyl and $C_{14}$-cycloalkyl.

The term "cycloalkene," as used herein, means $C_4$-cycloalkene, $C_5$-cycloalkene, $C_6$-cycloalkene, $C_7$-cycloalkene, $C_8$-cycloalkene, $C_9$-cycloalkene, $C_{10}$-cycloalkene, $C_{11}$-cycloalkene, $C_{12}$-cycloalkene, $C_{13}$-cycloalkene and $C_{14}$-cycloalkene.

The term "cycloalkenyl," as used herein, means $C_3$-cycloalkenyl, $C_4$-cycloalkenyl, $C_5$-cycloalkenyl, $C_6$-cycloalkenyl, $C_7$-cycloalkenyl, $C_8$-cycloalkenyl, $C_9$-cycloalkenyl, $C_{10}$-cycloalkenyl, $C_{11}$-cycloalkenyl, $C_{12}$-cycloalkenyl, $C_{13}$-cycloalkenyl and $C_{14}$-cycloalkenyl.

The term "heteroarene," as used herein, means furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl.

The term "heterocycloalkane," as used herein, means cycloalkane having one or two or three $CH_2$ moieties replaced with independently selected O, C(O), CNOH, $CNOCH_3$, S, S(O), $SO_2$ or NH and one or two CH moieties unreplaced or replaced with N and also means cycloalkane having one or two or three $CH_2$ moieties unreplaced or replaced with independently selected O, C(O), CNOH, $CNOCH_3$, S, S(O), $SO_2$ or NH and one or two CH moieties replaced with N.

The term "heterocycloalkyl," as used herein, means cycloalkyl having one or two or three $CH_2$ moieties replaced with independently selected O, C(O), CNOH, $CNOCH_3$, S, S(O), $SO_2$ or NH and one or two CH moieties unreplaced or replaced with N and also means cycloalkyl having one or two or three $CH_2$ moieties unreplaced or replaced with independently selected O, C(O), CNOH, $CNOCH_3$, S, S(O), $SO_2$ or NH and one or two CH moieties replaced with N.

The term "heterocycloalkene," as used herein, means cycloalkene having one or two or three $CH_2$ moieties replaced with independently selected O, C(O), CNOH, $CNOCH_3$, S, S(O), $SO_2$ or NH and one or two CH moieties unreplaced or replaced with N and also means cycloalkene having one or two or three $CH_2$ moieties unreplaced or replaced with independently selected O, C(O), CNOH, $CNOCH_3$, S, S(O), $SO_2$ or NH and one or two CH moieties replaced with N.

The term "heterocycloalkenyl," as used herein, means cycloalkenyl having one or two or three $CH_2$ moieties replaced with independently selected O, C(O), CNOH, $CNOCH_3$, S, S(O), $SO_2$ or NH and one or two CH moieties unreplaced or replaced with N and also means cycloalkenyl having one or two or three $CH_2$ moieties unreplaced or replaced with independently selected O, C(O), CNOH, $CNOCH_3$, S, S(O), $SO_2$ or NH and one or two CH moieties replaced with N.

The term "spiroalkyl," as used herein, means $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl and $C_9$-spiroalkyl.

The term "spiroalkenyl," as used herein, means $C_2$-spiroalkenyl, $C_3$-spiroalkenyl, $C_4$-spiroalkenyl, $C_5$-spiroalkenyl, $C_6$-spiroalkenyl, $C_7$-spiroalkenyl, $C_8$-spiroalkenyl and $C_9$-spiroalkenyl.

The term "spiroheteroalkyl," as used herein, means spiroalkyl having one or two $CH_2$ moieties replaced with independently selected O, C(O), CNOH, $CNOCH_3$, S, S(O), $SO_2$ or NH.

The term "spiroheteroalkenyl," as used herein, means spiroalkenyl having one or two $CH_2$ moieties replaced with independently selected O, C(O), CNOH, $CNOCH_3$, S, S(O), $SO_2$ or NH and one or two CH moieties unreplaced or replaced with N and also means spiroalkenyl having one or two $CH_2$ moieties unreplaced or replaced with independently selected O, C(O), CNOH, $CNOCH_3$, S, S(O), $SO_2$ or NH and one or two CH moieties replaced with N.

The term "alkenyl," as used herein, means $C_2$-alkenyl, $C_3$-alkenyl, $C_4$-alkenyl, $C_5$-alkenyl and $C_6$-alkenyl.

The term "alkyl," as used herein, means $C_1$-alkyl, $C_2$-alkyl, $C_3$-alkyl, $C_4$-alkyl, $C_5$-alkyl and $C_6$-alkyl.

The term "alkynyl," as used herein, means $C_2$-alkynyl, $C_3$-alkynyl, $C_4$-alkynyl, $C_5$-alkynyl and $C_6$-alkynyl.

The term "$C_2$-alkenyl," as used herein, means ethenyl (vinyl).

The term "$C_3$-alkenyl," as used herein, means 1-propen-1-yl, 1-propen-2-yl (isopropenyl) and 1-propen-3-yl (allyl).

The term "$C_4$-alkenyl," as used herein, means I-buten-1-yl, 1-buten-2-yl, 1,3-butadien-1-yl, 1,3-butadien-2-yl, 2-buten-1-yl, 2-buten-2-yl, 3-buten-1-yl, 3-buten-2-yl, 2-methyl-1-propen-1-yl and 2-methyl-2-propen-1-yl.

The term "$C_5$-alkenyl," as used herein, means 2-methylene-3-buten-1-yl, 2-methylenebut-1-yl, 2-methyl-1-buten-1-yl, 2-methyl-1,3-butadien-1-yl, 3-methyl-1-buten-2-yl, 3-methyl-1,3-butadien-1-yl, 3-methyl-1,3-butadien-2-yl, 3-methyl-2-buten-1-yl, 3-methyl-2-buten-2-yl, 3-methyl-3-buten-1-yl, 3-methyl-3-buten-2-yl, 1-penten-1-yl, 1-penten-2-yl, 1-penten-3-yl, 1,3-pentadien-1-yl, 1,3-penta-dien-2-yl, 1,3-pentadien-3-yl, 1,4-pentadien-1-yl, 1,4-pentadien-2-yl, 1,4-pentadien-3-yl, 2-penten-1-yl, 2-penten-2-yl, 2-penten-3-yl, 2,4-pentadien-1-yl, 2,4-pentadien-2-yl, 3-penten-1-yl, 3-penten-2-yl, 4-penten-1-yl and 4-penten-2-yl.

The term "$C_6$-alkenyl," as used herein, means 2,2-dimethyl-3-buten-1-yl, 2,3-dimethyl-1-buten-1-yl, 2,3-dimethyl-1,3-butadien-1-yl, 2,3-dimethyl-2-buten-1-yl, 2,3-dimethyl-3-buten-1-yl, 2,3-dimethyl-3-buten-2-yl, 3,3-dimethyl-1-buten-1-yl, 3,3-dimethyl-1-buten-2-yl, 2-ethenyl-1,3-butadien-1-yl, 2-ethenyl-2-buten-1-yl, 2-ethyl-1-buten-1-yl, 2-ethyl-1,3-butadien-1-yl, 2-ethyl-2-buten-1-yl, 2-ethyl-3-buten-1-yl, 1-hexen-1-yl, 1-hexen-2-yl, 1-hexen-3-yl, 1,3-hexadien-1-yl, 1,3-hexadien-2-yl, 1,3-hexadien-3-yl, 1,3,5-hexatrien-1-yl, 1,3,5-hexatrien-2-yl, 1,3,5-hexatrien-3-yl, 1,4-hexadien-1-yl, 1,4-hexadien-2-yl, 1,4-hexadien-3-yl, 1,5-hexadien-1-yl, 1,5-hexadien-2-yl, 1,5-hexadien-3-yl, 2-hexen-1-yl, 2-hexen-2-yl, 2-hexen-3-yl, 2,4-hexadien-1-yl, 2,4-hexadien-2-yl, 2,4-hexadien-3-yl, 2,5-hexadien-1-yl, 2,5-hexadien-2-yl, 2,5-hexadien-3-yl, 3-hexen-1-yl, 3-hexen-2-yl, 3-hexen-3-yl, 3,5-hexadien-1-yl, 3,5-hexadien-2-yl, 3,5-hexadien-3-yl, 4-hexen-1-yl, 4-hexen-2-yl, 4-hexen-3-yl, 5-hexen-1-yl, 5-hexen-2-yl, 5-hexen-3-yl, 2-methylene-3-methyl-3-buten-1-yl, 2-methylene-3-methylbut-1-yl, 2-methylene-3-penten-1-yl, 2-methylene-4-penten-1-yl, 2-methylenepent-1-yl, 2-methylenepent-3-yl, 3-methylene-1-penten-1-yl, 3-methylene-1-penten-2-yl, 3-methylenepent-1-yl, 3-methylene-1,4-pentadien-1-yl, 3-methylene-1,4-pentadien-2-yl, 3-methylene-pent-2-yl, 2-methyl-1-penten-1-yl, 2-methyl-1-penten-3-yl, 2-methyl-1,3-pentadien-1-yl, 2-methyl-1,3-pentadien-3-yl, 2-methyl-1,4-pentadien-1-yl, 2-methyl-1,4-pentadien-3-yl, 2-methyl-2-penten-1-yl, 2-methyl-2-penten-3-yl, 2-methyl-2,4-pentadien-1-yl, 2-methyl-2,4-pentadien-3-yl, 2-methyl-3-penten-1-yl, 2-methyl-3-penten-2-yl, 2-methyl-3-penten-3-yl, 2-methyl-4-penten-1-yl, 2-methyl-4-penten-2-yl, 2-methyl-4-penten-3-yl, 3-methyl-1-penten-1-yl, 3-methyl-1-penten-2-yl, 3-methyl-1,3-pentadien-1-yl, 3-methyl-1,3-pentadien-2-yl, 3-methyl-1,4-pentadien-1-yl, 3-methyl-1,4-pentadien-2-yl, 3-methyl-2-penten-1-yl, 3-methyl-2-penten-2-yl, 3-methyl-2,4-pentadien-1-yl, 3-methyl-3-penten-1-yl, 3-methyl-3-penten-2-yl, 3-methyl-4-penten-1-yl, 3-methyl-4-penten-2-yl, 3-methyl-4-penten-3-yl, 4-methyl-1-penten-1-yl, 4-methyl-1-penten-2-yl, 4-methyl-1-penten-3-yl, 4-methyl-1,3-pentadien-1-yl, 4-methyl-1,3-pentadien-2-yl, 4-methyl-1,3-pentadien-3-yl, 4-methyl-1,4-pentadien-1-yl, 4-methyl-1,4-pentadien-2-yl, 4-methyl-1,4-pentadien-3-yl, 4-methylene-2-penten-3-yl, 4-methyl-2-penten-1-yl, 4-methyl-2-penten-2-yl, 4-methyl-2-penten-3- yl, 4-methyl-2,4-pentadien-1-yl, 4-methyl-2,4-pentadien-2-yl, 4-methyl-3-penten-1-yl, 4-methyl-3-penten-2-yl, 4-methyl-3-penten-3-yl, 4-methyl-4-penten-1-yl and 4-methyl-4-penten-2-yl.

The term "$C_1$-alkyl," as used herein, means methyl.

The term "$C_2$-alkyl," as used herein, means ethyl.

The term "$C_3$-alkyl," as used herein, means prop-1-yl and prop-2-yl (isopropyl).

The term "$C_4$-alkyl," as used herein, means but-1-yl, but-2-yl, 2-methylprop-1-yl and 2-methylprop-2-yl (tert-butyl).

The term "$C_5$-alkyl," as used herein, means 2,2-dimethylprop-1-yl (neo-pentyl), 2-methylbut-1-yl, 2-methylbut-2-yl, 3-methylbut-1-yl, 3-methylbut-2-yl, pent-1-yl, pent-2-yl and pent-3-yl.

The term "$C_6$-alkyl," as used herein, means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl and 4-methylpent-2-yl.

The term "$C_2$-alkynyl," as used herein, means ethynyl (acetylenyl).

The term "$C_3$-alkynyl," as used herein, means 1-propyn-1-yl and 2-propyn-1-yl (propargyl).

The term "$C_4$-alkynyl," as used herein, means 1-butyn-1-yl, 1,3-butadiyn-1-yl, 2-butyn-1-yl, 3-butyn-1-yl and 3-butyn-2-yl.

The term "$C_5$-alkynyl," as used herein, means 2-methyl-3-butyn-1-yl, 2-methyl-3-butyn-2-yl, 3-methyl-1-butyn-1-yl, 1,3-pentadiyn-1-yl, 1,4-pentadiyn-1-yl, 1,4-pentadiyn-3-yl, 2,4-pentadiyn-1-yl, 1-pentyn-1-yl, 1-pentyn-3-yl, 2-pentyn-1-yl, 3-pentyn-1-yl, 3-pentyn-2-yl, 4-pentyn-1-yl and 4-pentyn-2-yl.

The term "$C_6$-alkynyl," as used herein, means 2,2-dimethyl-3-butyn-1-yl, 3,3-dimethyl-1-butyn-1-yl, 2-ethyl-3-butyn-1-yl, 2-ethynyl-3-butyn-1-yl, 1-hexyn-1-yl, 1-hexyn-3-yl, 1,3-hexadiyn-1-yl, 1,3,5-hexatriyn-1-yl, 1,4-hexadiyn-1-yl, 1,4-hexadiyn-3-yl, 1,5-hexadiyn-1-yl, 1,5-hexadiyn-3-yl, 2-hexyn-1-yl, 2,5-hexadiyn-1-yl, 3-hexyn-1-yl, 3-hexyn-2-yl, 3,5-hexadiyn-2-yl, 4-hexyn-1-yl, 4-hexyn-2-yl, 4-hexyn-3-yl, 5-hexyn-1-yl, 5-hexyn-2-yl, 5-hexyn-3-yl, 2-methyl-3-pentyn-1-yl, 2-methyl-3-pentyn-2-yl, 2-methyl-4-pentyn-1-yl, 2-methyl-4-pentyn-2-yl, 2-methyl-4-pentyn-3-yl, 3-methyl-1-pentyn-1-yl, 3-methyl-4-pentyn-1-yl, 3-methyl-4-pentyn-2-yl, 3-methyl-1,4-pentadiyn-1-yl, 3-methyl-1,4-pentadiyn-3-yl, 3-methyl-4-pentyn-1-yl, 3-methyl-4-pentyn-3-yl, 4-methyl-1-pentyn-1-yl and 4-methyl-2-pentyn-1-yl.

The term "$C_4$-cycloalkane," as used herein, means cyclobutane.

The term "$C_5$-cycloalkane," as used herein, means cyclopentane.

The term "$C_6$-cycloalkane," as used herein, means cyclohexane.

The term "$C_7$-cycloalkane," as used herein, means cycloheptane.

The term "$C_8$-cycloalkane," as used herein, means cyclooctane.

The term "$C_9$-cycloalkane," as used herein, means cyclononane.

The term "$C_{10}$-cycloalkane," as used herein, means cyclodecane.

The term "$C_{11}$-cycloalkane," as used herein, means cycloundecane.

The term "$C_{12}$-cycloalkane," as used herein, means cyclododecane.

The term "$C_{13}$-cycloalkane," as used herein, means cyclotridecane.

The term "$C_{14}$-cycloalkane," as used herein, means cyclotetradecane.

The term "$C_4$-cycloalkene," as used herein, means cyclobutene and 1,3-cyclobutadiene.

The term "$C_5$-cycloalkene," as used herein, means cyclopentene and 1,3-cyclopentadiene.

The term "$C_6$-cycloalkene," as used herein, means cyclohexene, 1,3-cyclohexadiene and 1,4-cyclohexadiene.

The term "$C_7$-cycloalkene," as used herein, means cycloheptene and 1,3-cycloheptadiene.

The term "$C_8$-cycloalkene," as used herein, means cyclooctene, 1,3-cyclooctadiene, 1,4-cyclooctadiene, 1,5-cyclooctadiene, 1,3,5-cyclooctatriene and 1,3,6-cyclooctatriene.

The term "$C_9$-cycloalkene," as used herein, means cyclononene, 1,3-cyclononadiene, 1,4-cyclononadiene, 1,5-cyclononadiene, 1,3,5-cyclononatriene, 1,3,6-cyclononatriene, 1,3,7-cyclononatriene and 1,3,5,7-cyclononatetraene.

The term "$C_{10}$-cycloalkene," as used herein, means cyclodecene, 1,3-cyclodecadiene, 1,4-cyclodecadiene, 1,5-cyclodecadiene, 1,6-cyclodecadiene, 1,3,5-cyclodecatriene, 1,3,6-cyclodecatriene, 1,3,5,7-cyclodecatetraene, 1,3,5,8-cyclodecatetraene and 1,3,6,8-cyclodecatetraene.

The term "$C_{11}$-cycloalkene," as used herein, means cycloundecene, 1,3-cycloundecadiene, 1,4-cycloundecadiene, 1,5-cycloundecadiene, 1,6-cycloundecadiene, 1,3,5-cycloundecatriene, 1,3,6-cycloundecatriene, 1,3,7-cycloundecatriene, 1,4,7-cycloundecatriene, 1,4,8-cycloundecatriene, 1,3,5,7-cycloundecatetraene, 1,3,5,8-cycloundecatetraene, 1,3,6,8-cycloundecatetraene and 1,3,5,7,9-cycloundecapentaene.

The term "$C_{12}$-cycloalkene," as used herein, means cyclododecene, 1,3-cyclododecadiene, 1,4-cyclododecadiene, 1,5-cyclododecadiene, 1,6-cyclododecadiene, 1,7-cyclododecadiene, 1,3,5-cyclododecatriene, 1,3,6-cyclododecatriene, 1,3,7-cyclododecatriene, 1,3,8-cyclododecatriene, 1,4,7-cyclododecatriene, 1,4,8-cyclododecatriene, 1,5,9-cyclododecatriene, 1,3,5,7-cyclododecatetraene, 1,3,5,8-cyclododecatetraene, 1,3,5,9-cyclododecatetraene, 1,3,6,8-cyclododecatetraene, 1,3,6,9-cyclododecatetraene, 1,3,6,10-cyclododecatetraene, 1,3,7,9-cyclododecatetraene, 1,4,7,10-cyclododecatetraene, 1,3,5,7,9-cyclododecapentaene, 1,3,5,7,10-cyclododecapentaene and 1,3,5,8,10-cyclododecapentaene.

The term "$C_{13}$-cycloalkene," as used herein, means 1,3-cyclotridecadiene, 1,4-cyclotridecadiene, 1,5-cyclotridecadiene, 1,6-cyclotridecadiene, 1,7-cyclotridecadiene, 1,3,5-cyclotridecatriene, 1,3,6-cyclotridecatriene, 1,3,7-cyclotridecatriene, 1,3,8-cyclotridecatriene, 1,4,7-cyclotridecatriene, 1,4,8-cyclotridecatriene, 1,4,9-cyclotridecatriene, 1,5,9-cyclotridecatriene, 1,3,5,7-cyclotridecatetraene, 1,3,5,8-cyclotridecatetraene, 1,3,5,9-cyclotridecatetraene, 1,3,6,8-cyclotridecatetraene, 1,3,6,9-cyclotridecatetraene, 1,3,6,10-cyclotridecatetraene, 1,3,6,11-cyclotridecatetraene, 1,3,7,9-cyclotridecatetraene, 1,3,7,10-cyclotridecatetraene, 1,4,7,10-cyclotridecatetraene, 1,3,6,11-cyclotridecatetraene, 1,3,5,7,9-cyclotridecapentaene, 1,3,5,7,10-cyclotridecapentaene, 1,3,5,8,10-cyclotridecapentaene, 1,3,5,8,11-cyclotridecapentaene, 1,3,6,8,11-cyclotridecapentaene and 1,3,5,7,9,11-cyclotridecahexaene.

The term "$C_{14}$-cycloalkene," as used herein, means cyclotetradecene, 1,3-cyclotetradecadiene, 1,4-cyclotetradecadiene, 1,5-cyclotetradecadiene, 1,6-cyclotetradecadiene, 1,7-cyclotetradecadiene, 1,8-cyclotetradecadiene, 1,3,5- cyclotetradecatriene, 1,3,6-cyclotetradecatriene, 1,3,7-cyclotetradecatriene, 1,3,8-cyclotetradecatriene, 1,3,9-cyclotetradecatriene, 1,4,7-cyclotetradecatriene, 1,4,8-cyclotetradecatriene, 1,4,9-cyclotetradecatriene, 1,5,9-cyclotetradecatriene, 1,5,10-cyclotetradecatriene, 1,3,5,7-cyclotetradecatetraene, 1,3,5,8-cyclotetradecatetraene, 1,3,5,9-cyclotetradecatetraene, 1,3,5,10-cyclotetradecatetraene, 1,3,6,8-cyclotetradecatetraene, 1,3,6,9-cyclotetradecatetraene, 1,3,6,10-cyclotetradecatetraene, 1,3,6,11-cyclotetradecatetraene, 1,3,6,12-cyclotetradecatetraene, 1,3,7,9-cyclotetradecatetraene, 1,3,7,10-cyclotetradecatetraene, 1,3,7,11-cyclotetradecatetraene, 1,3,8,10-cyclotetradecatetraene, 1,4,7,10-cyclotetradecatetraene, 1,4,7,11-cyclotetradecatetraene, 1,4,8,11-cyclotetradecatetraene, 1,3,5,7,9-cyclotetradecapentaene, 1,3,5,7,10-cyclotetradecapentaene, 1,3,5,7,11-cyclotetradecapentaene, 1,3,5,8,10-cyclotetradecapentaene, 1,3,5,8,11-cyclotetradecapentaene, 1,3,5,8,12-cyclotetradecapentaene, 1,3,5,9,11-cyclotetradecapentaene, 1,3,5,8,11-cyclotetradecapentaene, 1,3,6,8,11-cyclotetradecapentaene, 1,3,6,9,11-cyclotetradecapentaene, 1,3,6,9,12-cyclotetradecapentaene, 1,3,5,8,11-cyclotetradecapentaene, 1,3,5,8,12-cyclotetradecapentaene, 1,3,5,7,9,11-cyclotetradecahexaene, 1,3,5,7,9,12-cyclotetradecahexaene, 1,3,5,7,10,12-cyclotetradecahexaene, 1,3,5,8,10,12-cyclotetradecahexaene and 1,3,5,7,9,11,13-cyclotetradecaheptaene.

The term "$C_3$-cycloalkenyl," as used herein, means cycloprop-1-en-1-yl and cycloprop-2-en-1-yl.

The term "$C_4$-cycloalkenyl," as used herein, means cyclobut-1-en-1-yl and cyclobut-2-en-1-yl.

The term "$C_5$-cycloalkenyl," as used herein, means cyclopent-1-en-1-yl, cyclopent-2-en-1-yl, cyclopent-3-en-1-yl and cyclopenta-1,3-dien-1-yl.

The term "$C_6$-cycloalkenyl," as used herein, means cyclohex-1-en-1-yl, cyclohex-2-en-1-yl, cyclohex-3-en-1-yl, cyclohexa-1,3-dien-1-yl, cyclohexa-1,4-dien-1-yl, cyclohexa-1,5-dien-1-yl, cyclohexa-2,4-dien-1-yl and cyclohexa-2,5-dien-1-yl.

The term "$C_7$-cycloalkenyl," as used herein, means bicyclo[2.2.1]hept-2-en-1-yl, bicyclo[2.2.1]hept-2-en-2-yl, bicyclo[2.2.1]hept-2-en-5-yl, bicyclo[2.2.1]hept-2-en-7-yl, bicyclo[2.2.1]hepta-2,5-dien-1-yl, bicyclo[2.2.1]hepta-2,5-dien-2-yl, bicyclo[2.2.1]hepta-2,5-dien-7-yl, cyclohept-1-en-1-yl, cyclohept-2-en-1-yl, cyclohept-3-en-1-yl, cyclohept-4-en-1-yl, cyclohepta-1,3-dien-1-yl, cyclohepta-1,4-dien-1-yl, cyclohepta-1,5-dien-1-yl, cyclohepta-1,6-dien-1-yl, cyclohepta-2,4-dien-1-yl, cyclohepta-2,5-dien-1-yl, cyclohepta-2,6-dien-1-yl, cyclohepta-3,5-dien-1-yl, cyclohepta-1,3,5-trien-1-yl, cyclohepta-1,3,6-trien-1-yl, cyclohepta-1,4,6-trien-1-yl and cyclohepta-2,4,6-trien-1-yl.

The term "$C_8$-cycloalkenyl," as used herein, means bicyclo[2.2.2]oct-2-en-1-yl, bicyclo[2.2.2]oct-2-en-2-yl, bicyclo[2.2.2]oct-2-en-5-yl, bicyclo[2.2.2]oct-2-en-7-yl, bicyclo[2.2.2]octa-2,5-dien-1-yl, bicyclo[2.2.2]octa-2,5-dien-2-yl, bicyclo[2.2.2]octa-2,5-dien-7-yl, bicyclo[2.2.2]octa-2,5,7-trien-1-yl, bicyclo[2.2.2]octa-2,5,7-trien-2-yl cyclooct-1-en-1-yl, cyclooct-2-en-1-yl, cyclooct-3-en-1-yl, cyclooct-4-en-1-yl, cycloocta-1,3-dien-1-yl, cycloocta-1,4-dien-1-yl, cycloocta-1,5-dien-1-yl, cycloocta-1,6-dien-1-yl, cycloocta1,7-dien-1-yl, cycloocta-2,4-dien-1-yl, cycloocta-2,5-dien-1-yl, cycloocta-2,6-dien-1-yl, cycloocta-2,7-dien-1-yl, cycloocta-3,5-dien-1-yl, cycloocta-3,6-dien-1-yl, cycloocta-1,3,5-trien-1-yl, cycloocta-1,3,6-trien-1-yl, cycloocta-1,3,7-trien-1-yl, cycloocta-1,4,6-trien-1-yl, cycloocta-1,4,7-trien-1-yl, cycloocta-1,5,7-trien-1-yl, cycloocta-2,4,6-trien-1-yl, cycloocta-2,4,7-trien-1-yl, cycloocta-2,5,7-trien-1-yl and cycloocta-1,3,5,7-tetraen-1-yl.

The term "$C_9$-cycloalkenyl," as used herein, means cyclonon-1-en-1-yl, cyclonon-2-en-1-yl, cyclonon-3-en-1-yl, cyclonon-4-en-1-yl, cyclonon-5-en-1-yl, cyclonona-1,3-dien-1-yl, cyclonona-1,4-dien-1-yl, cyclonona-1,5-dien-1-yl, cyclonona-1,6-dien-1-yl, cyclonona-1,7-dien-1-yl, cyclonona-1,8-dien-1-yl, cyclonona-2,4-dien-1-yl, cyclonona-2,5-dien-1-yl, cyclonona-2,6-dien-1-yl, cyclonona-2,7-dien-1-yl, cyclonona-2,8-dien-1-yl, cyclonona-3,5-dien-1-yl, cyclonona-3,6-dien-1-yl, cyclonona-3,7-dien-1-yl, cyclonona-4,6-dien-1-yl, cyclonona-1,3,5-trien-1-yl, cyclonona-1,3,6-trien-1-yl, cyclonona-1,3,7-trien-1-yl, cyclonona-1,3,8-trien-1-yl, cyclonona-1,4,6-trien-1-yl, cyclonona-1,4,7-trien-1-yl, cyclonona-1,4,8-trien-1-yl, cyclonona-1,5,7-trien-1-yl, cyclonona-1,5,8-trien-1-yl, cyclonona-1,6,8-trien-1-yl, cyclonona-2,4,8-trien-1-yl, cyclonona-2,4,6-trien-1-yl, cyclonona-2,4,7-trien-1-yl, cyclonona-2,4,8-trien-1-yl, cyclonona-2,5,7-trien-1-yl, cyclonona-2,5,8-trien-1-yl, cyclonona-1,3,5,7-tetraen-1-yl, cyclonona-1,3,5,8-tetraen-1-yl, cyclonona-1,3,6,8-tetraen-1-yl, cyclonona-1,4,6,8-tetraen-1-yl and cyclonona-2,4,6,8-tetraen-1-yl.

The term "$C_{10}$-cycloalkenyl," as used herein, means cyclodec-1-en-1-yl, cyclodec-2-en-1-yl, cyclodec-3-en-1-yl, cyclodec-4-en-1-yl, cyclodec-5-en-1-yl, cyclodeca-1,3-dien-1-yl, cyclodeca-1,4-dien-1-yl, cyclodeca-1,5-dien-1-yl, cyclodeca-1,6-dien-1-yl, cyclodeca-1,7-dien-1-yl, cyclodeca-1,8-dien-1-yl, cyclodeca-1,9-dien-1-yl, cyclodeca-2,4-dien-1-yl, cyclodeca-2,5-dien-1-yl, cyclodeca-2,6-dien-1-yl, cyclodeca-2,7-dien-1-yl, cyclodeca-2,8-dien-1-yl, cyclodeca-2,9-dien-1-yl, cyclodeca-3,5-dien-1-yl, cyclodeca-3,6-dien-1-yl, cyclodeca-3,7-dien-1-yl, cyclodeca-3,8-dien-1-yl, cyclodeca-4,6-dien-1-yl, cyclodeca-4,7-dien-1-yl, cyclodeca-1,3,5-trien-1-yl, cyclodeca-1,3,6-trien-1-yl, cyclodeca-1,3,7-trien-1-yl, cyclodeca-1,3,8-trien-1-yl, cyclodeca-1,3,9-trien-1-yl, cyclodeca-1,4,6-trien-1-yl, cyclodeca-1,4,7-trien-1-yl, cyclodeca-1,4,8-trien-1-yl, cyclodeca-1,4,9-trien-1-yl, cyclodeca-1,5,7-trien-1-yl, cyclodeca-1,5,8-trien-1-yl, cyclodeca-1,5,9-trien-1-yl, cyclodeca-1,6,8-trien-1-yl, cyclodeca-1,6,9-trien-1-yl, cyclodeca-1,7,9-trien-1-yl, cyclodeca-2,4,6-trien-1-yl, cyclodeca-2,4,7-trien-1-yl, cyclodeca-2,4,8-trien-1-yl, cyclodeca-2,4,9-trien-1-yl, cyclodeca-2,5,7-trien-1-yl, cyclodeca-2,5,8-trien-1-yl, cyclodeca-2,5,9-trien-1-yl, cyclodeca-2,6,8-trien-1-yl, cyclodeca-3,5,7-trien-1-yl, cyclodeca-3,5,8-trien-1-yl, cyclodeca-1,3,5,7-tetraen-1-yl, cyclodeca-1,3,5,8-tetraen-1-yl, cyclodeca-1,3,5,9-tetraen-1-yl, cyclodeca-1,3,6,8-tetraen-1-yl, cyclodeca-1,3,6,9-tetraen-1-yl, cyclodeca-1,3,7,9-tetraen-1-yl, cyclodeca-1,4,6,8-tetraen-1-yl, cyclodeca-1,4,6,9-tetraen-1-yl, cyclodeca-1,4,7,9-tetraen-1-yl, cyclodeca-1,5,7,9-tetraen-1-yl, cyclodeca-2,4,6,8-tetraen-1-yl, cyclodeca-2,4,6,9-tetraen-1-yl, cyclodeca-2,4,7,9-tetraen-1-yl and cyclodeca-1,3,5,7,9-pentaen-1-yl.

The term "$C_{11}$-cycloalkenyl," as used herein, means cycloundec-1-en-1-yl, cycloundec-2-en-1-yl, cycloundec-3-en-1-yl, cycloundec-4-en-1-yl, cycloundec-5-en-1-yl, cycloundec-6-en-1-yl, cycloundeca-1,3-dien-1-yl, cycloundeca-1,4-dien-1-yl, cycloundeca-1,5-dien-1-yl, cycloundeca-1,6-dien-1-yl, cycloundeca-1,7-dien-1-yl, cycloundeca-1,8-dien-1-yl, cycloundeca-1,9-dien-1-yl, cycloundeca-1,10-dien-1-yl, cycloundeca-2,4-dien-1-yl, cycloundeca-2,5-dien-1-yl, cycloundeca-2,6-dien-1-yl, cycloundeca-2,7-dien-1-yl, cycloundeca-2,8-dien-1-yl, cycloundeca-2,9-dien-1-yl, cycloundeca-2,10-dien-1-yl, cycloundeca-3,5-dien-1-yl, cycloundeca-3,6-dien-1-yl, cycloundeca-3,7-dien-1-yl, cycloundeca-3,8-dien-1-yl, cycloundeca-3,9-dien-1-yl, cycloundeca-4,6-dien-1-yl, cycloundeca-4,7-dien-1-yl, cycloundeca-4,8-dien-1-yl, cycloundeca-5,7-dien-1-yl, cycloundeca-1,3,5-trien-1-yl, cycloundeca-1,3,6-trien-1-yl, cycloundeca-1,3,7-trien-1-yl, cycloundeca-1,3,8-trien-1-yl, cycloundeca-1,3,9-trien-1-yl, cycloundeca-1,3,10-trien-1-yl, cycloundeca-1,4,6-trien-1-yl, cycloundeca-1,4,7-tri-en-1-yl, cycloundeca-1,4,8-trien-1-yl, cycloundeca-1,4,9-trien-1-yl, cycloundeca-1,4,10-trien-1-yl, cycloundeca-1,5,7-trien-1-yl, cycloundeca-1,5,8-trien-1-yl, cycloundeca-1,5,9-trien-1-yl, cycloundeca-1,5,10-trien-1-yl, cycloundeca-1,6,8-trien-1-yl, cycloundeca-1,6,9-trien-1-yl, cycloundeca-1,6,10-trien-1-yl, cycloundeca-1,7,9-trien-1-yl, cycloundeca-1,7,10-trien-1-yl, cycloundeca-1,8,10-trien-1-yl, cycloundeca-2,4,6-trien-1-yl, cycloundeca-2,4,7-trien-1-yl, cycloundeca-2,4,8-trien-1-yl, cycloundeca-2,4,9-trien-1-yl, cycloundeca-2,4,10-trien-1-yl, cycloundeca-2,5,7-trien-1-yl, cycloundeca-2,5,8-trien-1-yl, cycloundeca-2,5,9-trien-1-yl, cycloundeca-2,5,10-tri-en-1-yl, cycloundeca-2,6,8-trien-1-yl, cycloundeca-2,6,9-trien-1-yl, cycloundeca-2,6,10-trien-1-yl, cycloundeca-2,7,9-trien-1-yl, cycloundeca-3,5,7-trien-1-yl, cycloundeca-3,5,8-trien-1-yl, cycloundeca-3,5,9-trien-1-yl, cycloundeca-3,6,8-trien-1-yl, cycloundeca-3,6,9-trien-1-yl, cycloundeca-4,6,8-trien-1-yl, cycloundeca-1,3,5,7-tetraen-1-yl, cycloundeca-1,3,5,8-tetraen-1-yl, cycloundeca-1,3,5,9-tetraen-1-yl, cycloundeca-1,3,5,10-tetraen-1-yl, cycloundeca-1,3,6,8-tetraen-1-yl, cycloundeca-1,3,6,9-tetraen-1-yl, cycloundeca-1,3,6,10-tetraen-1-yl, cycloundeca-1,3,7,9-tetraen-1-yl, cycloundeca-1,3,7,10-tetraen-1-yl, cycloundeca-1,3,8,10-tetraen-1-yl, cycloundeca-1,4,6,8-tetraen-1-yl, cycloundeca-1,4,6,9-tetraen-1-yl, cycloundeca-1,4,6,10-tetraen-1-yl, cycloundeca-1,4,8,10-tetraen-1-yl, cycloundeca-1,5,7,9-tetraen-1-yl, cycloundeca-1,5,7,10-tetraen-1-yl, cycloundeca-1,5,8,10-tetraen-1-yl, cycloundeca-1,6,8,10-tetraen-1-yl, cycloundeca-2,4,6,8-tetraen-1-yl, cycloundeca-2,4,6,9-tetraen-1-yl, cycloundeca-2,4,6,10-tetraen-1-yl, cycloundeca-2,4,7,9-tetraen-1-yl, cycloundeca-2,5,7,9-tetraen-1-yl, cycloundeca-3,5,7,9-tetraen-1-yl, cycloundeca-1,3,5,7,9-pentaenyl, cycloundeca-1,3,5,7,10-pentaenyl, cycloundeca-1,3,5,8,10-pentaenyl, cycloundeca-1,3,6,8,10-pentaenyl, cycloundeca-1,4,6,8,10-pentaenyl and cycloundeca-2,4,6,8,10-pentaenyl.

The term "$C_{12}$-cycloalkenyl," as used herein, means cyclododec-1-en-1-yl, cyclododec-2-en-1-yl, cyclododec-3-en-1-yl, cyclododec-4-en-1-yl, cyclododec-5-en-1-yl, cyclododec-6-en-1-yl, cyclododeca-1,3-dien-1-yl, cyclododeca-1,4-dien-1-yl, cyclododeca-1,5-dien-1-yl, cyclododeca-1,6-dien-1-yl, cyclododeca-1,7-dien-1-yl, cyclododeca-1,8-dien-1-yl, cyclododeca-1,9-dien-1-yl, cyclododeca-1,10-dien-1-yl, cyclododeca-1,11-dien-1-yl, cyclododeca-2,4-dien-1-yl, cyclododeca-2,5-dien-1-yl, cyclododeca-2,6-dien-1-yl, cyclododeca-2,7-dien-1-yl, cyclododeca-2,8-dien-1-yl, cyclododeca-2,9-dien-1-yl, cyclododeca-2,10-dien-1-yl, cyclododeca-2,11-dien-1-yl, cyclododeca-3,5-dien-1-yl, cyclododeca-3,6-dien-1-yl, cyclododeca-3,7-dien-1-yl, cyclododeca-3,8-dien-1-yl, cyclododeca-3,9-dien-1-yl, cyclododeca-3,10-dien-1-yl, cyclododeca-3,11-dien-1-yl, cyclododeca-4,6-dien-1-yl, cyclododeca-4,7-dien-1-yl, cyclododeca-4,8-dien-1-yl, cyclododeca-4,9-dien-1-yl, cyclododeca-5,7-dien-1-yl, cyclododeca-5,8-dien-1-yl, cyclododeca-1,3,5-trien-1-yl, cyclododeca-1,3,6-trien-1-yl, cyclododeca-1,3,7-trien-1-yl, cyclododeca-1,3,8-trien-1-yl, cyclododeca-1,3,9-trien-1-yl, cyclododeca-1,3,10-trien-1-yl, cyclododeca-1,3,11-trien-1-yl, cyclododeca-1,4,6-trien-1-yl, cyclododeca-1,4,7-trien-1-yl, cyclododeca-1,4,8-trien-1-yl, cyclododeca-1,4,9-trien-1-yl, cyclododeca-1,4,10-trien-1-yl, cyclododeca-1,4,11-trien-1-yl, cyclododeca-1,5,7-trien-1-yl, cyclododeca-1,5,8-trien-1-yl, cyclododeca-1,5,9-trien-1-yl, cyclododeca-1,5,10-trien-1-yl, cyclododeca-1,5,11-trien-1-yl, cyclododeca-1,6,8-trien-1-yl, cyclododeca-1,6,9-trien-1-yl, cyclododeca-1,6,10-trien-1-yl, cyclododeca-1,6,11-trien-1-yl, cyclododeca-1,7,9-trien-1-yl, cyclododeca-1,7,10-trien-1-yl, cyclododeca-1,7,11-trien-1-yl, cyclododeca-1,8,10-trien-1-yl, cyclododeca-1,8,11-trien-1-yl, cyclododeca-1,9,11-trien-1-yl, cyclododeca-2,4,6-trien-1-yl, cyclododeca-2,4,7-trien-1-yl, cyclododeca-2,4,8-trien-1-yl, cyclododeca-2,4,9-trien-1-yl, cyclododeca-2,4,10-trien-1-yl, cyclododeca-2,4,11-trien-1-yl, cyclododeca-2,5,7-trien-1-yl, cyclododeca-2,5,8-trien-1-yl, cyclododeca-2,5,9-trien-1-yl, cyclododeca-2,5,10-trien-1-yl, cyclododeca-2,5,11-trien-1-yl, cyclododeca-2,6,8-trien-1-yl, cyclododeca-2,6,9-trien-1-yl, cyclododeca-2,6,10-trien-1-yl, cyclododeca-2,6,11-trien-1-yl, cyclododeca-2,7,9-trien-1-yl, cyclododeca-2,7,10-trien-1-yl, cyclododeca-2,8,10-trien-1-yl, cyclododeca-3,5,7-trien-1-yl, cyclododeca-3,5,8-trien-1-yl, cyclododeca-3,5,9-trien-1-yl, cyclododeca-3,5,10-trien-1-yl, cyclododeca-3,6,8-trien-1-yl, cyclododeca-3,6,9-trien-1-yl, cyclododeca-3,6,10-trien-1-yl, cyclododeca-3,7,9-trien-1-yl, cyclododeca-4,6,8-trien-1-yl, cyclododeca-4,6,9-trien-1-yl, cyclododeca-1,3,5,7-tetraen-1-yl, cyclododeca-1,3,5,8-tetraen-1-yl, cyclododeca-1,3,5,9-tetraen-1-yl, cyclododeca-1,3,5,1,0-tetraen-1-yl, cyclododeca-1,3,5,11-tetraen-1-yl, cyclododeca-1,3,6,8-tetraen-1-yl, cyclododeca-1,3,6,9-tetraen-1-yl, cyclododeca-1,3,6,10-tetraen-1-yl, cyclododeca-1,3,6,11-tetraen-1-yl, cyclododeca-1,3,7,9-tetraen-1-yl, cyclododeca-1,3,7,10-tetraen-1-yl, cyclododeca-1,3,7,11-tetraen-1-yl, cyclododeca-1,3,8,10-tetraen-1-yl, cyclododeca-1,3,8,11-tetraen-1-yl, cyclododeca-1,3,9,11-tetraen-1-yl, cyclododeca-1,4,6,8-tetraen-1-yl, cyclododeca-1,4,6,9-tetraen-1-yl, cyclododeca-1,4,6,10-tetraen-1-yl, cyclododeca-1,4,6,11-tetraen-1-yl, cyclododeca-1,4,7,9-tetraen-1-yl, cyclododeca-1,4,7,10-tetraen-1-yl, cyclododeca-1,4,7,11-tetraen-1-yl, cyclododeca-1,4,8,10-tetraen-1-yl, cyclododeca-1,4,8,11-tetraen-1-yl, cyclododeca-1,4,9,11-tetraen-1-yl, cyclododeca-1,5,7,9-tetraen-1-yl, cyclododeca-1,5,7,10-tetraen-1-yl, cyclododeca-1,5,7,11-tetraen-1-yl, cyclododeca-1,5,8,10-tetraen-1-yl, cyclododeca-1,5,8,11-tetraen-1-yl, cyclododeca-1,5,9,11-tetraen-1-yl, cyclododeca-1,6,8,10-tetraen-1-yl, cyclododeca-1,6,8,11-tetraen-1-yl, cyclododeca-1,6,9,11-tetraen-1-yl, cyclododeca-1,7,9,11-tetraen-1-yl, cyclododeca-2,4,6,8-tetraen-1-yl, cyclododeca-2,4,6,9-tetraen-1-yl, cyclododeca-2,4,6,10-tetraen-1-yl, cyclododeca-2,4,6,11-tetraen-1-yl, cyclododeca-2,4,7,9-tetraen-1-yl, cyclododeca-2,4,7,10-tetraen-1-yl, cyclododeca-2,4,7,11-tetraen-1-yl, cyclododeca-2,4,8,10-tetraen-1-yl, cyclododeca-2,4,8,11-tetraen-1-yl, cyclododeca-2,4,9,11-tetraen-1-yl, cyclododeca-2,5,7,9-tetraen-1-yl, cyclododeca-2,5,7,10-tetraen-1-yl, cyclododeca-2,5,7,11-tetraen-1-yl, cyclododeca-2,5,8,10-tetraen-1-yl, cyclododeca-2,5,8,11-tetraen-1-yl, cyclododeca-2,6,8,10-tetraen-1-yl, cyclododeca-3,5,7,9-tetraen-1-yl, cyclododeca-3,5,7,10-tetraen-1-yl, cyclododeca-3,5,8,10-tetraen-1-yl, cyclododeca-1,3,5,7,9-pentaen-1-yl, cyclododeca-1,3,5,7,10-pentaen-1-yl, cyclododeca-1,3,5,7,11-pentaen-1-yl, cyclododeca-1,3,5,8,10-pentaen-1-yl, cyclododeca-1,3,5,8,11-pentaen-1-yl, cyclododeca-1,3,5,9,11-pentaen-1-yl, cyclododeca-1,3,6,8,10-pentaen-1-yl, cyclododeca-1,3,6,8,11-pentaen-1-yl, cyclododeca-1,3,6,9,11-pentaen-1-yl, cyclododeca-1,3,7,9,11-pentaen-1-yl, cyclododeca-1,4,6,8,10-pentaen-1-yl, cyclododeca-1,4,6,8,11-pentaen-1-yl, cyclododeca-1,4,6,9,11-pentaen-1-yl, cyclododeca-1,4,7,9,11-pentaen-1-yl, cyclododeca-1,5,7,9,11-pentaen-1-yl, cyclododeca-2,4,6,8,10-pentaen-1-yl, cyclododeca-2,4,6,8,11-pentaen-1-yl, cyclododeca-2,4,6,9,11-pentaen-1-yl and cyclododeca-1,3,5,7,9,11-hexaen-1-yl.

The term "$C_{13}$-cycloalkenyl," as used herein, means cyclotridec-1-en-1-yl, cyclotridec-2-en-1-yl, cyclotridec-3-en-1-yl, cyclotridec-4-en-1-yl, cyclotridec-5-en-1-yl, cyclotridec-6-en-1-yl, cyclotridec-7-en-1-yl, cyclotrideca-1,3-dien-1-yl, cyclotrideca-1,4-dien-1-yl, cyclotrideca-1,5-dien-1-yl, cyclotrideca-1,6-dien-1-yl, cyclotrideca-1,7-dien-1-yl, cyclotrideca-1,8-dien-1-yl, cyclotrideca-1,9-dien-1-yl, cyclotrideca-1,10-dien-1-yl, cyclotrideca-1,1'-dien-1-yl, cyclotrideca-1,12-dien-1-yl, cyclotrideca-2,4-dien-1-yl, cyclotrideca-2,5-dien-1-yl, cyclotrideca-2,6-dien-1-yl, cyclotrideca-2,7-dien-1-yl, cyclotrideca-2,8-dien-1-yl, cyclotrideca-2,9-dien-1-yl, cyclotrideca-2,10-dien-1-yl, cyclotrideca-2,11-dien-1-yl, cyclotrideca-2,12-dien-1-yl, cyclotrideca-3,5-dien-1-yl, cyclotrideca-3,6-dien-1-yl, cyclotrideca-3,7-dien-1-yl, cyclotrideca-3,8-dien-1-yl, cyclotrideca-3,9-dien-1-yl, cyclotrideca-3,10-dien-1-yl, cyclotrideca-3,11-dien-1-yl, cyclotrideca-4,6-dien-1-yl, cyclotrideca-4,7-dien-1-yl, cyclotrideca-4,8-dien-1-yl, cyclotrideca-4,9-dien-1-yl, cyclotrideca-4,10-dien-1-yl, cyclotrideca-5,7-dien-1-yl, cyclotrideca-5,8-dien-1-yl, cyclotrideca-5,9-dien-1-yl, cyclotrideca-6,8-dien-1-yl, cyclotrideca-1,3,5-trien-1-yl, cyclotrideca-1,3,6-trien-1-yl, cyclotrideca-1,3,7-trien-1-yl, cyclotrideca-1,3,8-trien-1-yl, cyclotrideca-1,3,9-trien-1-yl, cyclotrideca-1,3,10-trien-1-yl, cyclotrideca-1,3,11-trien-1-yl, cyclotrideca-1,3,12-trien-1-yl, cyclotrideca-1,4,6-trien-1-yl, cyclotrideca-1,4,7-trien-1-yl, cyclotrideca-1,4,8-trien-1-yl, cyclotrideca-1,4,9-trien-1-yl, cyclotrideca-1,4,10-trien-1-yl, cyclotrideca-1,4,11-trien-1-yl, cyclotrideca-1,4,12-trien-1-yl, cyclotrideca-1,5,7-trien-1-yl, cyclotrideca-1,5,8-trien-1-yl, cyclotrideca-1,5,9-trien-1-yl, cyclotrideca-1,5,10-trien-1-yl, cyclotrideca-1,5,11-trien-1-yl, cyclotrideca-1,5,12-trien-1-yl, cyclotrideca-1,6,8-trien-1-yl, cyclotrideca-1,6,9-trien-1-yl, cyclotrideca-1,6,10-tri-en-1-yl, cyclotrideca-1,6,11-trien-1-yl, cyclotrideca-1,6,12-trien-1-yl, cyclotrideca-1,7,9-trien-1-yl, cyclotrideca-1,7,10-trien-1-yl, cyclotrideca-1,7,11-tri-en-1-yl, cyclotrideca-1,7,12-trien-1-yl, cyclotrideca-1,8,10-trien-1-yl, cyclotrideca-1,8,11-trien-1-yl, cyclotrideca-1,8,12-trien-1-yl, cyclotrideca-1,9,11-trien-1-yl, cyclotrideca-1,9,12-trien-1-yl, cyclotrideca-1,10,12-trien-1-yl, cyclotrideca-2,4,6-trien-1-yl, cyclotrideca-2,4,7-trien-1-yl, cyclotrideca-2,4,8-trien-1-yl, cyclotrideca-2,4,9-trien-1-yl, cyclotrideca-2,4,10-trien-1-yl, cyclotrideca-2,4,11-trien-1-yl, cyclotrideca-2,4,12-trien-1-yl, cyclotrideca-2,5,7-trien-1-yl, cyclotrideca-2,5,8-trien-1-yl, cyclotri-deca-2,5,9-trien-1-yl, cyclotri-deca-2,5,10-trien-1-yl, cyclotrideca-2,5,11-trien-1-yl, cyclotrideca-2,5,12-trien-1-yl, cyclotrideca-2,6,8-trien-1-yl, cyclotrideca-2,6,9-trien-1-yl, cyclotrideca-2,6,10-trien-1-yl, cyclotrideca-2,6,11-trien-1-yl, cyclotrideca-2,6,12-trien-1-yl, cyclotrideca-2,7,9-trien-1-yl, cyclotrideca-2,7,10-trien-1-yl, cyclotrideca-2,7,11-trien-1-yl, cyclotrideca-2,7,12-trien-1-yl, cyclotrideca-2,8,10-trien-1-yl, cyclotrideca-2,8,11-trien-1-yl, cyclotrideca-2,8,12-trien-1-yl, cyclotrideca-2,9,11-trien-1-yl, cyclotrideca-2,9,12-trien-1-yl, cyclotri-deca-2,10,12-trien-1-yl, cyclotrideca-3,5,7-trien-1-yl, cyclotrideca-3,5,8-trien-1-yl, cyclotrideca-3,5,9-trien-1-yl, cyclotrideca-3,5,10-trien-1-yl, cyclotrideca-3,5,11-trien-1-yl, cyclotrideca-3,6,8-trien-1-yl, cyclotrideca-3,6,9-trien-1-yl, cyclotrideca-3,6,10-trien-1-yl, cyclotrideca-3,6,11-trien-1-yl, cyclotrideca-3,7,9-trien-1-yl, cyclotrideca-3,7,10-trien-1-yl, cyclotrideca-3,7,11-tri-en-1-yl, cyclotrideca-3,8,10-trien-1-yl, cyclotrideca-4,6,8-trien-1-yl, cyclotrideca-4,6,9-trien-1-yl, cyclotri-deca-4,6,10-trien-1-yl, cyclotrideca-4,7,9-trien-1-yl, cyclotrideca-4,7,10-trien-1-yl, cyclotrideca-1,3,5,7-tetraen-1-yl, cyclotrideca-1,3,5,8-tetraen-1-yl, cyclotrideca-1,3,5,9-tetraen-1-yl, cyclotrideca-1,3,5,10-tetraen-1-yl, cyclotrideca-1,3,5,11-tetraen-1-yl, cyclotrideca-1,3,5,12-tetraen-1-yl, cyclotrideca-1,3,6,8-tetraen-1-yl, cyclotrideca-1,3,6,9-tetraen-1-yl, cyclotrideca-1,3,6,10-tetraen-1-yl, cyclotrideca-1,3,6,11-tetraen-1-yl, cyclotrideca-1,3,6,12-tetraen-1-yl, cyclotrideca-1,3,7,9-tetraen-1-yl, cyclotrideca-1,3,7,10-tetraen-1-yl, cyclotrideca-1,3,7,11-tetraen-1-yl, cyclotrideca-1,3,7,12-tetraen-1-yl, cyclotri-deca-1,3,8,10-tetraen-1-yl, cyclotrideca-1,3,8,11-tetraen-1-yl, cyclotrideca-1,3,8,12-tetraen-1-yl, cyclotrideca-1,3,9,11-tetraen-1-yl, cyclotrideca-1,3,9,12-tetraen-1-yl, cyclotrideca-1,3,10,12-tetraen-1-yl, cyclotrideca-1,4,6,8-tetraen-1-yl, cyclotrideca-1,4,6,9-tetraen-1-yl, cyclotri-deca-1,4,6,10-tetraen-1-yl, cyclotrideca-1,4,6,11-tetraen-1-yl, cyclotrideca-1,4,6,12-tetraen-1-yl, cyclotrideca-1,4,7,9-tetraen-1-yl, cyclotrideca-1,4,7,10-tetraen-1-yl, cyclotrideca-1,4,7,11-tetraen-1-yl, cyclotrideca-1,4,7,12-tetraen-1-yl, cyclotri-deca-1,4,8,10-tetraen-1-yl, cyclotri-deca-1,4,8,11-tetraen-1-yl, cyclotrideca-1,4,8,12-tetraen-1-yl, cyclotrideca-1,4,9,11-tetraen-1-yl, cyclotrideca-1,4,9,12-tetraen-1-yl, cyclotrideca-1,4,10,12-tetraen-1-yl, cyclotrideca-1,5,7,9-tetraen-1-yl, cyclotrideca-1,5,7,10-tetraen-1-yl, cyclotri-deca-1,5,7,11-tetraen-1-yl, cyclotri-deca-1,5,7,12-tetraen-1-yl, cyclotrideca-1,5,8,10-tetraen-1-yl, cyclotrideca-1,5,8,11-tetraen-1-yl, cyclotrideca-1,5,8,12-tetraen-1-yl, cyclotrideca-1,5,9,11-tetraen-1-yl, cyclotrideca-1,5,9,12-tetraen-1-yl, cyclotrideca-1,5,10,12-tetraen-1-yl, cyclotrideca-1,6,8,10-tetraen-1-yl, cyclotri-deca-1,6,8,11-tetraen-1-yl, cyclotrideca-1,6,8,12-tetraen-1-yl, cyclotrideca-1,6,9,11-tetraen-1-yl, cyclotrideca-1,6,9,12-tetraen-1-yl, cyclotrideca-1,6,10,12-tetraen-1-yl, cyclotrideca-1,7,9,11-tetraen-1-yl, cyclotrideca-1,7,9,12-tetraen-1-yl, cyclotri-deca-1,7,10,12-tetraen-1-yl, cyclotrideca-1,8,10,12-tetraen-1-yl, cyclotrideca-2,4,6,8-tetraen-1-yl, cyclotrideca-2,4,6,9-tetraen-1-yl, cyclotri-deca-2,4,6,10-tetraen-1-yl, cyclotrideca-2,4,6,11-tetraen-1-yl, cyclotrideca-2,4,6,12-tetraen-1-yl, cyclotrideca-2,4,7,9-tetraen-1-yl, cyclotri-deca-2,4,7,10-tetraen-1-yl, cyclotrideca-2,4,7,11-tetraen-1-yl, cyclotrideca-2,4,7,12-tetraen-1-yl, cyclotrideca-2,4,8,10-tetraen-1-yl, cyclotri-deca-2,4,8,11-tetraen-1-yl, cyclotrideca-2,4,8,12-tetraen-1-yl, cyclotrideca-2,4,9,11-tetraen-1-yl, cyclotrideca-2,4,9,12-tetraen-1-yl, cyclotrideca-2,4,10,12-tetraen-1-yl, cyclotrideca-2,5,7,9-tetraen-1-yl, cyclotrideca-2,5,7,10-tetraen-1-yl, cyclotrideca-2,5,7,11-tetraen-1-yl, cyclotrideca-2,5,7,12-tetraen-1-yl, cyclotrideca-2,5,8,10-tetraen-1-yl, cyclotrideca-2,5,8,11-tetraen-1-yl, cyclotrideca-2,5,8,12-tetraen-1-yl, cyclotri-deca-2,5,9,11-tetraen-1-yl, cyclotrideca-2,5,9,12-tetraen-1-yl, cyclotrideca-2,5,10,12-tetraen-1-yl, cyclotrideca-2,6,8,10-tetraen-1-yl, cyclotri-deca-2,6,8,11-tetraen-1-yl, cyclotrideca-2,6,8,12-tetraen-1-yl, cyclotrideca-2,6,9,11-tetraen-1-yl, cyclotrideca-2,6,9,12-tetraen-1-yl, cyclotri-deca-2,6,10,12-tetraen-1-yl, cyclotrideca-2,7,9,11-tetraen-1-yl, cyclotrideca-2,7,9,12-tetraen-1-yl, cyclotrideca-2,7,10,12-tetraen-1-yl, cyclotri-deca-3,5,7,9-tetraen-1-yl, cyclotrideca-3,5,7,10-tetraen-1-yl, cyclotrideca-3,5,7,11-tetraen-1-yl, cyclotrideca-3,5,8,10-tetraen-1-yl, cyclotri-deca-3,5,8,11-tetraen-1-yl, cyclotrideca-3,5,9,11-tetraen-1-yl, cyclotrideca-3,6,8,10-tetraen-1-yl, cyclotrideca-3,6,8,11-tetraen-1-yl, cyclotrideca-3,7,9,11-tetraen-1-yl, cyclotrideca-1,3,5,7,9-pentaen-1-yl, cyclotrideca-1,3,5,7,10-pentaen-1-yl, cyclotrideca-1,3,5,7,11-pentaen-1-yl, cyclotrideca-1,3,5,7,12-pentaen-1-yl, cyclotrideca-1,3,5,8,10-pentaen-1-yl, cyclotrideca-1,3,5,8,11-pentaen-1-yl, cyclotrideca-1,3,5,8,12-pentaen-1-yl, cyclotrideca-1,3,5,9,11-pentaen-1-yl, cyclotrideca-1,3,5,9,12-pentaen-1-yl, cyclotrideca-1,3,6,8,10-pentaen-1-yl, cyclotrideca-1,3,6,8,11-pentaen-1-yl, cyclotrideca-1,3,6,8,12-pentaen-1-yl, cyclotrideca-1,3,6,9,11-pentaen-1-yl, cyclotrideca-1,3,6,9,12-pentaen-1-yl, cyclotrideca-1,3,7,9,11-pentaen-1-yl, cyclotrideca-1,3,7,9,12-pentaen-1-yl, cyclotrideca-1,4,6,8,10-pentaen-1-yl, cyclotrideca-1,4,6,8,11-pentaen-1-yl, cyclotrideca-1,4,6,8,12-pentaen-1-yl, cyclotrideca-1,4,6,9,11-pentaen-1-yl, cyclotrideca-1,4,6,9,12-pentaen-1-yl, cyclotrideca-1,4,7,9,11-pentaen-1-yl, cyclotrideca-1,4,7,9,12-pentaen-1-yl, cyclotrideca-1,5,7,9,11-pentaen-1-yl, cyclotrideca-1,5,7,9,12-pentaen-1-yl, cyclotrideca-2,4,6,8,10-pentaen-1-yl, cyclotrideca-2,4,6,8,11-pentaen-1-yl, cyclotrideca-2,4,6,8,12-pentaen-1-yl, cyclotrideca-2,4,6,9,11-pentaen-1-yl, cyclotrideca-2,5,7,9,11-pentaen-1-yl, cyclotrideca-2,5,7,9,12-pentaen-1-yl, cyclotrideca-1,3,5,7,9,11-hexaen-1-yl and cyclotrideca-2,4,6,8,10,12-hexaen-1-yl.

The term "$C_{14}$-cycloalkenyl," as used herein, means cyclotetradec-1-en-1-yl, cyclotetradec-2-en-1-yl, cyclotetradec-3-en-1-yl, cyclotetradec-4-en-1-yl, cyclotetradec-5-en-1-yl, cyclotetradec-6-en-1-yl, cyclotetradec-7-en-1-yl, cyclotetradec-8-en-1-yl, cyclotetradeca-1,3-dien-1-yl, cyclotetradeca-1,4-dien-1-yl, cyclotetradeca-1,5-dien-1-yl, cyclotetradeca-1,6-dien-1-yl, cyclotetradeca-1,7-dien-1-yl, cyclotetradeca-1,8-dien-1-yl, cyclotetradeca-1,9-dien-1-yl, cyclotetradeca-1,10-dien-1-yl, cyclotetradeca-1,11-di-en-1-yl, cyclotetradeca-1,12-dien-1-yl, cyclotetradeca-1,13-dien-1-yl, cyclotetradeca-2,4-dien-1-yl, cyclotetradeca-2,5-dien-1-yl, cyclotetradeca-2,6-dien-1-yl, cyclotetradeca-2,7-dien-1-yl, cyclotetradeca-2,8-dien-1-yl, cyclotetradeca-2,9-dien-1-yl, cyclotetradeca-2,10-dien-1-yl, cyclotetradeca-2,11-dien-1-yl, cyclotetradeca-2,12-dien-1-yl, cyclotetradeca-2,13-dien-1-yl, cyclotetradeca-3,5-dien-1-yl, cyclotetradeca-3,6-dien-1-yl, cyclotetradeca-3,7-dien-1-yl, cyclotetradeca-3,8-dien-1-yl, cyclotetradeca-3,9-dien-1-yl, cyclotetradeca-3,10-dien-1-yl, cyclotetradeca-3,11-dien-1-yl, cyclotetradeca-3,12-dien-1-yl, cyclotetradeca-4,6-dien-1-yl, cyclotetradeca-4,7-dien-1-yl, cyclotetradeca-4,8-dien-1-yl, cyclotetradeca-4,9-dien-1-yl, cyclotetradeca-4,10-dien-1-yl, cyclotetradeca-4,11-dien-1-yl, cyclotetradeca-5,7-dien-1-yl, cyclotetradeca-5,8-dien-1-yl, cyclotetradeca-5,9-dien-1-yl, cyclotetradeca-5,10-dien-1-yl, cyclotetradeca-6,8-dien-1-yl, cyclotetradeca-6,9-dien-1-yl, cyclotetradeca-1,3,5-tetraen-1-yl, cyclotetradeca-1,3,6-tetraen-1-yl, cyclotetradeca-1,3,7-tetraen-1-yl, cyclotetradeca-1,3,8-tetraen-1-yl, cyclotetradeca-1,3,9-tetraen-1-yl, cyclotetradeca-1,3,10-tetraen-1-yl, cyclotetradeca-1,3,11-tetraen-1-yl, cyclotetradeca-1,3,12-tetraen-1-yl, cyclotetradeca-1,3,13-tetraen-1-yl, cyclotetradeca-1,4,6-tetraen-1-yl, cyclotetradeca-1,4,7-tetraen-1-yl, cyclotetradeca-1,4,8-tetraen-1-yl, cyclotetradeca-1,4,9-tetraen-1-yl, cyclotetradeca-1,4,10-tetraen-1-yl, cyclotetradeca-1,4,11-tetraen-1-yl, cyclotetradeca-1,4,12-tetraen-1-yl, cyclotetradeca-1,4,13-tetraen-1-yl, cyclotetradeca-1,5,7-tetraen-1-yl, cyclotetradeca-1,5,8-tetraen-1-yl, cyclotetradeca-1,5,9-tetraen-1-yl, cyclotetradeca-1,5,10-tetraen-1-yl, cyclotetradeca-1,5,11-tetraen-1-yl, cyclotetradeca-1,5,12-tetraen-1-yl, cyclotetradeca-1,5,13-tetraen-1-yl, cyclotetradeca-1,6,8-tetraen-1-yl, cyclotetradeca-1,6,9-tetraen-1-yl, cyclotetradeca-1,6,10-tetraen-1-yl, cyclotetradeca-1,6,11-tetraen-1-yl, cyclotetradeca-1,6,12-tetraen-1-yl, cyclotetradeca-1,6,13-tetraen-1-yl, cyclotetradeca-1,7,9-tetraen-1-yl, cyclotetradeca-1,7,10-tetraen-1-yl, cyclotetradeca-1,7,11-tetraen-1-yl, cyclotetradeca-1,7,12-tetraen-1-yl, cyclotetradeca-1,7,13-tetraen-1-yl, cyclotetradeca-1,8,10-tetraen-1-yl, cyclotetradeca-1,8,11-tetraen-1-yl, cyclotetradeca-1,8,12-tetraen-1-yl, cyclotetradeca-1,8,13-tetraen-1-yl, cyclotetradeca-1,9,11-tetraen-1-yl, cyclotetradeca-1,9,12-tetraen-1-yl, cyclotetradeca-1,9,13-tetraen-1-yl, cyclotetradeca-1,10,12-tetraen-1-yl, cyclotetradeca-1,10,13-tetraen-1-yl, cyclotetradeca-1,11,13-tetraen-1-yl, cyclotetradeca-2,4,6-tetraen-1-yl, cyclotetradeca-2,4,7-tetraen-1-yl, cyclotetradeca-2,4,8-tetraen-1-yl, cyclotetradeca-2,4,9-tetraen-1-yl, cyclotetradeca-2,4,10-tetraen-1-yl, cyclotetradeca-2,4,11-tetraen-1-yl, cyclotetradeca-2,4,12-tetraen-1-yl, cyclotetradeca-2,4,13-tetraen-1-yl, cyclotetradeca-2,5,7-tetraen-1-yl, cyclotetradeca-2,5,8-tetraen-1-yl, cyclotetradeca-2,5,9-tetraen-1-yl, cyclotetradeca-2,5,10-tetraen-1-yl, cyclotetradeca-2,5,11-tetraen-1-yl, cyclotetradeca-2,5,12-tetraen-1-yl, cyclotetradeca-2,5,13-tetraen-1-yl, cyclotetradeca-2,6,8-tetraen-1-yl, cyclotetradeca-2,6,9-tetraen-1-yl, cyclotetradeca-2,6,10-tetraen-1-yl, cyclotetradeca-2,6,11-tetraen-1-yl, cyclotetradeca-2,6,12-tetraen-1-yl, cyclotetradeca-2,6,13-tetraen-1-yl, cyclotetradeca-2,7,9-tetraen-1-yl, cyclotetradeca-2,7,10-tetraen-1-yl, cyclotetradeca-2,7,11-tetraen-1-yl, cyclotetradeca-2,7,12-tetraen-1-yl, cyclotetradeca-2,7,13-tetraen-1-yl, cyclotetradeca-2,8,10-tetraen-1-yl, cyclotetradeca-2,8,11-tetraen-1-yl, cyclotetradeca-2,8,12-tetraen-1-yl, cyclotetradeca-2,8,13-tetraen-1-yl, cyclotetradeca-2,9,11-tetraen-1-yl, cyclotetradeca-2,9,12-tetraen-1-yl, cyclotetradeca-2,9,13-tetraen-1-yl, cyclotetradeca-2,10,12-tetraen-1-yl, cyclotetradeca-2,10,13-tetraen-1-yl, cyclotetradeca-2,11,13-tetraen-1-yl, cyclotetradeca-3,5,7-tetraen-1-yl, cyclotetradeca-3,5,8-tetraen-1-yl, cyclotetradeca-3,5,9-tetraen-1-yl, cyclotetradeca-3,5,10-tetraen-1-yl, cyclotetradeca-3,5,11-tetraen-1-yl, cyclotetradeca-3,5,12-tetraen-1-yl, cyclotetradeca-3,6,8-tetraen-1-yl, cyclotetradeca-3,6,9-tetraen-1-yl, cyclotetradeca-3,6,10-tetraen-1-yl, cyclotetradeca-3,6,11-tetraen-1-yl, cyclotetradeca-3,6,12-tetraen-1-yl, cyclotetradeca-3,7,9-tetraen-1-yl, cyclotetradeca-3,7,10-tetraen-1-yl, cyclotetradeca-3,7,11-tetraen-1-yl, cyclotetradeca-3,7,12-tetraen-1-yl, cyclotetradeca-3,8,10-tetraen-1-yl, cyclotetradeca-3,8,11-tetraen-1-yl, cyclotetradeca-3,9,11-tetraen-1-yl, cyclotetradeca-4,6,8-tetraen-1-yl, cyclotetradeca-4,6,9-tetraen-1-yl, cyclotetradeca-4,6,10-tetraen-1-yl, cyclotetradeca-4,6,11-tetraen-1-yl, cyclotetradeca-4,7,9-tetraen-1-yl, cyclotetradeca-4,7,10-tetraen-1-yl, cyclotetradeca-4,7,11-tetraen-1-yl, cyclotetradeca-4,8,10-tetraen-1-yl, cyclotetradeca-1,3,5,7-tetraen-1-yl, cyclotetradeca-1,3,5,8-tetraen-1-yl, cyclotetradeca-1,3,5,9-tetraen-1-yl, cyclotetradeca-1,3,5,10-tetraen-1-yl, cyclotetradeca-1,3,5,11-tetraen-1-yl, cyclotetradeca-1,3,5,12-tetraen-1-yl, cyclotetradeca-1,3,5,13-tetraen-1-yl, cyclotetradeca-1,3,6,8-tetraen-1-yl, cyclotetradeca-1,3,6,9-tetraen-1-yl, cyclotetradeca-1,3,6,10-tetraen-1-yl, cyclotetradeca-1,3,6,11-tetraen-1-yl, cyclotetradeca-1,3,6,12-tetraen-1-yl, cyclotetradeca-1,3,6,13-tetraen-1-yl, cyclotetradeca-1,3,7,9-tetraen-1-yl, cyclotetradeca-1,3,7,10-tetraen-1-yl, cyclotetradeca-1,3,7,11-tetraen-1-yl, cyclotetradeca-1,3,7,12-tetraen-1-yl, cyclotetradeca-1,3,7,13-tetraen-1-yl, cyclotetradeca-1,3,8,10-tetraen-1-yl, cyclotetradeca-1,3,8,11-tetraen-1-yl, cyclotetradeca-1,3,8,12-tetraen-1-yl, cyclotetradeca-1,3,8,13-tetraen-1-yl, cyclotetradeca-1,3,9,11-tetraen-1-yl, cyclotetradeca-1,3,9,12-tetraen-1-yl, cyclotetradeca-1,3,9,13-tetraen-1-yl, cyclotetradeca-1,3,10,12-tetraen-1-yl, cyclotetradeca-1,3,10,13-tetraen-1-yl, cyclotetradeca-1,3,11,13-tetraen-1-yl, cyclotetradeca-1,4,6,8-tetraen-1-yl, cyclotetradeca-1,4,6,9-tetraen-1-yl, cyclotetradeca-1,4,6,10-tetraen-1-yl, cyclotetradeca-1,4,6,11-tetraen-1-yl, cyclotetradeca-1,4,6,12-tetraen-1-yl, cyclotetradeca-1,4,6,13-tetraen-1-yl, cyclotetradeca-1,4,7,9-tetraen-1-yl, cyclotetradeca-1,4,7,10-tetraen-1-yl, cyclotetradeca-1,4,7,11-tetraen-1-yl, cyclotetradeca-1,4,7,12-tetraen-1-yl, cyclotetradeca-1,4,7,13-tetraen-1-yl, cyclotetradeca-1,4,8,10-tetraen-1-yl, cyclotetradeca-1,4,8,11-tetraen-1-yl, cyclotetradeca-1,4,8,12-tetraen-1-yl, cyclotetradeca-1,4,8,13-tetraen-1-yl, cyclotetradeca-1,4,9,11-tetraen-1-yl, cyclotetradeca-1,4,9,12-tetraen-1-yl, cyclotetradeca-1,4,9, 13-tetraen-1-yl, cyclotetradeca-1,4,10,12-tetraen-1-yl, cyclotetradeca-1,4,10,13-tetraen-1-yl, cyclotetradeca-1,4,11,13-tetraen-1-yl, cyclotetradeca-1,5,7,9-tetraen-1-yl, cyclotetradeca-1,5,7,10-tetraen-1-yl, cyclotetradeca-1,5,7,11-tetraen-1-yl, cyclotetradeca-1,5,7,12-tetraen-1-yl, cyclotetradeca-1,5,7,13-tetraen-1-yl, cyclotetradeca-1,5,8,10-tetraen-1-yl, cyclotetradeca-1,5,8,11-tetraen-1-yl, cyclotetradeca-1,5,8,12-tetraen-1-yl, cyclotetradeca-1,5,8,13-tetraen-1-yl, cyclotetradeca-1,5,9,11-tetraen-1-yl, cyclotetradeca-1,5,9,12-tetraen-1-yl, cyclotetradeca-1,5,9,13-tetraen-1-yl, cyclotetradeca-1,5,10,12-tetraen-1-yl, cyclotetradeca-1,5,10,13-tetraen-1-yl, cyclotetradeca-1,5,11,13-tetraen-1-yl, cyclotetradeca-1,6,8,10-tetraen-1-yl, cyclotetradeca-1,6,8,11-tetraen-1-yl, cyclotetradeca-1,6,8,12-tetraen-1-yl, cyclotetradeca-1,6,8,13-tetraen-1-yl, cyclotetradeca-1,6,9,11-tetraen-1-yl, cyclotetradeca-1,6,9,12-tetraen-1-yl, cyclotetradeca-1,6,9,13-tetraen-1-yl, cyclotetradeca-1,6,10,12-tetraen-1-yl, cyclotetradeca-1,6,10,13-tetraen-1-yl, cyclotetradeca-1,6,11,13-tetraen-1-yl, cyclotetradeca-1,7,9,11-tetraen-1-yl, cyclotetradeca-1,7,9,12-tetraen-1-yl, cyclotetradeca-1,7,9,13-tetraen-1-yl, cyclotetradeca-1,7,10,12-tetraen-1-yl, cyclotetradeca-1,7,10,13-tetraen-1-yl, cyclotetradeca-1,7,11,13-tetraen-1-yl, cyclotetradeca-1,8,10,12-tetraen-1-yl, cyclotetradeca-1,8,10,13-tetraen-1-yl, cyclotetradeca-1,8,11,13-tetraen-1-yl, cyclotetradeca-2,4,6,8-tetraen-1-yl, cyclotetradeca-2,4,6,9-tetraen-1-yl, cyclotetradeca-2,4,6,10-tetraen-1-yl, cyclotetradeca-2,4,6,11-tetraen-1-yl, cyclotetradeca-2,4,6,12-tetraen-1-yl, cyclotetradeca-2,4,6,13-tetraen-1-yl, cyclotetradeca-2,4,7,9-tetraen-1-yl, cyclotetradeca-2,4,7,10-tetraen-1-yl, cyclotetradeca-2,4,7,11-tetraen-1-yl, cyclotetradeca-2,4,7,12-tetraen-1-yl, cyclotetradeca-2,4,7,13-tetraen-1-yl, cyclotetradeca-2,4,8,10-tetraen-1-yl, cyclotetradeca-2,4,8,11-tetraen-1-yl, cyclotetradeca-2,4,8,12-tetraen-1-yl, cyclotetradeca-2,4,8,13-tetraen-1-yl, cyclotetradeca-2,4,9,11-tetraen-1-yl, cyclotetradeca-2,4,9,12-tetraen-1-yl, cyclotetradeca-2,4,9,13-tetraen-1-yl, cyclotetradeca-2,4,10,12-tetraen-1-yl, cyclotetradeca-2,4,10,13-tetraen-1-yl, cyclotetradeca-2,4,11,13-tetraen-1-yl, cyclotetradeca-2,5,7,9-tetraen-1-yl, cyclotetradeca-2,5,7,10-tetraen-1-yl, cyclotetradeca-2,5,7,11-tetraen-1-yl, cyclotetradeca-2,5,7,12-tetraen-1-yl, cyclotetradeca-2,5,7,13-tetraen-1-yl, cyclotetradeca-2,5,8,10-tetraen-1-yl, cyclotetradeca-2,5,8,11-tetraen-1-yl, cyclotetradeca-2,5,8,12-tetraen-1-yl, cyclotetradeca-2,5,8,13-tetraen-1-yl, cyclotetradeca-2,5,9,11-tetraen-1-yl, cyclotetradeca-2,5,9,12-tetraen-1-yl, cyclotetradeca-2,5,9,13-tetraen-1-yl, cyclotetradeca-2,5,10,12-tetraen-1-yl, cyclotetradeca-2,5,10,13-tetraen-1-yl, cyclotetradeca-2,6,8,10-tetraen-1-yl, cyclotetradeca-2,6,8,11-tetraen-1-yl, cyclotetradeca-2,6,8,12-tetraen-1-yl, cyclotetradeca-2,6,8,13-tetraen-1-yl, cyclotetradeca-2,6,9,11-tetraen-1-yl, cyclotetradeca-2,6,9,12-tetraen-1-yl, cyclotetradeca-2,6,9,13-tetraen-1-yl, cyclotetradeca-2,6,10,12-tetraen-1-yl, cyclotetradeca-2,6,10,13-tetraen-1-yl, cyclotetradeca-2,6,11,13-tetraen-1-yl, cyclotetradeca-2,7,9,11-tetraen-1-yl, cyclotetradeca-2,7,9,12-tetraen-1-yl, cyclotetradeca-2,7,10,12-tetraen-1-yl, cyclotetradeca-3,5,7,9-tetraen-1-yl, cyclotetradeca-3,5,7,10-tetraen-1-yl, cyclotetradeca-3,5,7,11-tetraen-1-yl, cyclotetradeca-3,5,7,12-tetraen-1-yl, cyclotetradeca-3,5,8,10-tetraen-1-yl, cyclotetradeca-3,5,8,11-tetraen-1-yl, cyclotetradeca-3,5,8,12-tetraen-1-yl, cyclotetradeca-3,5,9,11-tetraen-1-yl, cyclotetradeca-3,5,9,12-tetraen-1-yl, cyclotetradeca-3,5,10,12-tetraen-1-yl, cyclotetradeca-3,6,8,10-tetraen-1-yl, cyclotetradeca-3,6,8,11-tetraen-1-yl, cyclotetradeca-3,6,8,12-tetraen-1-yl, cyclotetradeca-3,7,9,11-tetraen-1-yl, cyclotetradeca-1,3,5,7,9-pentaen-1-yl, cyclotetradeca-1,3,5,7,10-pentaen-1-yl, cyclotetradeca-1,3,5,7,11-pentaen-1-yl, cyclotetradeca-1,3,5,7,12-pentaen-1-yl, cyclotetradeca-1,3,5,7,13-pentaen-1-yl, cyclotetra-deca-1,3,5,8,10-pentaen-1-yl, cyclotetradeca-1,3,5,8,11-pentaen-1-yl, cyclotetradeca-1,3,5,8,12-pentaen-1-yl, cyclotetradeca-1,3,5,8,13-pentaen-1-yl, cyclotetradeca-1,3,5,9,11-pentaen-1-yl, cyclotetradeca-1,3,5,9,12-pentaen-1-yl, cyclotetradeca-1,3,5,9,13-pentaen-1-yl, cyclotetradeca-1,3,5,10,12-pentaen-1-yl, cyclotetradeca-1,3,5,10,13-pentaen-1-yl, cyclotetradeca-1,3,5,11,13-pentaen-1-yl, cyclotetradeca-1,3,6,8,10-pentaen-1-yl, cyclotetradeca-1,3,6,8,11-pentaen-1-yl, cyclotetradeca-1,3,6,8,12-pentaen-1-yl, cyclotetradeca-1,3,6,8,13-pentaen-1-yl, cyclotetradeca-1,3,6,9,11-pentaen-1-yl, cyclotetradeca-1,3,6,9,12-pentaen-1-yl, cyclotetradeca-1,3,6,9,13-pentaen-1-yl, cyclotetradeca-1,3,7,9,11-pentaen-1-yl, cyclotetradeca-1,3,7,9,12-pentaen-1-yl, cyclotetradeca-1,3,7,9,13-pentaen-1-yl, cyclotetradeca-1,4,6,8,10-pentaen-1-yl, cyclotetradeca-1,4,6,8,11-pentaen-1-yl, cyclotetradeca-1,4,6,8,12-pentaen-1-yl, cyclotetradeca-1,4,6,8,13-pentaen-1-yl, cyclotetradeca-1,4,6,9,11-pentaen-1-yl, cyclotetradeca-1,4,6,9,12-pentaen-1-yl, cyclotetradeca-1,4,6,9,13-pentaen-1-yl, cyclotetradeca-1,4,7,9,11-pentaen-1-yl, cyclotetradeca-1,4,7,9,12-pentaen-1-yl, cyclotetradeca-1,4,7,9,13-pentaen-1-yl, cyclotetradeca-1,5,7,9,11-pentaen-1-yl, cyclotetradeca-1,5,7,9,12-pentaen-1-yl, cyclotetradeca-1,5,7,9,13-pentaen-1-yl, cyclotetradeca-2,4,6,8,10-pentaen-1-yl, cyclotetradeca-2,4,6,8,11-pentaen-1-yl, cyclotetradeca-2,4,6,8,12-pentaen-1-yl, cyclotetradeca-2,4,6,8,13-pentaen-1-yl, cyclotetradeca-2,4,6,9,11-pentaen-1-yl, cyclotetradeca-2,4,6,9,12-pentaen-1-yl, cyclotetradeca-2,4,6,9,13-pentaen-1-yl, cyclotetradeca-2,4,6,10,12-pentaen-1-yl, cyclotetradeca-2,4,6,10,13-pentaen-1-yl, cyclotetradeca-2,4,6,1,13-pentaen-1-yl, cyclotetradeca-2,4,7,9,11-pentaen-1-yl, cyclotetradeca-2,4,7,9,12-pentaen-1-yl, cyclotetradeca-2,4,7,9,13-pentaen-1-yl, cyclotetradeca-2,4,7,10,12-pentaen-1-yl, cyclotetradeca-2,4,7,10,13-pentaen-1-yl, cyclotetradeca-2,4,7,11,13-pentaen-1-yl, cyclotetradeca-2,4,8,10,12-pentaen-1-yl, cyclotetradeca-2,4,8,10,13-pentaen-1-yl, cyclotetradeca-2,5,7,9,11-pentaen-1-yl, cyclotetradeca-2,5,7,9,12-pentaen-1-yl, cyclotetradeca-2,5,7,9,13-pentaen-1-yl, cyclotetradeca-2,5,7,10,12-pentaen-1-yl, cyclotetradeca-2,5,7,10,13-pentaen-1-yl, cyclotetradeca-1,3,5,7,9,11-hexaen-1-yl, cyclotetradeca-1,3,5,7,9,12-hexaen-1-yl, cyclotetradeca-1,3,5,7,9,13-hexaen-1-yl, cyclotetradeca-2,4,6,8,10,12-hexaen-1-yl, cyclotetradeca-2,4,6,8,10,13-hexaen-1-yl, cyclotetradeca-2,4,6,8,11,13-hexaen-1-yl and cyclotetradeca-1,3,5,7,9,11,13-heptaen-1-yl.

The term "$C_3$-cycloalkyl," as used herein, means cycloprop-1-yl.

The term "$C_4$-cycloalkyl," as used herein, means cyclobut-1-yl.

The term "$C_5$-cycloalkyl," as used herein, means cyclopent-1-yl.

The term "$C_6$-cycloalkyl," as used herein, means cyclohex-1-yl.

The term "$C_7$-cycloalkyl," as used herein, means bicyclo[2.2.1]hept-1-yl, bicyclo[2.2.1]hept-2-yl, cyclohept-1-yl, bicyclo[2.2.1]hept-7-yl and cyclohept-1-yl.

The term "$C_8$-cycloalkyl," as used herein, means bicyclo[2.2.2]oct-1-yl, bicyclo[2.2.2]oct-2-yl, bicyclo[2.2.2]oct-7-yl, cyclooct-1-yl.

The term "$C_9$-cycloalkyl," as used herein, means cyclonon-1-yl.

The term "$C_{10}$-cycloalkyl," as used herein, means adamant-1-yl, adamant-2-yl and cyclodec-1-yl.

The term "$C_{11}$-cycloalkyl," as used herein, means cycloundec-1-yl, tricyclo[4.3.1.1$^{3,8}$]undec-1-yl (homoadamant-1- yl), tricyclo[4.3.1.1$^{3,8}$]undec-2-yl (homoadamant-2-yl), tricyclo[4.3.1.1$^{3,8}$]undec-3-yl (homoadamant-3-yl), tricyclo[4.3.1.1$^{3,8}$]undec-4-yl (homoadamant-4-yl), and tricyclo[4.3.1.1$^{3,8}$]undec-9-yl (homoadamant-9-yl).

The term "$C_{12}$-cycloalkyl," as used herein, means cyclododec-1-yl.

The term "$C_{13}$-cycloalkyl," as used herein, means cyclotridec-1-yl.

The term "$C_{14}$-cycloalkyl," as used herein, means cyclotetradec-1-yl.

The term "$C_2$-spiroalkenyl," as used herein, means ethen-1,2-ylene, both ends of which replace hydrogen atoms of the same $CH_2$ moiety.

The term "$C_3$-spiroalkenyl," as used herein, means prop-1-en-1,3-ylene, both ends of which replace hydrogen atoms of the same $CH_2$ moiety.

The term "$C_4$-spiroalkenyl," as used herein, means but-1-en-1,4-ylene, but-2-en-1,4-ylene and buta-1,3-dien-1,4-ylene, both ends of which replace hydrogen atoms of the same $CH_2$ moiety.

The term "$C_5$-spiroalkenyl," as used herein, means pent-1-en-1,5-yl-ene, pent-2-en-1,5-ylene, penta-1,3-dien-1,5-ylene and penta-1,4-dien-1,5-ylene, both ends of which replace hydrogen atoms of the same $CH_2$ moiety.

The term "$C_6$-spiroalkenyl," as used herein, means hex-1-en-1,6-ylene, hex-2-en-1,6-ylene, hexa-1,3-dien-1,6-ylene, hexa-1,4-di-en-1,6-ylene and hexa-1,3,5-trien-1,6-ylene, both ends of which replace hydrogen atoms of the same $CH_2$ moiety.

The term "$C_7$-spiroalkenyl," as used herein, means hept-1-en-1,7-yl-ene, hept-2-en-1,7-ylene, hept-3-en-1,7-ylene, hepta-1,3-dien-1,7-ylene, hepta-1,4-dien-1,7-ylene, hepta-1,5-dien-1,7-ylene, hepta-2,4-dien-1,7-ylene, hepta-2,5-dien-1,7-ylene, hepta-1,3,5-trien-1,7-ylene and hepta-1,3,6-trien-1,7-ylene, both ends of which replace hydrogen atoms of the same $CH_2$ moiety.

The term "$C_8$-spiroalkenyl," as used herein, means oct-1-en-1,8-ylene, oct-2-en-1,8-ylene, oct-3-en-1,8-ylene, octa-1,3-dien-1,8-ylene, octa-1,4-dien-1,8-ylene, octa-1,5-dien-1,8-ylene, octa-1,6-dien-1,8-ylene, octa-2,4-dien-1,8-ylene, octa-2,5-dien-1,8-ylene, octa-3,5-dien-1,8-ylene, octa-1,3,5-trien-1,8-ylene, octa-1,3,6-trien-1,8-ylene and octa-2,4,6-trien-1,8-ylene, both ends of which replace hydrogen atoms of the same $CH_2$ moiety.

The term "$C_9$-spiroalkenyl," as used herein, means nona-1-en-1,9-yl-ene, nona-2-en-1,9-ylene, nona-3-en-1,9-ylene, nona-4-en-1,9-ylene, nona-1,3-dien-1,9-ylene, nona-1,4-dien-1,9-ylene, nona-1,5-dien-1,9-ylene, nona-1,6-dien-1,9-ylene, nona-1,7-dien-1,9-ylene, nona-1,8-dien-1,9-ylene, nona-2,4-dien-1,9-ylene, nona-2,5-dien-1,9-ylene, nona-2,6-dien-1,9-ylene, nona-2,7-dien-1,9-ylene, nona-3,5-dien-1,9-ylene, nona-3,6-dien-1,9-ylene, nona-4,6-dien-1,9-ylene, nona-1,3,5-trien-1,9-ylene, nona-1,3,6-trien-1,9-ylene, nona-1,3,7-trien-1,9-ylene, nona-1,3,8-trien-1,9-ylene, nona-1,4,6-trien-1,9-yl-ene, nona-1,4,7-trien-1,9-ylene, nona-1,4,8-trien-1,9-ylene, nona-1,5,7-trien-1,9-ylene, nona-2,4,6-trien-1,9-ylene, nona-2,4,7-trien-1,9-ylene, nona-1,3,5,7-tetraen-1,9-ylene, nona-1,3,5,8-tetraen-1,9-ylene and nona-1,3,6,9-tetraen-1,9-ylene, both ends of which replace hydrogen atoms of the same $CH_2$ moiety.

The term "$C_2$-spiroalkyl," as used herein, means eth-1,2-ylene, both ends of which replace hydrogen atoms of the same $CH_2$ moiety.

The term "$C_3$-spiroalkyl," as used herein, means prop-1,3-ylene, both ends of which replace hydrogen atoms of the same $CH_2$ moiety.

The term "$C_4$-spiroalkyl," as used herein, means but-1,4-ylene, both ends of which replace hydrogen atoms of the same $CH_2$ moiety.

The term "$C_5$-spiroalkyl," as used herein, means pent-1,5-ylene, both ends of which replace hydrogen atoms of the same $CH_2$ moiety.

The term "$C_6$-spiroalkyl," as used herein, means hex-1,6-ylene, both ends of which replace hydrogen atoms of the same $CH_2$ moiety.

The term "$C_7$-spiroalkyl," as used herein, means hept-1,7-ylene, both ends of which replace hydrogen atoms of the same $CH_2$ moiety.

The term "$C_8$-spiroalkyl," as used herein, means oct-1,8-ylene, both ends of which replace hydrogen atoms of the same $CH_2$ moiety.

The term "$C_9$-spiroalkyl," as used herein, means non-1,9-ylene, both ends of which replace hydrogen atoms of the same $CH_2$ moiety.

Compounds useful in the invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Compounds useful in the invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds may also exist as an equilibrium mixture of Z or E configurations.

Compounds useful in the invention containing NH, C(O)OH, OH or SH moieties may have attached thereto prodrug-forming moieties. The prodrug-forming moieties are removed by metabolic processes and release the compounds having the freed hydroxyl, amino or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance. For example, examples of prodrug-forming moieties for compounds having C(O)OH moieties are pivalate ($CH_2OC(O)C(CH_3)_3$) or phosphonooxy ($CH_2OP(O)(OH)_2$) esters.

Metabolites of compounds useful in the invention, produced by in vitro or in vivo metabolic processes, may also have utility for treating diseases associated with expression of an anti-apoptotic protein family member such as of Bcl-$X_L$, Bcl-2 and Bcl-w.

Certain precursor compounds which may be metabolized in vitro or in vivo to form compounds useful in the invention may also have utility for treating diseases associated with expression of an anti-apoptotic protein family member such as Bcl-$X_L$, and Bcl-2 and Bcl-w.

Compounds useful in the invention may exist as an acid addition salts, basic addition salts or zwitterions. Salts of the compounds are prepared during their isolation or following their purification. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds and prodrugs thereof are contemplated as being embraced by this invention. Basic addition salts of the compounds are those derived from the reaction of the compounds with the hydroxide, carbonate or bicarbonate of cations such as lithium, sodium, potassium, calcium, and magnesium.

Compounds useful in the invention may be administered, for example, bucally, ophthalmically, orally, osmotically, parenterally (intramuscularly, intraperintoneally intrasternally, intravenously, subcutaneously), rectally, topically, transdermally, or vaginally.

The compounds of this invention can also be incorporated into medical devices for introduction of compounds into selected tissues or organs in the body such as, but not limited to, coronary stents, peripheral stents, catheters, biliary stents, ureteural stents, CNS shunts and catheters, arterio-venous grafts, by-pass grafts and drug delivery balloons which are used in the vasculature; and one measure of the effectiveness of this invention is reduction in such as device-associated thrombi and complications associated therewith.

Accordingly, another embodiment of this invention comprises medical devices comprising a supporting structure having a coating in the surface thereof, said coating comprising a compound which prevents or treats a disease caused or exacerbated by an excess of, or undesired activation of, platelets in a mammal.

Therapeutically effective amounts of compounds useful in the invention depend on recipient of treatment, disorder being treated and severity thereof, composition containing it, time of administration, route of administration, duration of treatment, its potency, its rate of clearance and whether or not another drug is co-administered. The amount of a compound useful for the practice of this invention used to make a composition to be administered to a patient varies in doses from about 0.001 mg/kg to about 200 mg/kg body weight.

Compounds useful in the invention may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising an anti-apoptotic Bcl-2 family protein member useful for the practice of this invention to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising an anti-apoptotic Bcl-2 family protein member useful for the practice of this invention to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising an anti-apoptotic Bcl-2 family protein member useful for the practice of this invention to be administered osmotically include, for example, chlorofluorohydrocarbons, ethanol, water and mixtures thereof. Excipients for preparing compositions comprising an anti-apoptotic Bcl-2 family protein member useful for the practice of this invention to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising an anti-apoptotic Bcl-2 family protein member useful for the practice of this invention to be administered rectally or vaginally include, for example, cocoa butter, polyethylene glycol, wax and mixtures thereof.

Representative compounds that non-selectively or selectively inhibit the activity of an anti-apoptotic Bcl-2 family protein member were tested for their ability to lower the number of circulating platelets in mammals.

Potency is measured by $IC_{50}$ value, wherein $IC_{50}$ means concentration of compound needed for 50% inhibition.

BAX and BAD peptides are reported in Zhang, H. C., Nimmer, P., Rosenberg, S. H., Ng, S. C., and Joseph, M. (2002). Development of a High-Throughput Fluorescence Polarization Assay for Bcl-x(L). Analytical Biochemistry 307, 70-75.

Binding affinity of compounds to $Bcl-X_L$ protein is indicia of their inhibition of the activity of this protein. To determine the binding affinity of compounds to $Bcl-X_L$ protein, representative examples were diluted in DMSO to concentrations between 100 μM and 1 μM and added to each well of a 96-well microtiter plate. A mixture comprising 125 μL per well of assay buffer (20 mM phosphate buffer (pH 7.4), 1 mM EDTA, 50 mM NaCl, 0.05% PF-68), 6 nM of $Bcl-X_L$ protein (prepared as described in Science 1997, 275, 983-986), 1 nM fluorescein-labeled BAD peptide (prepared in-house) and the DMSO solution of the compound was shaken for 2 minutes and placed in a LJL Analyst (LJL Bio Systems, CA). A negative control (DMSO, 15 nM BAD peptide, assay buffer) and a positive control (DMSO, 1 nM BAD peptide, 6 nM $Bcl-X_L$, assay buffer) were used to determine the range of the assay. Polarization was measured at room temperature using a continuous Fluorescein lamp (excitation 485 nm, emission 530 nm). Percentage of inhibition was determined by (1-((mP value of well-negative control)/range))×100%.

Binding affinity of compounds to Bcl-2 protein is indicia of their inhibition of the activity of this protein. To determine the binding affinity of compounds to Bcl-2, representative examples were diluted in DMSO to concentrations between 10 μM and 10 μM and added to each well of a 96-well microtiter plate. A mixture comprising 125 L per well of assay buffer (20 mM phosphate buffer (pH 7.4), 1 mM EDTA, 50 mM NaCl, 0.05% PF-68), 10 nM of Bcl-2 protein (prepared according to the procedure described in PNAS 2001, 98, 3012-3017), 1 nM fluorescein-labeled BAX peptide (prepared in-house) and the DMSO solution of the representative example was shaken for 2 minutes and placed in a LJL Analyst (LJL Bio Systems, CA. Polarization was measured at room temperature using a continuous Fluorescein lamp (excitation 485 nm, emission 530 nm). Percentage of inhibition was determined by (1-((mP value of well-negative control)/range))×100%.

The effect of the Bcl-2 family protein inhibitors on circulating platelets has been demonstrated in multiple species including, but not limited to, mouse, rat, dog and monkey. The effect of Bcl-2 protein inhibitors on circulating platelets can be determined by administration of test compounds, preferably orally or intravenously, to an animal and analyzing a blood sample and determining the number of platelets by techniques well-known in the art. Preferably, blood samples are obtained from about 2 hours to about 48 hours after compound administration.

Male beagle dogs (n=3/group; 8-12 kg) were treated with a single dose of 5 mg/kg N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide in 10:30:60 ethanol/phosal 50 PG/PEG 400 (by weight) by oral gavage. Blood samples were collected at baseline and at the indicated time points from the jugular vein, treated with EDTA and the whole blood analyzed for platelet counts on a Cell-Dyn 3700 (Abbott Laboratories). The results are shown in FIG. 1, wherein a rapid reduction in circulating platelet count in dogs after one 5 mg/kg oral dose of drug was observed.

Figure 2:
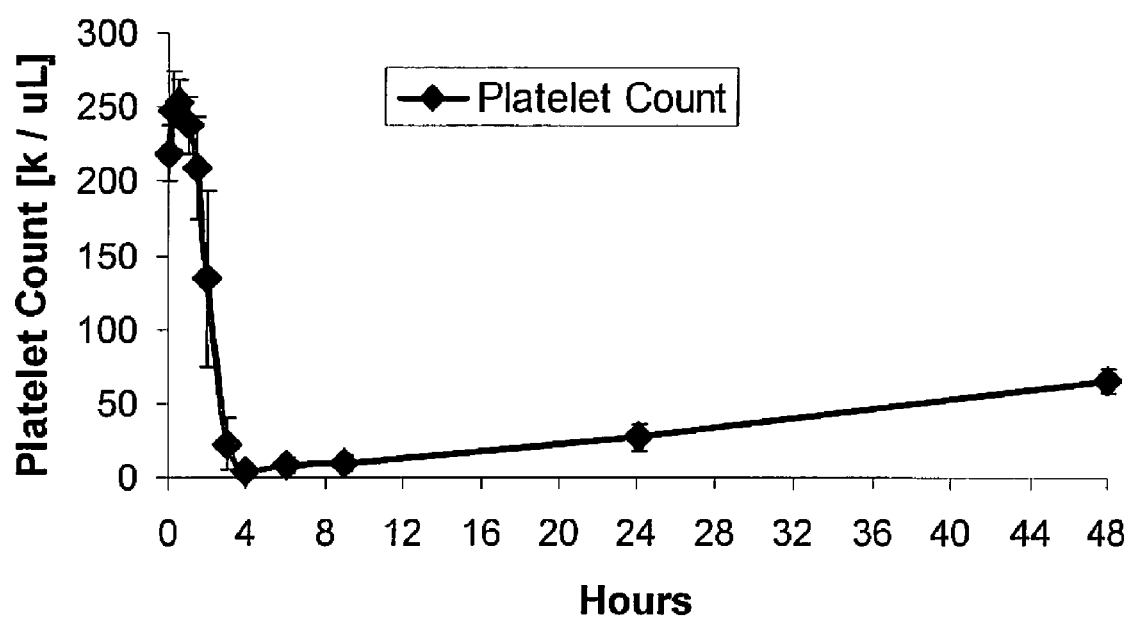
FIG. 2 shows the effect of oral administration of 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide on circulating platelets in dogs over 48 hours.

Male beagle dogs (n=3/group; 8-12 kg) were treated with a single dose of 5 mg/kg 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide in 10:90 DMSO/PEG 400 (by volume) by oral gavage. Blood samples were collected at baseline and at the indicated time points from the jugular vein, treated with EDTA and the whole blood analyzed for platelet counts on a Cell-Dyn 3700 (Abbott Laboratories). The results are shown in FIG. 2, wherein a similar reduction in circulating platelet count in dogs after one 5 mg/kg oral dose of drug was observed.

Figure 3:
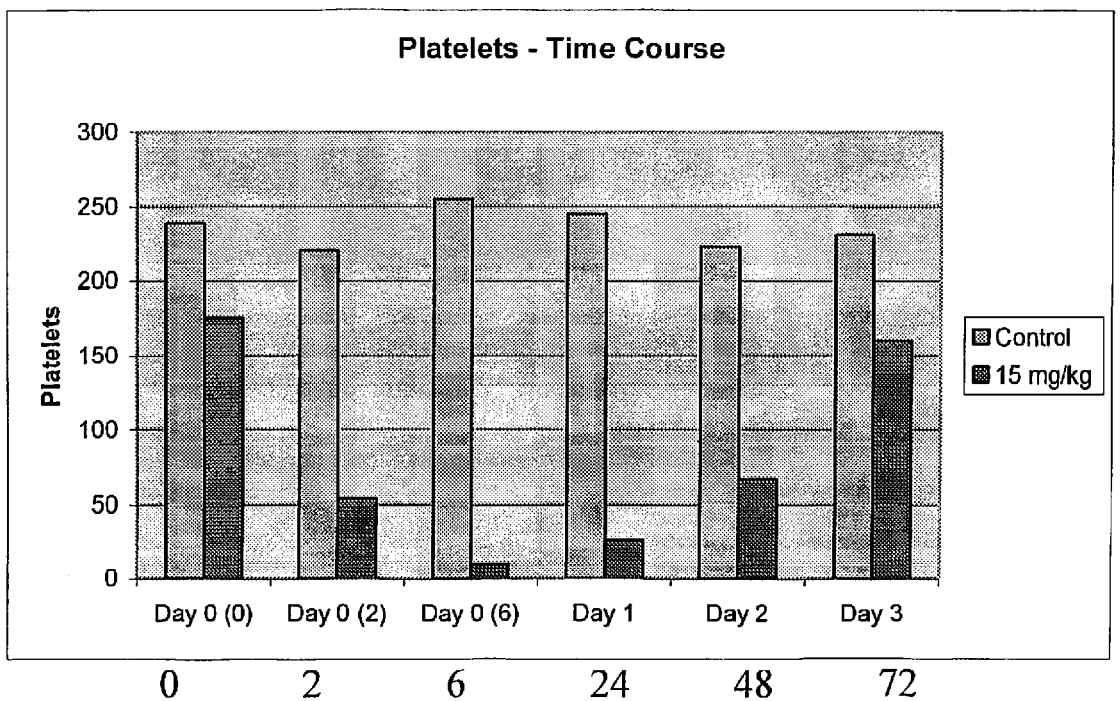
FIG. 3 shows the comparative effect of intravenous administration of N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide versus the vehicle in which it is administered on circulating platelets in dogs over 72 hours.

Two male and two female beagle dogs (n=4/group, 8-12 kg) received single dosages of 15 mg/kg of Example N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide in Captisol® (modified cyclodextrin) or vehicle control via an intravenous catheter jugular vein) over a four-hour infusion period. Blood samples were collected at baseline and at 2, 6, 24, 48 and 72 hours post dosing from the jugular vein, treated with EDTA and the whole blood analyzed for platelet counts on a Cell-Dyn 3700 (Abbott Laboratories). The results are shown in FIG. 3, wherein the effect on circulating platelet count of a single 15 mg/kg intravenous dose of versus control (the vehicle in which it was administered) in dogs over a three day (72 hour period) including time intervals of 0, 2 and 6 hour periods on day 0 was observed.

Figure 4:
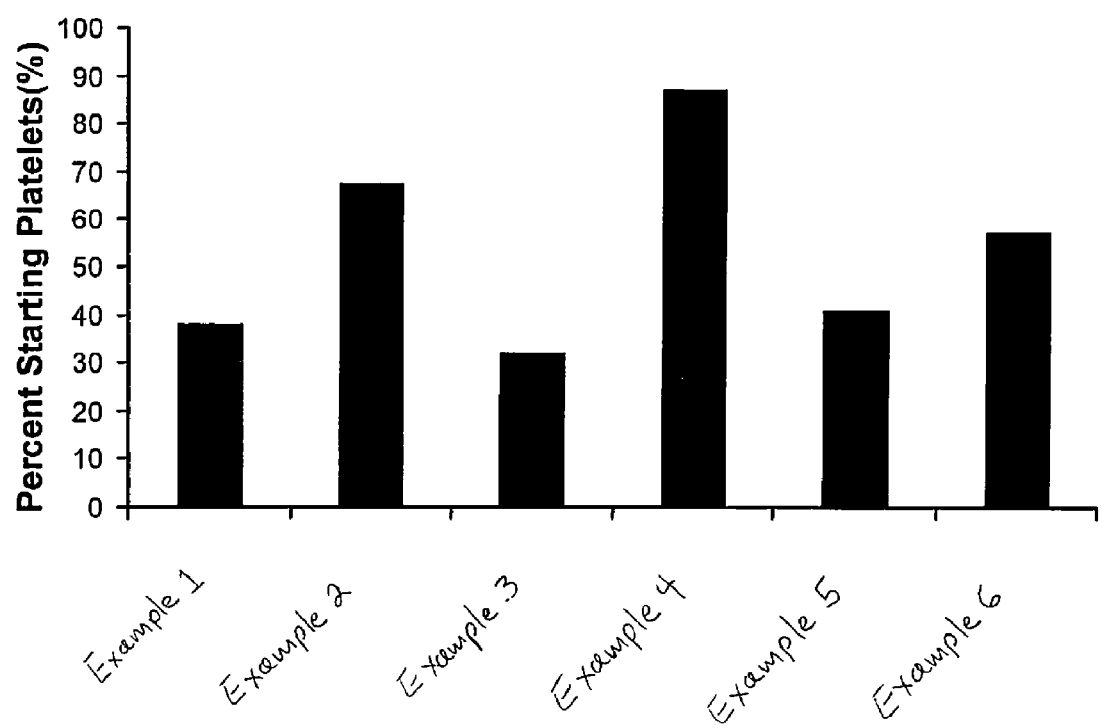
FIG. 4 shows the effect of oral administration of representative compounds
3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)benzenesulfonamide (EXAMPLE 1),
N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (EXAMPLE 2),
N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide (EXAMPLE 3),
N-(4-(4-((2-(4-chlorophenyl)cyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide (EXAMPLE 4),
3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide (EXAMPLE 5), and
N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (EXAMPLE 6),
that inhibits the activity of anti-apoptotic Bcl-2 family protein members on circulating platelets in dogs.

Male beagle dogs (n=3/group; 8-12 kg) were treated with a single dose of 2.5 mg/kg Examples 1-6 in 10:90 DMSO/PEG 400 (by volume) by oral gavage. Blood samples were collected at baseline and 6 hours post compound administration from the jugular vein, treated with EDTA and the whole blood analyzed for platelet counts on a Cell-Dyn 3700 (Abbott Laboratories). Percent starting platelet counts (PC) were calculated using the following equation. $[1-(PC_{t=0}-PC_{t=6})/PC_{t=0}]\times100\%$. The results are shown in FIG. 4, wherein the effect on circulating platelet count of a single 2.5 mg/kg oral dose of each of EXAMPLES 1-6 in dogs at 6 hours after dosing was observed.

Figure 5:
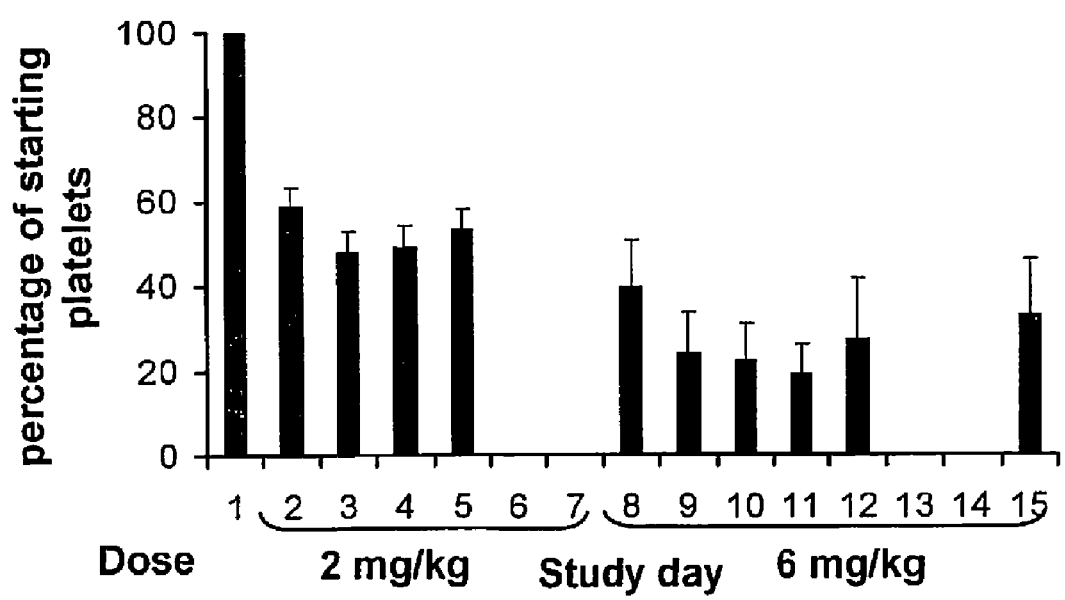
FIG. 5 shows the effect of multiple oral daily dosing of N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide on the amount of circulating platelets in dogs.

Male beagle dogs (n=3/group; 8-12 kg) were treated once daily with N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide in 10:90 DMSO/PEG 400 (by volume) by oral gavage at a dose of 2 mg/kg on days 2-7 and at a dose of 6 mg/kg on days 8-15 of the study. Blood samples were collected at baseline and 6 hours post dosing on days 2-5, 8-12 and day 15 from the jugular vein, treated with EDTA and the whole blood analyzed for platelet counts on a Cell-Dyn 3700 (Abbott Laboratories). Percent starting platelet counts (PC) were calculated using the following equation. $[1-(PC_{t=0}-PC_{t=6})/PC_{t=0}]\times100\%$. The results are shown in FIG. 5, wherein the proportionate effect of multiple oral dosing of drug on circulating platelet count in dogs was observed.

Additionally, exemplary anti-apoptotic Bcl-2 family protein member inhibitor EXAMPLE 2 induced a unique thrombocytopenia in multiple species that is characterized by a rapid clearance of circulating platelets with recovery to normal platelet counts within several days after treatment.

Furthermore, anti-apoptotic Bcl-2 family protein member inhibitor EXAMPLE 2 reduced the viability of dog and human platelets and activated apoptotic processes such as cytochrome c release, caspase 3 activation and PS (phosphotidyl serine) externalization. EXAMPLE 2 did not induce aggregation of isolated platelets.

Criteria for diagnosis of essential thrombocythemia (ET) and exclusion are known. Exemplary criteria can be those used in published anagrelide or hydroxyurea studies, such as those by C. Harrison, et al., *Hydroxyurea Compared with Anagrelide in High Risk Essential Thrombocythemia, N. Engl. J. Med.* 2005, 353 (1), 33-45.

ET patients can be stratified according to whether they met any of the criteria for vascular events, such as age, existing or previous platelet count of 1 million/ml$^3$, history of ischemia, thrombosis or embolism, hemorrhage caused by ET, hypertension requiring therapy and diabetes requiring medication.

Patients are then dosed. For chronic ET patients, dosing of compounds according to the invention may be sustained for a period of time until a desirable reduction in platelet count and/or steady state is accomplished. Perioperative administration of compounds according to the invention to patients with undesirable platelet levels (though not necessarily at levels high enough to constitute ET) may be more limited, such as before or during or post-operatively or at two or more of these time periods depending on the level of platelet reduction desired and the patient.

It is also contemplated that biomarker level may be an important endpoint.

For certain disease states, the physician may desire to lower even normal platelet counts. Thus, it is contemplated that a compound according to the present invention can be administered from a coated stent, for example, that has been implanted in a patient.

As a proxy for platelet count, bleeding events or thrombosis may be used as endpoints.

EXAMPLE 1

3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)benzenesulfonamide

EXAMPLE 2

N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide

EXAMPLE 3

N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide

EXAMPLE 4

N-(4-(4-((2-(4-chlorophenyl)cyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide

EXAMPLE 5

3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide

EXAMPLE 6

N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide

EXAMPLE 7

N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide The foregoing is meant to illustrate the invention and not limit it to the disclosed embodiments. Variations and changes obvious to one skilled in the art are intended to be within the scope and nature of the invention as defined in the claims.

We claim:

1. A method of treating a disease caused or exacerbated by an excess of, or undesired activation of, platelets in a mammal comprising administering a compound to the mammal, wherein the disease is essential thrombocythemia, polycythemia vera, device-associated thrombi, or cardiovascular disease, and wherein the compound is selected from the group consisting of:

3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)benzenesulfonamide;

N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide;

N-(4-(4-((2-(4-chlorophenyl)-5,5-dimethylcyclohex-1-en-1-yl)methyl)piperazin-1-yl)benzoyl)-4-(((1R)-3-(morpholin-4-yl)-1-((phenylsulfanyl)methy)propyl)amino)-3-((trifluoromethyl)sulfonyl)benzenesulfonamide;

3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide;

N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide; and N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide;

or therapeutically acceptable salt thereof.

2. The method of claim 1, wherein the disease is polycythemia vera.

3. The method of claim 1 or 2, wherein the compound is N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, or therapeutically acceptable salt thereof.

4. The method of claim 1 or 2, wherein the compound is 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)benzenesulfonamide, or therapeutically acceptable salt thereof.

5. The method of claim 1 or 2, wherein the compound is N-(4-(4-((2-(4-chlorophenyl)-5,5-dimethylcyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or therapeutically acceptable salt thereof.

6. The method of claim 1 or 2, wherein the compound is 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide, or therapeutically acceptable salt thereof.

7. The method of claim 1 or 2, wherein the compound is N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, or therapeutically acceptable salt thereof.

8. The method of claim 1 or 2, wherein the compound is N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyemethyl)propyl)amino)-3-((trifluoromethyl)sulfonyl)benzenesulfonamide, or therapeutically acceptable salt thereof.

* * * * *

UNITED STATES PATENT AND TRADEMARK OFFICE
CERTIFICATE OF CORRECTION

PATENT NO. : 7,842,681 B2  
APPLICATION NO. : 11/850274  
DATED : November 30, 2010  
INVENTOR(S) : Elmore et al.

It is certified that error appears in the above-identified patent and that said Letters Patent is hereby corrected as shown below:

Column 68, line 7, claim 1: "methy)propyl)" to read as --methyl)propyl)--

Column 68, line 60, claim 8: "(phenylsulfanyemethyl)" to read as --(phenylsulfanyl)methyl)--

Signed and Sealed this

Twenty-second Day of February, 2011

David J. Kappos  
*Director of the United States Patent and Trademark Office*